United States Patent
Liu et al.

(10) Patent No.: US 9,868,727 B2
(45) Date of Patent: Jan. 16, 2018

(54) FACTOR XIA INHIBITORS

(71) Applicant: Merck Sharp & Dohme Corp., Rahway, NJ (US)

(72) Inventors: Weiguo Liu, Princeton, NJ (US); Scott D. Edmondson, Clark, NJ (US); Zhuyan Guo, Scotch Plains, NJ (US); Sung-Sau So, Verona, NJ (US); Anthony K. Ogawa, New Providence, NJ (US); Rongze Kuang, Green Brook, NJ (US); Heping Wu, Edison, NJ (US); Amjad Ali, Freehold, NJ (US); Ying-Duo Gao, Holmdel, NJ (US); Yu Jiang, East Windsor, NJ (US); Chunsing Li, Shanghai (CN); Tingting Yu, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/329,634

(22) PCT Filed: Jul. 23, 2015

(86) PCT No.: PCT/CN2015/084937
§ 371 (c)(1),
(2) Date: Jan. 27, 2017

(87) PCT Pub. No.: WO2016/015593
PCT Pub. Date: Feb. 4, 2016

(65) Prior Publication Data
US 2017/0210732 A1     Jul. 27, 2017

Related U.S. Application Data

(60) Provisional application No. 62/029,758, filed on Jul. 28, 2014.

(51) Int. Cl.
| | |
|---|---|
| C07D 409/14 | (2006.01) |
| C07D 417/14 | (2006.01) |
| C07D 413/14 | (2006.01) |
| C07D 401/14 | (2006.01) |
| C07D 401/06 | (2006.01) |
| A61K 31/4439 | (2006.01) |
| A61K 31/444 | (2006.01) |

(52) U.S. Cl.
CPC ......... C07D 409/14 (2013.01); C07D 401/06 (2013.01); C07D 401/14 (2013.01); C07D 413/14 (2013.01); C07D 417/14 (2013.01)

(58) Field of Classification Search
None
See application file for complete search history.

(56) References Cited

U.S. PATENT DOCUMENTS

2009/0226398 A1* 9/2009 Leivers ............... C07D 487/04
424/85.4

FOREIGN PATENT DOCUMENTS

| WO | WO2008076805 A2 | 6/2008 |
|---|---|---|
| WO | WO2013093484 A1 | 6/2013 |
| WO | WO2014160592 A2 | 10/2014 |
| WO | 2016018701 A1 | 2/2016 |
| WO | WO2016018702 A1 | 2/2016 |

OTHER PUBLICATIONS

International Search Report and Written Opinion for PCT/CN2015/084937, dated Jul. 23, 2015, 16 pages.

* cited by examiner

*Primary Examiner* — Michael Barker
(74) *Attorney, Agent, or Firm* — Nicole M. Beeler; Catherine D. Fitch

(57) ABSTRACT

The present invention provides a compound of Formula (I) and pharmaceutical compositions comprising one or more said compounds, and methods for using said compounds for treating or preventing thromboses, embolisms, hypercoagulability or fibrotic changes. The compounds are selective Factor XIa inhibitors or dual inhibitors of Factor XIa and plasma kallikrein.

Formula I

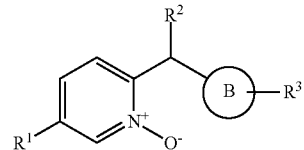

16 Claims, No Drawings

FACTOR XIA INHIBITORS

CROSS REFERENCE TO RELATED APPLICATIONS

This application is a U.S. National Phase application under 35 U.S.C. §371 of PCT Application No. PCT/CN2015/084937 filed Jul. 23, 2015, which claims priority from U.S. Provisional Application Ser. No. 62/029,758, filed Jul. 28, 2014.

BACKGROUND OF THE INVENTION

Factor XIa is a plasma serine protease involved in the regulation of blood coagulation. While blood coagulation is a necessary and important part of the regulation of an organism's homeostasis, abnormal blood coagulation can also have deleterious effects. For instance, thrombosis is the formation or presence of a blood clot inside a blood vessel or cavity of the heart. Such a blood clot can lodge in a blood vessel blocking circulation and inducing a heart attack or stroke. Thromboembolic disorders are the largest cause of mortality and disability in the industrialized world.

Blood clotting is a process of control of the blood stream essential for the survival of mammals. The process of clotting, and the subsequent dissolution of the clot after wound healing has taken place, commence after vascular damage, and can be divided into four phases. The first phase, vasoconstriction or vasocontraction, can cause a decrease in blood loss in the damaged area. In the next phase, platelet activation by thrombin, platelets attach to the site of the vessel wall damage and form a platelet aggregate. In the third phase, formation of clotting complexes leads to massive formation of thrombin, which converts soluble fibrinogen to fibrin by cleavage of two small peptides. In the fourth phase, after wound healing, the thrombus is dissolved by the action of the key enzyme of the endogenous fibrinolysis system, plasmin.

Two alternative pathways can lead to the formation of a fibrin clot, the intrinsic and the extrinsic pathway. These pathways are initiated by different mechanisms, but in the later phase they converge to give a common final path of the clotting cascade. In this final path of clotting, clotting factor X is activated. The activated factor X is responsible for the formation of thrombin from the inactive precursor prothrombin circulating in the blood. The formation of a thrombus on the bottom of a vessel wall abnormality without a wound is the result of the intrinsic pathway. Fibrin clot formation as a response to tissue damage or an injury is the result of the extrinsic pathway. Both pathways comprise a relatively large number of proteins, which are known as clotting factors. The intrinsic pathway requires the clotting factors V, VIII, IX, X, XI and XII and also prekallikrein, high molecular weight kininogen, calcium ions and phospholipids from platelets. The activation of factor XIa is a central point of intersection between the two pathways of activation of clotting. Factor XIa has an important role in blood clotting.

Coagulation is initiated when blood is exposed to artificial surfaces (e.g., during hemodialysis, "on-pump" cardiovascular surgery, vessel grafts, bacterial sepsis), on cell surfaces, cellular receptors, cell debris, DNA, RNA, and extracellular matrices. This process is also termed contact activation. Surface absorption of factor XII leads to a conformational change in the factor XII molecule, thereby facilitating activation to proteolytic active factor XII molecules (factor 25 XIIa and factor XIIf). Factor XIIa (or XIIf) has a number of target proteins, including plasma prekallikrein and factor XI. Active plasma kallikrein further activates factor XII, leading to an amplification of contact activation. Alternatively, the serine protease prolylcarboxylpeptidase can activate plasma kallikrein complexed with high molecular weight kininogen in a multiprotein complex formed on the surface of cells and matrices (Shariat-Madar et al., Blood, 108:192-199 (2006)). Contact activation is a surface mediated process responsible in part for the regulation of thrombosis and inflammation, and is mediated, at least in part, by fibrinolytic-, complement-, kininogen/kinin-, and other humoral and cellular pathways (for review, Coleman, R., "Contact ActivationPathway", Hemostasis and Thrombosis, pp. 103-122, Lippincott Williams & Wilkins (2001); Schmaier, A. H., "Contact Activation", Thrombosis and Hemorrhage, pp. 105-128 (1998)). The biological relevance of the contact activation system for thromboembolic 5 diseases is supported by the phenotype of factor XII deficient mice. More specifically, factor XII deficient mice were protected from thrombotic vascular occlusion in several thrombosis models as well as stroke models and the phenotype of the XII deficient mice was identical to XI deficient mice (Renne et al., J Exp. Med., 202:271-281 (2005); Kleinschmitz et al., J Exp. Med., 203:513-518 (2006)). The fact that factor XI is downstream from factor XIIa, combined with the identical phenotype of the XII and XI deficient mice suggest that the contact activation system could play a major role in factor XI activation in vivo.

Plasma kallikrein is a zymogen of a trypsin-like serine protease and is present in plasma. The gene structure is similar to that of factor XI. Overall, the amino acid sequence of plasma kallikrein has 58% homology to factor XI. Proteolyticactivation by factor XIIa at an internal I 389-R390 bond yields a heavy chain (371 amino acids) and a light chain (248 amino acids). The active site of plasma kallikrein is contained in the light chain. The light chain of plasma kallikrein reacts with protease 15 inhibitors, including alpha 2 macroglobulin and Cl-inhibitor. Interestingly, heparin significantly accelerates the inhibition of plasma kallikrein by antithrombin III in the presence of high molecular weight kininogen (HMWK). In blood, the majority of plasma kallikrein circulates in complex with HMWK. Plasma kallikrein cleaves HMWK to liberate bradykinin. Bradykinin release results in increase of vascular permeability andvasodilation (for review, Coleman, R., "Contact Activation Pathway", Hemostasis and Thrombosis, pp. 103-122, Lippincott Williams & Wilkins (2001); Schmaier A. H., "Contact Activation", Thrombosis and Hemorrhage, pp. 105-128 (1998)).

Patients presenting genetic deficiency on Cl-esterase inhibitor suffer from hereditary angioedema (HAE), a lifelong disease that results in intermittent swelling throughout the body, including the hands, feet, face, throat, genitals and gastrointestinal tract. Analysis of blisters arising from acute episodes have been shown to contain high levels of plasma kallikrein, and treatment with a protein-based reversible plasma kallikrein inhibitor, Ecallantide (Kalbitor), has been approved by the FDA for the treatment of acute attacks of HAE (Schneider, L, et al., J. Allergy Clin. Immunol., 120: p. 416 (2007)).

Additionally, the plasma kallikrein-kinin system is abnormally abundant in patients diagnosed with advanced diabetic macular edema (DME). Recent publications have shown that plasma kallikrein contributes to observed retinal vascular leakage and dysfunction in diabetic rodent models (A. Clermont, et al., Diabetes, 60:1590 (2011)), and that treatment with a small molecule plasma kallikrein inhibitor ameliorated the observed retinal vascular permeability and other abnormalities related to retinal blood flow.

Factor XIa inhibitor compounds are described in WO2014160592, WO2013022814, WO 2013022814, WO 2013022818, WO 2013055984, WO2013056034, WO2013056060, WO2013118805, WO2013093484, WO2002042273, WO2002037937, WO2002060894, WO2003015715, WO2004002405, US20040180855, WO2004080971, WO2004094372, US20050228000, US20050282805, WO2005123680, US20090036438, US20120088758, US20060074103, WO2006062972, WO2006076246, US20060154915, US20090062287, US20060183771, WO2007070818, WO2007070816, WO2007070826, WO2008076805, WO2008157162, WO2009114677, WO2011100402, and WO2011100401.

SUMMARY OF THE INVENTION

The present invention relates to compounds of Formula I:

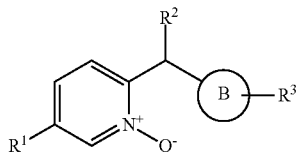

I or pharmaceutically acceptable salts thereof. The compounds of Formula I are selective Factor XIa inhibitors or dual inhibitors of Factor XIa and plasma kallikrein, and as such may be useful in the treatment, inhibition or amelioration of one or more disease states that could benefit from inhibition of Factor XIa or plasma kallikrein, including thromboses, embolisms, hypercoagulability or fibrotic changes. The compounds of this invention could further be used in combination with other therapeutically effective agents, including but not limited to, other drugs useful for the treatment of thromboses, embolisms, hypercoagulability or fibrotic changes. The invention furthermore relates to processes for preparing compounds of Formula I, and pharmaceutical compositions which comprise compounds of Formula I and pharmaceutically acceptable salts thereof.

DETAILED DESCRIPTION OF THE INVENTION

The present invention relates to compounds of Formula I:

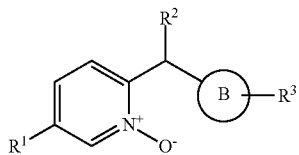

I wherein

is a 5 or 6 membered heteroaryl ring, wherein said heteroaryl ring is optionally substituted with one to three substituents independently selected from the group consisting of nitro, cyano, oxo, $R^a$, (C=O)$R^4$, (C=O)O$R^4$, N$R^4R^5$, NH(C=O)$R^4$, NH(C=O)O$R^4$, SO$_2R^4$, SO$_2$N$R^4R^5$, N$R^4$SO$_2R^5$ and PO$_3R^4$;

$R^1$ is aryl, heteroaryl, $C_{3-6}$ cycloalkyl or heterocyclyl, wherein said aryl, heteroaryl, cycloalkyl and heterocyclyl groups are optionally substituted with one to three substituents independently selected from the group consisting of halo, nitro, cyano, oxo, $R^4$, O$R^4$, (C=O)$R^4$, (C=O)O$R^4$, N$R^4R^5$, NH(C=O)$R^4$, NH(C=O)O$R^4$, $C_{3-6}$ cycloalkyl and heteroaryl which is optionally substituted with $R^4$;

$R^2$ is hydrogen or CH($R^{2a}$)($R^{2b}$);

$R^{2a}$ is hydrogen, $C_{1-6}$ alkyl, aryl, heteroaryl, $C_{3-6}$ cycloalkyl, heterocyclyl or (C=O)N$R^4R^5$, wherein said alkyl group is optionally substituted with one to three substituents independently selected from the group consisting of halo, hydroxy and cyano, and wherein said aryl, heteroaryl, cycloalkyl and heterocyclyl groups are optionally substituted with one to three substituents independently selected from the group consisting of halo, nitro, cyano, oxo, $R^4$ and O$R^4$;

$R^{2b}$ is hydrogen or $C_{1-6}$ alkyl, which is optionally substituted with one to three substituents independently selected from the group consisting of halo, hydroxy and cyano;

$R^3$ is halo, cyano, (C=O)O$R^4$ or $R^6$;

$R^4$ is hydrogen or $C_{1-6}$ alkyl, which is optionally substituted with one to three groups independently selected from the group consisting of halo and hydroxy;

$R^5$ is hydrogen or $C_{1-6}$ alkyl, which is optionally substituted with one to three groups independently selected from the group consisting of halo and hydroxy;

$R^6$ is aryl, heteroaryl, $C_{3-10}$ cycloalkyl or heterocyclyl, wherein said aryl, heteroaryl, cycloalkyl and heterocyclyl groups are optionally substituted with one to three substituents independently selected from the group consisting of halo, nitro, cyano, oxo, $R^4$, O$R^4$, (C=O)$R^4$, (C=O)O$R^4$, (C=O)N$R^4R^5$, N$R^4R^5$, NH(C=O)$R^4$, NH(C=O)O$R^4$, SO$_2R^4$, SO$_2$N$R^4R^5$, N$R^4$SO$_2R^5$ and PO$_3R^4$;

$R^a$ is hydrogen, halo, $R^4$ or O$R^4$;

or a pharmaceutically acceptable salt thereof.

An embodiment of the present invention relates to compounds of Formula Ia:

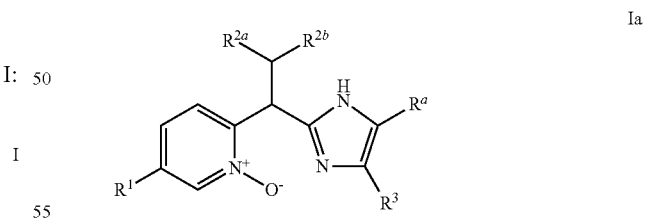

Ia wherein $R^1$ is aryl, heteroaryl, $C_{3-6}$ cycloalkyl or heterocyclyl, wherein said aryl, heteroaryl, cycloalkyl and heterocyclyl groups are optionally substituted with one to three substituents independently selected from the group consisting of halo, nitro, cyano, oxo, $R^4$, O$R^4$, (C=O)$R^4$, (C=O)O$R^4$, N$R^4R^5$, NH(C=O)$R^4$, NH(C=O)O$R^4$, $C_{3-6}$ cycloalkyl and heteroaryl which is optionally substituted with $R^4$;

$R^{2a}$ is hydrogen, $C_{1-6}$ alkyl, aryl, heteroaryl, $C_{3-6}$ cycloalkyl, heterocyclyl or (C=O)N$R^4R^5$, wherein said alkyl group is optionally substituted with one to three substituents independently selected from the group consisting of halo, hydroxy and cyano, and wherein said aryl, heteroaryl, cycloalkyl and heterocyclyl groups are optionally substituted with one to three substituents independently selected from the group consisting of halo, nitro, cyano, oxo, $R^4$ and $OR^4$;

$R^{2b}$ is hydrogen or $C_{1-6}$ alkyl, which is optionally substituted with one to three substituents independently selected from the group consisting of halo, hydroxy and cyano;

$R^3$ is halo, cyano, (C=O)$OR^4$ or $R^6$;

$R^4$ is hydrogen or $C_{1-6}$ alkyl, which is optionally substituted with one to three groups independently selected from the group consisting of halo and hydroxy;

$R^5$ is hydrogen or $C_{1-6}$ alkyl, which is optionally substituted with one to three groups independently selected from the group consisting of halo and hydroxy;

$R^6$ is aryl, heteroaryl, $C_{3-10}$ cycloalkyl or heterocyclyl, wherein said aryl, heteroaryl, cycloalkyl and heterocyclyl groups are optionally substituted with one to three substituents independently selected from the group consisting of halo, nitro, cyano, oxo, $R^4$, $OR^4$, (C=O)$R^4$, (C=O)$OR^4$, (C=O)$NR^4R^5$, $NR^4R^5$, NH(C=O)$R^4$, NH(C=O)$OR^4$, $SO_2R^4$, $SO_2NR^4R^5$, $NR^4SO_2R^5$ and $PO_3R^4$;

$R^a$ is hydrogen, halo, $C_{1-3}$ alkyl or O($C_{1-3}$ alkyl);

or a pharmaceutically acceptable salt thereof.

In an embodiment of the invention,

is a 5 membered heteroaryl ring. In a class of the invention,

is imidazolyl. In another embodiment of the invention,

is a 6 membered heteroaryl ring. In a class of the invention,

is pyridinyl. If the heteroaryl ring contains nitrogen atoms, it is understood that the corresponding N-oxides thereof are also encompassed.

In an embodiment of the invention, $R^1$ is aryl, which optionally is substituted with one to three substituents independently selected from the group consisting of halo, cyano, $R^4$, $OR^4$ and heteroaryl which is optionally substituted with $R^4$. In a class of the embodiment, $R^1$ is aryl, which optionally is substituted with one to three substituents independently selected from the group consisting of halo, cyano, $CHF_2$, $OCHF_2$, and heteroaryl. In a subclass of the embodiment, $R^1$ is phenyl, which optionally is substituted with one to two substituents independently selected from the group consisting of halo and tetrazolyl. In another subclass of the embodiment, $R^1$ is phenyl, which optionally is substituted with one to three halo.

In an embodiment of the invention, $R^2$ is hydrogen. In another embodiment of the invention, $R^2$ is CH($R^{2a}$)($R^{2b}$).

In an embodiment of the invention, $R^{2a}$ is aryl, which optionally is substituted with one to three halo. In a class of the embodiment, $R^{2a}$ is phenyl. In another class of the embodiment, $R^{2a}$ is phenyl which is substituted with halo. In another embodiment of the invention, $R^{2a}$ is $C_{3-8}$ cycloalkyl. In a class of the embodiment, $R^{2a}$ is cyclopropyl.

In an embodiment of the invention, $R^{2b}$ is hydrogen.

In an embodiment of the invention, $R^3$ is $R^6$. In a class of the embodiment, $R^3$ is $R^6$, which optionally is substituted with halo, (C=O)$OR^4$ or NH(C=O)$OR^4$.

In an embodiment of the invention, $R^6$ is aryl, which is optionally substituted with one to three substituents independently selected from the group consisting of halo, nitro, cyano, oxo, $R^4$, $OR^4$, (C=O)$R^4$, (C=O)$OR^4$, (C=O)$NR^4R^5$, $NR^4R^5$, NH(C=O)$R^4$, NH(C=O)$OR^4$, $SO_2R^4$, $SO_2NR^4R^5$, $NR^4SO_2R^5$ and $PO_3R^4$. In a class of the invention, $R^6$ is phenyl, which is optionally substituted with one to three substituents independently selected from the group consisting of halo, NH(C=O)$OR^4$ and (C=O)$OR^4$. In another embodiment of the invention, $R^6$ is heterocyyl, which is optionally substituted with one to three substituents independently selected from the group consisting of halo, nitro, cyano, oxo, $R^4$, $OR^4$, (C=O)$R^4$, (C=O)$OR^4$, (C=O)$NR^4R^5$, $NR^4R^5$, NH(C=O)$R^4$, NH(C=O)$OR^4$, $SO_2R^4$, $SO_2NR^4R^5$, $NR^4SO_2R^5$ and $PO_3R^4$.

In an embodiment of the invention, $R^a$ is hydrogen. In another embodiment of the invention, $R^a$ is halo.

The present invention also relates to compounds of Formula I:

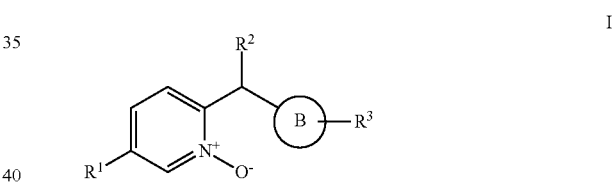

I wherein

is a 5 or 6 membered heteroaryl ring, wherein said heteroaryl is optionally substituted with one to three substituents independently selected from the group consisting of nitro, cyano, oxo, $R^a$, (C=O)$R^4$, (C=O)$OR^4$, $NR^4R^5$, NH(C=O)$R^4$, NH(C=O)$OR^4$, $SO_2R^4$, $SO_2NR^4R^5$, $NR^4SO_2R^5$ and $PO_3R^4$;

$R^1$ is aryl, heteroaryl, $C_{3-6}$ cycloalkyl or heterocyclyl, wherein said aryl, heteroaryl, cycloalkyl and heterocyclyl groups are optionally substituted with one to three substituents independently selected from the group consisting of halo, nitro, cyano, oxo, $R^4$, $OR^4$, (C=O)$R^4$, (C=O)$OR^4$, $NR^4R^5$, NH(C=O)$R^4$, NH(C=O)$OR^4$, C(NH)$NR^4R^5$, $C_{3-6}$ cycloalkyl and heteroaryl which is optionally substituted with $R^4$;

$R^2$ is hydrogen or CH($R^{2a}$)($R^{2b}$);

$R^{2a}$ is hydrogen, $C_{1-6}$ alkyl, aryl, heteroaryl, $C_{3-6}$ cycloalkyl, heterocyclyl or (C=O)$NR^4R^5$, wherein said alkyl group is optionally substituted with one to three substituents independently selected from the group consisting of halo, hydroxy and cyano, and wherein said aryl, heteroaryl, cycloalkyl and heterocyclyl groups are optionally substituted with one to three substituents independently selected from the group consisting of halo, nitro, cyano, oxo, $R^4$ and $OR^4$;

$R^{2b}$ is hydrogen or $C_{1-6}$ alkyl, which is optionally substituted with one to three substituents independently selected from the group consisting of halo, hydroxy and cyano;

$R^3$ is halo, cyano, (C=O)$OR^4$ or $R^6$;

$R^4$ is hydrogen or $C_{1-6}$ alkyl, which is optionally substituted with one to three groups independently selected from the group consisting of halo and hydroxy;

$R^5$ is hydrogen or $C_{1-6}$ alkyl, which is optionally substituted with one to three groups independently selected from the group consisting of halo and hydroxy;

$R^6$ is aryl, heteroaryl, $C_{3-10}$ cycloalkyl or heterocyclyl, wherein said aryl, heteroaryl, cycloalkyl and heterocyclyl groups are optionally substituted with one to three substituents independently selected from the group consisting of halo, nitro, cyano, oxo, $R^4$, $OR^4$, (C=O)$R^4$, (C=O)$OR^4$, (C=O)$NR^4R^5$, $NR^4R^5$, NH(C=O)$R^4$, NH(C=O)$OR^4$, $SO_2R^4$, $SO_2NR^4R^5$, $NR^4SO_2R^5$ and $PO_3R^4$;

$R^a$ is hydrogen, halo, $R^4$ or $OR^4$;

or a pharmaceutically acceptable salt thereof.

Reference to the preferred classes and subclasses set forth above is meant to include all combinations of particular and preferred groups unless stated otherwise.

Specific embodiments of the present invention include, but are not limited to the compounds identified herein as Examples 1 to 83, or pharmaceutically acceptable salts thereof.

Also included within the scope of the present invention is a pharmaceutical composition which is comprised of a compound of Formula I or Formula Ia as described above and a pharmaceutically acceptable carrier. The invention is also contemplated to encompass a pharmaceutical composition which is comprised of a pharmaceutically acceptable carrier and any of the compounds specifically disclosed in the present application. These and other aspects of the invention will be apparent from the teachings contained herein.

The invention also includes compositions for inhibiting loss of blood platelets, inhibiting formation of blood platelet aggregates, inhibiting formation of fibrin, inhibiting thrombus formation, inhibiting embolus formation, and treating inflammatory disorders in a mammal, comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

The invention also includes compositions for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compositions may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

Compounds of the invention are Factor XIa inhibitors and may have therapeutic value in, for example, preventing coronary artery disease. The compounds are selective Factor XIa inhibitors or dual inhibitors of Factor XIa and plasma kallikrein.

It will be understood that, as used herein, references to the compounds of structural Formula I and Formula Ia are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, digluconate, dihydrochloride, dodecylsulfanate, edetate, edisylate, estolate, esylate, ethanesulfonate, formic, fumarate, gluceptate, glucoheptanoate, gluconate, glutamate, glycerophosphate, glycollylarsanilate, hemisulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate, lactobionate, laurate, malate, maleate, mandelate, mesylate, methylbromide, methylnitrate, methylsulfate, methanesulfonate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, undeconate, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Also included are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

These salts can be obtained by known methods, for example, by mixing a compound of the present invention with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

If the compounds of Formula I or Formula Ia simultaneously contain acidic and basic groups in the molecule the invention also includes, in addition to the salt forms mentioned, inner salts or betaines (zwitterions).

The present invention encompasses all stereoisomeric forms of the compounds of Formula I and Formula Ia. Centers of asymmetry that are present in the compounds of Formula I and Formula Ia can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. When a particular configuration is depicted, that enantiomer (either (R) or (S), at that center) is intended. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or Formula Ia or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (including hydrates) and solvated salts of such racemates, enantiomers, diastereomers and tautomers and mixtures thereof.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the specifically and generically described compounds. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the general process schemes and examples herein using appropriate isotopically-enriched reagents and/or intermediates.

When any variable (e.g. $R^4$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off-target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted" (with one or more substituents) should be understood as meaning that the group in question is either unsubstituted or may be substituted with one or more substituents.

Furthermore, compounds of the present invention may exist in amorphous form and/or one or more crystalline forms, and as such all amorphous and crystalline forms and mixtures thereof of the compounds of Formula I and Formula Ia are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with un-solvated and anhydrous forms.

Reference to the compounds of this invention as those of a specific formula or embodiment, e.g., Formula I or Formula Ia or any other generic structural formula or specific compound described or claimed herein, is intended to encompass the specific compound or compounds falling within the scope of the formula or embodiment, including salts thereof, particularly pharmaceutically acceptable salts, solvates of such compounds and solvated salt forms thereof, where such forms are possible unless specified otherwise.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Examples of pharmaceutically acceptable pro-drug modifications include, but are not limited to, —C$_{1-6}$alkyl esters and —C$_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

Except where noted herein, the term "alkyl" is intended to include both branched- and straight-chain saturated aliphatic hydrocarbon groups having the specified number of carbon atoms. Commonly used abbreviations for alkyl groups are used throughout the specification, e.g. methyl, may be represented by conventional abbreviations including "Me" or CH$_3$ or a symbol that is an extended bond as the terminal group, e.g.

ethyl may be represented by "Et" or CH$_2$CH$_3$, propyl may be represented by "Pr" or CH$_2$CH$_2$CH$_3$, butyl may be represented by "Bu" or CH$_2$CH$_2$CH$_2$CH$_3$, etc. "C$_{1-4}$ alkyl" (or "C$_1$-C$_4$ alkyl") for example, means linear or branched chain alkyl groups, including all isomers, having the specified number of carbon atoms. For example, the structures

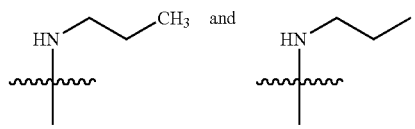

have equivalent meanings. C$_{1-4}$ alkyl includes n-, iso-, sec- and t-butyl, n- and isopropyl, ethyl and methyl. If no number is specified, 1-4 carbon atoms are intended for linear or branched alkyl groups.

Except where noted herein, "alkanol" is intended to include aliphatic alcohols having the specified number of carbon atoms, such as methanol, ethanol, propanol, etc., where the —OH group is attached at any aliphatic carbon, e.g., propan-1-ol, propan-2-ol, etc.

Except where noted, the term "cycloalkyl" means a monocyclic or bicyclic saturated aliphatic hydrocarbon group having the specified number of carbon atoms. For example, "cycloalkyl" includes cyclopropyl, cyclobutyl, cyclopentyl, cyclohexyl, and so on.

Except where noted, the term "halogen" or "halo" means fluorine, chlorine, bromine or iodine.

Except where noted, the term "heteroaryl", as used herein, represents a stable monocyclic or bicyclic ring system of up to 10 atoms in each ring, wherein at least one ring is aromatic, and at least one ring contains from 1 to 4 heteroatoms selected from the group consisting of O, N and S. Bicyclic heteroaryl ring systems include fused ring systems, where two rings share two atoms, and spiro ring systems, where two rings share one atom. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, methylenedioxybenzene, benzothiazolyl, benzothienyl, quinolinyl, isoquinolinyl, oxazolyl, tetrahydroquinoline and 3-oxo-3,4dihydro-2Nbenzo[b][1,4] thiazine. If the heteroaryl contains nitrogen atoms, it is understood that the corresponding N-oxides thereof are also encompassed by this definition.

Except where noted, the term "5 or 6 membered heteroaryl ring", as used herein, represents a stable monocyclic aromatic ring of 5 or 6 atoms, which contains from 1 to 4 heteroatoms selected from the group consisting of O, N and S. Heteroaryl groups within the scope of this definition include but are not limited to imidazolyl and pyridinyl.

Except where noted, the term "heterocycle" or "heterocyclyl" as used herein is intended to mean a stable nonaromatic monocyclic or bicyclic ring system of up to 10 atoms in each ring, unless otherwise specified, containing from 1 to 4 heteroatoms selected from the group consisting of O, N, S, SO, or SO$_2$. Bicyclic heterocyclic ring systems include fused ring systems, where two rings share two atoms, and spiro ring systems, where two rings share one atom. "Heterocyclyl" therefore includes, but is not limited to the following: piperazinyl, piperidinyl, pyrrolidinyl, morpholinyl, thiomorpholinyl, tetrahydropyranyl, dihydropiperidinyl, tetrahydrothiophenyl and the like. If the heterocycle contains a nitrogen, it is understood that the corresponding N-oxides thereof are also encompassed by this definition.

Except where noted, the term "aryl" is intended to mean any stable monocyclic or bicyclic carbon ring of up to 12 atoms in each ring, wherein at least one ring is aromatic. Examples of such aryl elements include phenyl, naphthyl, tetrahydronaphthyl and indanyl.

"Celite®" (Fluka) diatomite is diatomaceous earth, and can be referred to as "celite".

Except where noted herein, structures containing substituent variables such as variable "R" below:

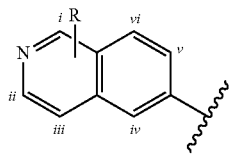

which are depicted as not being attached to any one particular bicyclic ring carbon atom, represent structures in which the variable can be optionally attached to any bicyclic ring carbon atom. For example, variable R shown in the above structure can be attached to any one of 6 bicyclic ring carbon atoms i, ii, iii, iv, v or vi.

Except where noted herein, bicyclic ring systems include fused ring systems, where two rings share two atoms, and spiro ring systems, where two rings share one atom.

The invention also includes derivatives of the compounds of Formula I and Formula Ia, acting as prodrugs and solvates. Prodrugs, following administration to the patient, are converted in the body by normal metabolic or chemical processes, such as through hydrolysis in the blood, to the compound of Formula 1 or Formula Ia. Such prodrugs include those that demonstrate enhanced bioavailability, tissue specificity, and/or cellular delivery, to improve drug absorption of the compound of Formula I or Formula Ia. The effect of such prodrugs may result from modification of physicochemical properties such as lipophilicity, molecular weight, charge, and other physicochemical properties that determine the permeation properties of the drug.

The preparation of pharmaceutically acceptable salts from compounds of the Formula I and Formula Ia capable of salt formation, including their stereoisomeric forms is carried out in a manner known per se. With basic reagents such as hydroxides, carbonates, hydrogencarbonates, alkoxides and ammonia or organic bases, for example, trimethyl- or triethylamine, ethanolamine, diethanolamine or triethanolamine, trometamol or alternatively basic amino acids, for example lysine, ornithine or arginine, the compounds of the Formula I and Formula Ia form stable alkali metal, alkaline earth metal or optionally substituted ammonium salts. If the compounds of the Formula I and Formula Ia have basic groups, stable acid addition salts can also be prepared using strong acids. For this, inorganic and organic acids such as hydrochloric, hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic or trifluoroacetic acid are suitable.

The invention also relates to medicaments containing at least one compound of the Formula I or Formula Ia and/or of a pharmaceutically acceptable salt of the compound of the Formula I or Formula Ia and/or an optionally stereoisomeric form of the compound of the Formula I or Formula Ia or a pharmaceutically acceptable salt of the stereoisomeric form of the compound of Formula I or Formula Ia, together with a pharmaceutically suitable and pharmaceutically acceptable vehicle, additive and/or other active substances and auxiliaries.

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, humans, sheep, horses, cattle, pigs, dogs, cats, rats, and mice.

Factor XIa or dual Factor XIa/plasma kallikrein inhibition are useful not only in the anticoagulant therapy of individuals having thrombotic conditions, but are useful whenever inhibition of blood coagulation is required such as to prevent coagulation of stored whole blood and to prevent coagulation in other biological samples for testing or storage. Thus, the Factor XIa or dual Factor XIa/plasma kallikrein inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems.

Compounds of the invention may be useful for treating or preventing venous thromboembolism (e.g., obstruction or occlusion of a vein by a detached thrombus; obstruction or occlusion of a lung artery by a detached thrombus), cardiogenic thromboembolism (e.g., obstruction or occlusion of the heart by a detached thrombus), arterial thrombosis (e.g., formation of a thrombus within an artery that may cause infarction of tissue supplied by the artery), atherosclerosis (e.g., arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention may be useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention may be useful for maintaining patency in arteriovenous cannulas.

Examples of atherosclerosis include arteriosclerosis.

The compounds of the invention may also be kallikrein inhibitors and especially useful for treatment of hereditary angioedema.

Examples of devices that come into contact with blood include vascular grafts, stents, orthopedic prosthesis, cardiac prosthesis, and extracorporeal circulation systems.

The medicaments according to the invention can be administered by oral, inhalative, rectal or transdermal administration or by subcutaneous, intraarticular, intraperitoneal or intravenous injection. Oral administration is preferred. Coating of stents with compounds of the Formula (I) and other surfaces which come into contact with blood in the body is possible.

The invention also relates to a process for the production of a medicament, which comprises bringing at least one compound of the Formula (I) into a suitable administration form using a pharmaceutically suitable and pharmaceutically acceptable carrier and optionally further suitable active substances, additives or auxiliaries.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or sesame oil, polyethylene glycol and solvents such as, for example, sterile water and mono- or polyhydric alcohols such as glycerol.

The dosage regimen utilizing the Factor XIa inhibitors or dual Factor XIa/plasma kallikrein inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the Factor XIa inhibitors or dual Factor XIa/plasma kallikrein inhibitors, when used for the indicated effects, will range between about 0.01 mg per kg of body weight per day (mg/kg/day) to about 30 mg/kg/day, preferably 0.025-7.5 mg/kg/day, more preferably 0.1-2.5 mg/kg/day, and most preferably 0.1-0.5 mg/kg/day (unless specified otherwise, amounts of active ingredients are on free base basis). For example, an 80 kg patient would receive between about 0.8 mg/day and 2.4 g/day, preferably 2-600 mg/day, more preferably 8-200 mg/day, and most preferably 8-40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the Factor XIa inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025-7.5 mg/kg/day, preferably 0.1-2.5 mg/kg/day, and more preferably 0.1-0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01-1.0 mg/mL, e.g. 0.1 mg/mL, 0.3 mg/mL, and 0.6 mg/mL, and administered in amounts per day of between 0.01 mL/kg patient weight and 10.0 mL/kg patient weight, e.g. 0.1 mL/kg, 0.2 mL/kg, 0.5 mL/kg. In one example, an 80 kg patient, receiving 8 mL twice a day of an intravenous formulation having a concentration of active ingredient of 0.5 mg/mL, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. The choice of appropriate buffer and pH of a formulation, depending on solubility of the drug to be administered, is readily made by a person having ordinary skill in the art.

Compounds of the Formula I and Formula Ia can be administered both as a monotherapy and in combination with other therapeutic agents, including antithrombotics (anticoagulants and platelet aggregation inhibitors), thrombolytics (plasminogen activators), other profibrinolytically active substances, hypotensives, blood sugar regulators, lipid-lowering agents and antiarrhythmics.

The Factor XIa inhibitors or dual Factor XIa/plasma kallikrein inhibitors can also be co-administered with suitable anticoagulants, including, but not limited to, other Factor XIa inhibitors, thrombin inhibitors, thrombin receptor antagonists, factor VIIa inhibitors, factor Xa inhibitors, factor IXa inhibitors, factor XIIa inhibitors, adenosine diphosphate antiplatelet agents (e.g., P2Y12 antagonists), fibrinogen receptor antagonists (e.g. to treat or prevent unstable angina or to prevent reocclusion after angioplasty and restenosis), other anticoagulants such as aspirin, and thrombolytic agents such as plasminogen activators or streptokinase to achieve synergistic effects in the treatment of various vascular pathologies. Such anticoagulants include, for example, apixaban, dabigatran, cangrelor, ticagrelor, vorapaxar, clopidogrel, edoxaban, mipomersen, prasugrel, rivaroxaban, and semuloparin. For example, patients suffering from coronary artery disease, and patients subjected to angioplasty procedures, would benefit from coadministration of fibrinogen receptor antagonists and thrombin inhibitors. Factor XIa inhibitors may be administered first following thrombus formation, and tissue plasminogen activator or other plasminogen activator is administered thereafter.

Alternatively or additionally, one or more additional pharmacologically active agents may be administered in combination with a compound of the invention. The additional active agent (or agents) is intended to mean a pharmaceutically active agent (or agents) that is active in the body, including pro-drugs that convert to pharmaceutically active form after administration, which is different from the compound of the invention, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of the invention in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme inhibitors (e.g. alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); angiotensin II receptor antagonists also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®), etc.); potassium sparing diuretics such as amiloride HCl, spironolactone, eplerenone, triamterene, each with or without HCTZ; neutral endopeptidase inhibitors (e.g., thiorphan and phosphoramidon); aldosterone antagonists; aldosterone synthase inhibitors; renin inhibitors; enalkrein; RO 42-5892; A 65317; CP 80794; ES 1005; ES 8891; SQ 34017; aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazosin, prazosin or alpha methyldopa); central alpha adrenergic agonists; peripheral vasodilators (e.g. hydralazine); lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; inhibitors of glucose uptake, such as sodium-glucose transporter (SGLT) inhibitors and its various isoforms, such as SGLT-1, SGLT-2 (e.g., ASP-1941, TS-071, BI-10773, tofogliflozin, LX-4211, canagliflozin, dapagliflozin, ertugliflozin, ipragliflozin and remogliflozin), and SGLT-3; or with other drugs beneficial for the prevention or the treatment of the above-mentioned diseases including but not limited to diazoxide; and including the free-acid, free-base, and pharmaceutically acceptable salt forms, pro-drug forms, e.g., esters, and salts of pro-drugs of the above medicinal agents, where chemically possible. Trademark names of pharmaceutical drugs noted above are provided for exemplification of the marketed form of the active agent(s); such pharmaceutical drugs could be used in a separate dosage form for concurrent or sequential administration with a compound of the invention, or the active agent(s) therein could be used in a fixed dose drug combination including a compound of the invention.

Typical doses of Factor XIa inhibitors or Factor XIa/plasma kallikrein inhibitors of the invention in combination with other suitable anti-platelet agents, anticoagulation agents, or thrombolytic agents may be the same as those doses of Factor XIa inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic needs.

The compounds are administered to a mammal in a therapeutically effective amount. By "therapeutically effective amount" it is meant an amount of a compound of the present invention that, when administered alone or in combination with an additional therapeutic agent to a mammal, is effective to treat (i.e. prevent, inhibit or ameliorate) the thromboembolic and/or inflammatory disease condition or treat the progression of the disease in a host.

The compounds of the invention are preferably administered alone to a mammal in a therapeutically effective amount. However, the compounds of the invention can also be administered in combination with an additional therapeutic agent, as defined below, to a mammal in a therapeutically effective amount. When administered in a combination, the combination of compounds is preferably, but not necessarily, a synergistic combination. Synergy, as described for example by Chou and Talalay, *Adv. Enzyme Regul.* 1984, 22, 27-55, occurs when the effect (in this case, inhibition of the desired target) of the compounds when administered in combination is greater than the additive effect of each of the compounds when administered individually as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The present invention is not limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claims.

For purposes of this specification, the following abbreviations have the indicated meanings:

For purposes of this specification, the following abbreviations have the indicated meanings:

LIST OF ABBREVIATIONS

ACN=acetonitrile
AcOH or HOAc=acetic acid
aq=aqueous
Cbz=carboxybenzyl
DAST=diethylaminosulfur trifluoride
DMF=dimethylformamide
DCM=dichloromethane
DIPEA=N,N-Diisopropylethylamine
EtOAc=ethyl acetate
EtOH=ethanol
h or hr=hour
Hex=Hexanes
HPLC=High Pressure Liquid Chromatography
RP HPLC=Reverse Phase
LCMS=Liquid chromatography-mass spectrometry
LDA=lithium diisoproylamide
LHMDS=lithium hexamethyldisilazide
LiOH=lithium hydroxide
Me=methyl
MeOH=methanol
min=minute
MS=mass spectrometry
mCPBA=meta-chloroperoxybenzoic acid
NBS=N-bromosuccinimide
NCS=N-chlorosuccinimide
PdCl$_2$(dppf)=[1,1'-bis(diphenylphosphino)ferrocene]dichloropalladium(II),
rt or RT=room temperature
THF=tetrahydrofuran
sat or satd=saturated
SEM=2-(trimethylsilyl)ethoxymethyl
SFC=supercritical fluid chromatography
SM=Starting material
TFA=Trifluoroacetic acid
Vac=Vacuum
HATU=2-(1H-7-Azabenzotriazol-1-yl)-1,1,3,3-tetramethyluronium hexafluorophosphate Methanaminium Also, TLC is thin layer chromatography; Ts is tosyl; UV is ultraviolet; W is watts; wt. % is percentage by weight; x g is times gravity; $\alpha_D$ is the specific rotation of polarized light at 589 nm; ° C. is degrees Celsius; % w/v is percentage in weight of the former agent relative to the volume of the latter agent.

"F11a IC50" is Factor XIa IC50 and "PK IC50" is Plasma Kallekrein IC50.

LCMS conditions: column: SUPELCO Ascentis Express C18 3×100 mm, 2.7 μm. Solvent system: A—0.05% TFA in water and B—0.05% TFA in Acetonitrile. Gradient condition: 10% B to 99% B in 3.5 min.

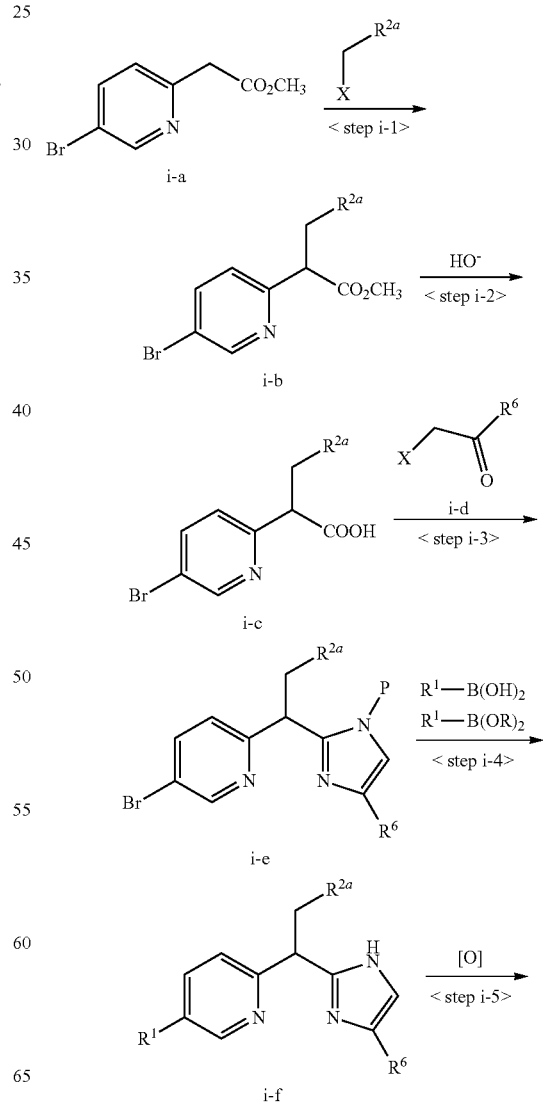

-continued

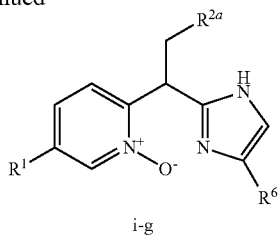

i-g

<Step i-1>

A compound represented by formula (i-b) can be produced by allowing the commercially available (i-a) to react with a properly substituted alkylating reagent such as an alkylhalide, an alkylmethanasulfonate, or an alkyl-p-toluenesulfonate by a well-known process or a process similar to that described in published documents (For example, Hajri, Majdi; Blondelle, Clement; Martinez, Agathe; Vasse, Jean-Luc; Szymoniak, Jan Tetrahedron Letters (2013), 54(8), 1029-1031), in the presence of a base such as LHMDS, lithium diisopropylamide (LDA), or sodium hydride in a solvent which is inactive to the reaction such as tetrahydrofuran or toluene at a temperature in the range of −78° C. to room temperature.

<Step i-2>

A compound represented by formula (i-c) can be produced by allowing the suitably substituted (i-b) to react with an inorganic or organic base such as lithium hydroxide, sodium hydroxide, or sodium tert-butoxide by a well-known process or a process similar to that described in published documents (For example, Huang, Hanmin; Xia, Chungu; Xie, Pan, Ger. Offen. (2013), DE 102012224021 A1 Nov. 14, 2013) in an aqueous solvent containing water and an organic co-solvent such as methanol, acetonitrile, and tetrahydrofuran.

<Step i-3>

A compound represented by formula (i-e) can be produced by allowing acid (i-c) to react with a beta-ketohalide represented by formula (i-d) by a a process similar to that described in published documents (For example, PCT Int. Appl. WO 2007070826 A1), in the presence of an inorganic or organic base such as cesium carbonate ($Cs_2CO_3$), potassium carbonate ($K_2CO_3$), potassium tert-butoxide (KO-tBu), followed by an amine source such as ammonium acetate in a solvent which is inactive to the reaction, such as a halogenated solvent, e.g., dichloromethane or chloroform, an ethereal solvent, e.g., diethyl ether or tetrahydrofuran, an aromatic hydrocarbon solvent, e.g., toluene or benzene, a polar solvent, e.g., N,N-dimethylformamide, or an alcoholic solvent, e.g., methanol, ethanol, or 2-propanol, at a temperature in the range of 0° C. to 150° C. Upon completion of cyclization, the reaction mixture is generally treated with an acylating or alkylating agent represented by formula P—X where P is a protection group and X is a halogen. Typical reagents in the form of P—X include (2-chloromethoxyethyl)trimethylsilane, chloromethyl 2-trimethylsilylethyl ether (SEM-Cl), toluene sulfonyl chloride, and benzyl chloroformate (Cbz-Cl).

<Step i-4>

A compound represented by formula (i-f) can be produced by a method commonly referred to as the Suzuki coupling reaction. Compounds of type (i-f) can be treated with an aryl- or heteroaryl-boronic acid of type $R^1$—$B(OH)_2$, or alternatively, an aryl- or heteroarylboronate of type $R^1$—B$(OR)_2$, in the presence of a suitable palladium catalyst, such as [1,1'-bis(diphenylphosphino)ferrocene]-dichloropalladium(II), or tetrakis(triphenylphosphine)palladium (0), or the like, and a mild base, such as sodium carbonate, sodium phosphate tribasic, or the like (Pure Appl. Chem. 1991, 63, 419-422). The reaction is usually performed in a suitable degassed aqueous mixture of inert organic solvents, such as toluene, ethanol or dioxane, at elevated temperatures, generally between 70° C. and the boiling temperature of the solvent mixture, for a period of 3-24 h. Alternatively, those skilled in the art can perform the Suzuki reaction described above in a suitable vessel that enables heating in a microwave reactor to superheated reaction temperatures that can reduce reaction times to between 1 min and 1 h. Recently, conditions suitable for performing Suzuki reactions at room temperature have been published (For example, see: J. Am. Chem. Soc. 2000, 122, 4020-4028, and references therein).

<Step i-5>

A compound represented by formula (i-g) can be produced by allowing the suitably substituted pyridine amide (i-f) to react with an oxidizing reagent commonly referred to as a peroxide, such as hydrogen peroxide, mCPBA, oxone, dimethyldioxirane, and peracetic acid in a proper solvent including water, methylene chloride or acetic acid. The reaction is usually performed at a temperature between 0° to 70° C. in a time period ranging from a few minutes to a few days. Such a process or processes similar to that are described in published documents (For example, see, Deng, Lisheng; Sundriyal, Sandeep; Rubio, Valentina; Shi, Zhengzheng; Song, Yongcheng, Journal of Medicinal Chemistry (2009), 52(21), 6539-6542).

SCHEME 2

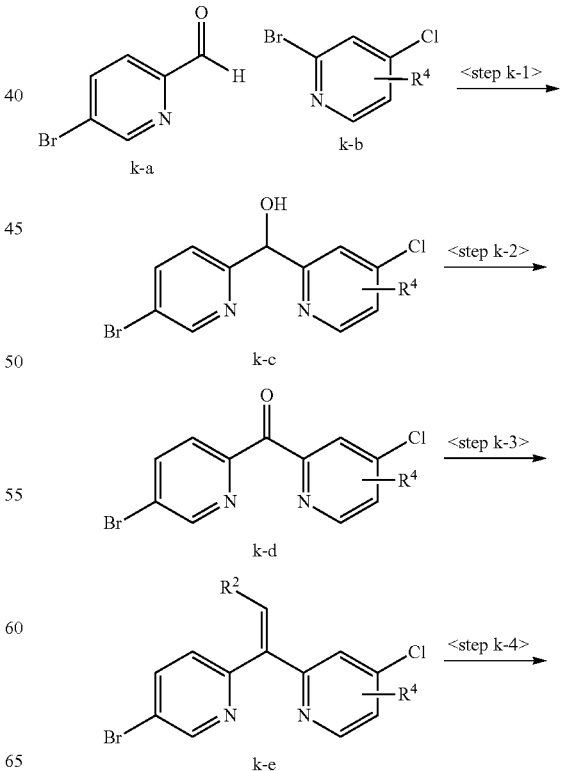

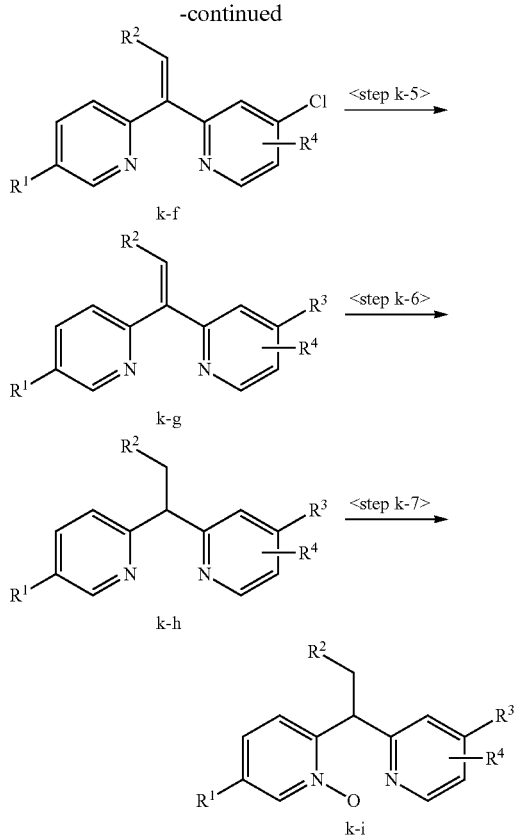

<Step k-1>

A compound represented by formula (k-c) can be produced by allowing the commercially available k-a and k-b to react by a well-known process or a process similar to that described in published documents (For example, J. Org. Chem. 2004, 69, 250-262), in the presence of a base such as n-butyllithium, LHMDS, or lithium diisopropylamide (LDA), in a solvent which is inactive to the reaction such as tetrahydrofuran or toluene at a temperature in the range of −78° C. to room temperature.

<Step k-2>

A compound represented by formula (k-d) can be produced by allowing the suitably substituted (k-c) to react with an oxidazing agent such as manganese dioxide ($MnO_2$), potassium permanganate ($KMnO_4$) or selenium dioxide ($SeO_2$) by a well-known process or a process similar to that described in published documents (For example, J. Org. Chem. 2004, 69, 250-262.) in an solvent containing water and an organic co-solvent such as methanol, acetonitrile, and tetrahydrofuran.

<Step k-3>

A compound represented by formula (k-e) can be produced by a method commonly referred to as Wittig reaction conditions. Compounds of type (k-d) can be treated with a properly substituted Wittig reagent such as benzylchlorotriphenylphosphorane following a well-known process or a process similar to that described in published documents (for example, WO 2011/034849, PCT/US2010/048764) in the presence of a based such as LHMDS or n-butyllithium in a solvent in a solvent which is inactive to the reaction such as tetrahydrofuran or toluene at a temperature in the range of −78° C. to room temperature.

<Step k-4> and <Step k-5>

A compound represented by formula (k-e and k-f) can be produced by a method commonly referred to as the Suzuki coupling reaction. Compounds of type (k-d) can be treated with an aryl- or heteroaryl-boronic acid of type $R^1$—B$(OH)_2$, or alternatively, an aryl- or heteroarylboronate of type $R^1$—B$(OR)_2$, in the presence of a suitable palladium catalyst, such as [1,1'-bis(diphenylphosphino)ferrocene]-dichloropalladium(II), or tetrakis(triphenylphosphine) palladium (0), or the like, and a mild base, such as sodium carbonate, sodium phosphate tribasic, or the like (*Pure Appl. Chem.* 1991, 63, 419-422). The reaction is usually performed in a suitable degassed aqueous mixture of inert organic solvents, such as toluene, ethanol or dioxane, at elevated temperatures, generally between 70° C. and the boiling temperature of the solvent mixture, for a period of 3-24 h. Alternatively, those skilled in the art can perform the Suzuki reaction described above in a suitable vessel that enables heating in a microwave reactor to superheated reaction temperatures that can reduce reaction times to between 1 min and 1 h. Recently, conditions suitable for performing Suzuki reactions at room temperature have been published (for example, see: *J. Am. Chem. Soc.* 2000, 122, 4020-4028, and references therein).

<Step k-6>

A compound represented by formula (k-f) can be produced by subjecting the suitably substituted (k-e) to general hydrogenation conditions well know to those skill in the art, such as the well-known process described in published documents (For example, WO 2011/034849, PCT/US2010/048764.)

<Step k-7>

A compound represented by formula (k-g) can be produced by allowing the suitably substituted pyridine amide (k-f) to react with an oxidizing reagent commonly referred to as a peroxide, such as hydrogen peroxide, mCPBA, oxone, dimethyldioxirane, and peracidic acid in a proper solvent including water, methylene chloride or acetic acid. The reaction is usually performed at a temperature between 0° to 70° C. in a time period ranging from a few minutes to a few days. Such a process or processes similar to that are described in published documents (For example, see, Deng, Lisheng; Sundriyal, Sandeep; Rubio, Valentina; Shi, Zhengzheng; Song, Yongcheng, Journal of Medicinal Chemistry (2009), 52(21), 6539-6542).

INTERMEDIATES methyl (4-(2-bromoacetyl)phenyl)carbamate

Step 1: methyl (4-acetylphenyl)carbamate

Methyl carbonochloridate (3.58 ml, 46.2 mmol) was dropped to a solution of 1-(4-aminophenyl)ethanone (5.0 g, 37.0 mmol) and pyridine (4.49 ml, 55.5 mmol) in $CH_2Cl_2$ (100 ml) at 0° C. and the mixture was stirred at 0° C. for 30 min. Then, the ice-bath was removed and the reaction was run at RT for 90 min. The solvent was removed under reduced pressure and the residue was purified by flash chromatography on a silica-gel column with 0-45% EtOAc/hexane to give the title compound. MS (ESI) m/z 194.10 (M+H).

Step 2: methyl (4-(2-bromoacetyl)phenyl)carbamate

Bromine (0.850 ml, 16.50 mmol) was dropped slowly to a suspension of methyl (4-acetylphenyl)carbamate (2.90 g, 15 mmol) in CHCl$_3$ (100 ml) at rt. The reaction was stirred and monitored by LCMS. After 18 h, the solvent was removed under reduced pressure and the residue was taken up in MeOH/CH$_2$Cl$_2$ (30 ml, 6:1) and stirred for 15 min. The solid was filtered, washed with 5 ml of CH$_2$Cl$_2$ and dried in vacuum to give the title compound. MS (ESI) m/z 274.00 (M+H).

methyl (4-(2-bromoacetyl)-3-methylphenyl)carbamate

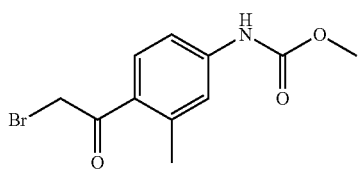 [SMILES: COC(=O)Nc1ccc(C(=O)CBr)c(C)c1]

Step 1: methyl (4-acetyl-3-methylphenyl)carbamate 1-(4-Amino-2-methylphenyl)ethanone was used as starting material for the synthesis of methyl (4-acetyl-3-methylphenyl)carbamate by following the same procedure as step 1 for synthesis of methyl (4-acetylphenyl)carbamate. The reaction gave the title compound. MS (ESI) m/z 208.06 (M+H).

Step 2: methyl (4-(2-bromoacetyl)-3-methylphenyl)carbamate

Phenyltrimethylaminonium tribromide (1.0 g, 2.65 mmol) was added to a solution of methyl (4-acetyl-3-methylphenyl) carbamate (0.5 g, 2.41 mmol) in THF (15 ml) at RT, followed by stirring at RT overnight. The mixture was filtered and washed with THF. The filtrate was concentrated and the residue was purified by a flash chromatography on a silica-gel column with 0-55% EtOAc/hexane to give the title compound. MS (ESI) m/z 285.99 (M+H).

methyl (4-(2-bromoacetyl)-3-fluorophenyl)carbamate

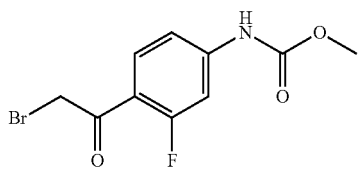 [SMILES: COC(=O)Nc1ccc(C(=O)CBr)c(F)c1]

Step 1: methyl (4-acetyl-3-fluorophenyl)carbamate 1-(4-Amino-2-fluorophenyl)ethanone was used as starting material for the synthesis of methyl (4-acetyl-3-fluorophenyl)carbamate by following the same procedure as step 1 for the synthesis of methyl (4-acetylphenyl)carbamate. The reaction gave the title compound. MS (ESI) m/z 212.03 (M+H).

Step 2: methyl (4-(2-bromoacetyl)-3-fluorophenyl)carbamate

Methyl (4-acetyl-3-fluorophenyl)carbamate was used as starting material for the synthesis of methyl (4-(2-bromoacetyl)-3-fluorophenyl)carbamate by following the same procedure as step 2 for the synthesis of methyl (4-(2-bromoacetyl)phenyl)carbamate. The reaction took 3 h and gave the title compound. MS (ESI) m/z 292.01 (M+H).

methyl (4-(2-bromoacetyl)-3-chlorophenyl)carbamate

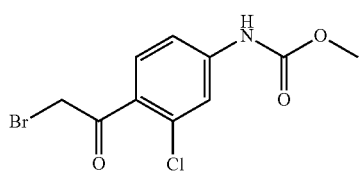 [SMILES: COC(=O)Nc1ccc(C(=O)CBr)c(Cl)c1]

Step 1: methyl (4-acetyl-3-chlorophenyl)carbamate 1-(4-Amino-2-chlorophenyl)ethanone was used as starting material for the synthesis of methyl (4-acetyl-3-chlorophenyl)carbamate by following the same procedure as step 1 for the synthesis of methyl (4-acetylphenyl)carbamate. The reaction gave the title compound. MS (ESI) m/z 227.96 (M+H).

Step 2: methyl (4-(2-bromoacetyl)-3-chlorophenyl)carbamate methyl (4-acetyl-3-chlorophenyl)carbamate was used as starting material for the synthesis of methyl (4-(2-bromoacetyl)-3-chlorophenyl)carbamate by following the same procedure as step 2 for the synthesis of methyl (4-(2-bromoacetyl)phenyl)carbamate. The reaction was run at RT for 3 h and the mixture was concentrated under reduced pressure and the residue was purified by a flash chromatographt on a silica-gel column with 0-45% EtOAc/hexane to give the title compound. MS (ESI) m/z 307.96 (M+H).

Isopropyl (4-(2-bromoacetyl)phenyl)carbamate

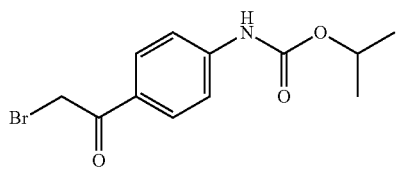 [SMILES: CC(C)OC(=O)Nc1ccc(C(=O)CBr)cc1]

Step 1: Isopropyl (4-acetylphenyl)carbamate 1-(4-Aminophenyl)ethanone was used as starting material for the synthesis of isopropyl (4-acetylphenyl)carbamate by following the same procedure as step 1 for the synthesis of methyl (4-acetylphenyl)carbamate. The reaction gave the title compound. MS (ESI) m/z 222.00 (M+H).

Step 2: Isopropyl (4-(2-bromoacetyl)phenyl)carbamate

Isopropyl (4-acetylphenyl)carbamate was used as starting material for the synthesis of isopropyl (4-(2-bromoacetyl)phenyl)carbamate by following the same procedure as step 2 for the synthesis of methyl (4-(2-bromoacetyl)phenyl)carbamate. The reaction gave the title compound. MS (ESI) m/z 301.92 (M+H).

methyl-d3 (4-(2-bromoacetyl)phenyl)carbamate

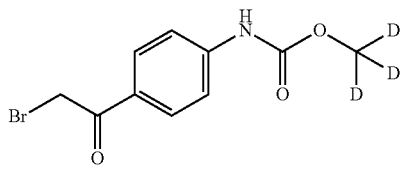 [SMILES: [2H]C([2H])([2H])OC(=O)Nc1ccc(C(=O)CBr)cc1]

Step 1: methyl-d3 (4-acetylphenyl)carbamate

A solution of D4-methanol (1.05 g, 30.0 mmol) and Hunig's Base (5.24 ml, 30.0 mmol) in CH$_2$Cl$_2$ (30 ml) was dropped into a solution of bis(trichloromethyl) carbonate (3.71 g, 12.50 mmol) in CH$_2$Cl$_2$ (30 ml) at –10° C. The temperature was maintained ~–10° C. and it was stirred for 20 min. To it was added a solution of 1-(4-aminophenyl)ethanone (1.35 g, 10 mmol) in CH$_2$Cl$_2$ (30 ml) and it was stirred for 2 h while the temperature was raised up to 0° C. The reaction mixture was washed with water. The organic phase was dried over MgSO$_4$, filtered, concentrated under reduced pressure and purified by column chromatography on silica gel (Teledyne ISCO Si; 40 gram prepacked) and eluting with 0-60% EtOAc/hexane to give methyl-d3 (4-acetylphenyl)carbamate.

Step 2: methyl-d3 (4-(2-bromoacetyl)phenyl)carbamate

Bromine (0.19 ml, 3.77 mmol) was dropped into a suspension of methyl-d3 (4-acetylphenyl)carbamate (0.74 g, 3.77 mmol) in CHCl$_3$ (20 ml) at rt. The reaction was stirred and monitored by LCMS. After 60 min., the mixture was concentrated under reduced pressure and the residue was washed with CH$_2$Cl$_2$ (5 ml) and dried in vacuo to give the title compound.

Methyl 4-(2-bromoacetyl)-3-fluorothiophene-2-carboxylate

Step 1: Methyl 4-acetyl-3-fluorothiophene-2-carboxylate

To a solution of methyl 4-bromo-3-fluorothiophene-2-carboxylate (5.0 g, 20.92 mmol) in dioxane (50 ml) were added tributyl(1-ethoxyvinyl)tin (7.06 ml, 20.92 mmol) and tetrakis (1.208 g, 1.046 mmol). The reaction mixture was stirred under N$_2$ at 95° C. for 8 h. The reaction was monitored by LCMS. The reaction was quenched with sat. KF (50 mL) and stirred at 26° C. for 1 h. Then, the mixture was filtered and the filtrate was concentrated under reduced pressure. The residue was dissolved in THF (50 mL) and 1M HCl (50 mL) was added. The mixture was stirred at rt for another 1 h and then extracted with EtOAc (3×50 mL). The combined organic phases were dried over Na$_2$SO$_4$, and concentrated in vacuo. The residue was purified by column chromatography (prepacked silica-gel column), eluting with 0-30% EtOAc/hexane to give the title compound. MS (ESI) m/z 202.91 (M+H).

Step 2: Methyl 4-(2-bromoacetyl)-3-fluorothiophene-2-carboxylate

To a solution of methyl 4-acetyl-3-fluorothiophene-2-carboxylate (2.01 g, 9.94 mmol) in THF (50 ml) was added pyridinium tribromide (3.18 g, 9.94 mmol), followed by stirring at RT for 8 h. TLC showed little starting material remained and a new spot formed. The reaction was quenched with H$_2$O (40 mL) and extracted with EtOAc (3×50 mL). The combined organic phases were dried over Na$_2$SO$_4$, and concentrated in vacuo. The residue was purified by column chromatography (prepacked silica-gel column), eluting with 0-20% EtOAc/hexane to give the title compound. MS (ESI) m/z 280.16 (M+H).

methyl 3-(2-bromoacetyl)-2-fluorobenzoate

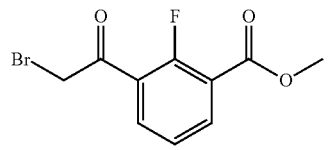

Step 1: methyl 3-(1-ethoxyvinyl)-2-fluorobenzoate

To a mixture of methyl 3-bromo-2-fluorobenzoate (4.5 g, 19.31 mmol) and tributyl(1-ethoxyvinyl)stannane (6.49 mL, 19.31 mmol) in dioxane (80 mL) was added Pd(Ph$_3$P)$_4$ (2.231 g, 1.931 mmol), and the mixture was stirred at 90° C. for 12 h. TLC indicated that the reaction was complete. The mixture was diluted with water (200 mL) and extracted with EtOAc (200 mL×3). The combined organic layers were washed with brine (200 mL), dried over anhydrous sodium sulfate, filtered, and concentrated in a vacuum to give the title compound, which was used in the next step without further purification.

Step 2: methyl 3-(2-bromoacetyl)-2-fluorobenzoate

To a solution of methyl 2-(1-ethoxyvinyl)-3-fluorobenzoate (2.5 g, 11.15 mmol) in THF (50 mL) and water (10 mL) was added NBS (2.381 g, 13.38 mmol) at 20° C. The reaction mixture was stirred at 20° C. for 16 h. TLC showed the reaction was complete. The reaction mixture was filtered and the filtrate was concentrated, and the residue was purified by silica gel gradient chromatography (SiO$_2$, PE:EtOAc=3:1) to give the title compound. $^1$H NMR (CDCl$_3$, 400 MHz): 8.12-8.20 (m, 1H), 8.05-8.11 (m, 1H), 7.34 (t, J=7.8 Hz, 1H), 4.53 (d, J=2.3 Hz, 2H), 3.95 (s, 3H).

2-(5-bromopyridin-2-yl)-3-(1-methylcyclopropyl)propanoate

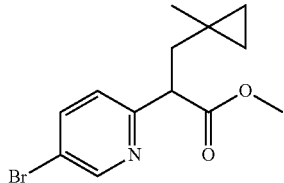 [SMILES: COC(=O)C(CC1(C)CC1)c1ccc(Br)cn1]

Step 1: methyl 2-(5-bromopyridin-2-yl)-4-methylpent-4-enoate

To a solution of methyl 2-(5-bromopyridin-2-yl)acetate (10 g, 43.5 mmol) in THF (150 mL) was added lithium bis(trimethylsilyl)amide (56.5 mL, 56.5 mmol) dropwise at −78° C. After stirring at −78° C. for 30 min, 3-bromo-2-methylprop-1-ene (4.60 mL, 45.6 mmol) was added to the reaction mixture. The mixture was warmed to 20° C. and stirred at 20° C. for 1 h under a N$_2$ atmosphere. TLC showed the reaction was complete. The reaction was quenched with sat. NH$_4$Cl (80 mL) and extracted with EtOAc (3×80 mL). The combined organic phases were dried over anhydrous sodium sulfate and concentrated to give the title compound. MS (ESI) m/z 286.0 (M+H).

Step 2: methyl 2-(5-bromopyridin-2-yl)-3-(1-methylcyclopropyl)propanoate

To a solution of diethylzinc (282 mL, 282 mmol) in DCM (50 mL) was added diiodomethane (22.70 mL, 282 mmol) at 0° C. After stirring at the same temperature for 30 min, a solution of methyl 2-(5-bromopyridin-2-yl)-4-methylpent-4-enoate (8 g, 28.2 mmol) in DCM (10 mL) was added. The mixture was stirred at 25° C. for 13 h under N$_2$ atmosphere. The mixture was quenched with sat. NH$_4$Cl (100 mL) and filtered. The filtrate was extracted with DCM (100 mL×2), dried over sodium sulfate and concentrated. The residue was purified by prep-HPLC (neutral method) to give the title compound. MS (ESI) m/z 299.8 (M+H).

2-bromo-4-chloro-1-(difluoromethyl)-3-fluorobenzene

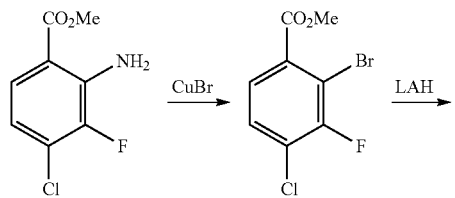

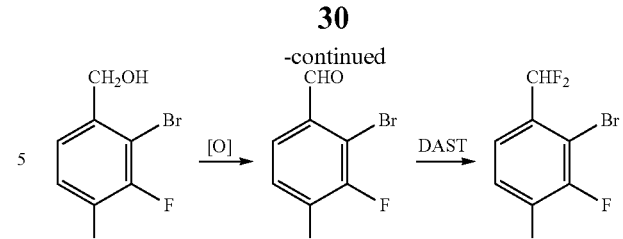

Step 1: Methyl 2-bromo-4-chloro-3-fluorobenzoate

Methyl 2-amino-4-chloro-3-fluorobenzoate (250 mg, 1.23 mmol) was added in one portion to a stirred suspension of copper(II)bromide (329 mg, 1.47 mmol) and tert-butyl nitrite (219 μL, 1.84 mmol) in acetonitrile (8.2 mL) at 0° C. The resulting reaction mixture was allowed to stir for 1 h, at which point the reaction mixture was partitioned between EtOAc and 0.05M HCl. The layers were separated, and the aq. layer was extracted with EtOAc. The combined organics were washed with brine, dried (Na$_2$SO$_4$), filtered and concentrated to afford a crude product that was purified by flash chromatography on silica gel (isocratic elution; 50% EtOAc/hexanes as eluent) to afford the title compound. m/z (ES) 267 (MH)$^+$.

Step 2: Preparation of (2-bromo-4-chloro-3-fluorophenyl)methanol

Lithium borohydride (LAH) (20 mg, 0.92 mmol) was added to a stirred solution of methyl 2-bromo-4-chloro-3-fluorobenzoate (120 mg, 0.45 mmol) in THF (4.5 mL) at 0° C. After 20 min, the cooling bath was removed, and the reaction mixture was allowed to stir at rt overnight. The reaction was carefully quenched by addition of 1M HCl, and the resulting mixture was extracted with EtOAc. The layers were separated, and the organics were washed w/brine, dried (Na$_2$SO$_4$), filtered and concentrated to afford the title compound. m/z (ES) 221 (M−OH)$^+$.

Step 3: Preparation of 2-bromo-4-chloro-3-fluorobenzaldehyde

Dess-Martin periodinane (189 mg, 0.45 mmol) was added to a stirred solution of (2-bromo-4-chloro-3-fluorophenyl)methanol (82 mg, 0.34 mmol) in DCM (3.4 mL), and the reaction mixture was allowed to stir at rt. After 1.5 h, the reaction was quenched by the addition of saturated aq. sodium thiosulfate and saturated aq. sodium bicarbonate. The resulting mixture was stirred at rt for 10 min, and extracted with DCM. The layers were separated, and the organics were dried (Na$_2$SO$_4$), filtered and concentrated to afford a crude product that was purified by flash chromatography on silica gel (isocratic elution; 50% EtOAc/hexanes as eluent) afforded the title compound. $^1$H NMR (500 MHz, CDCl$_3$) δ: 10.31 (1H, s), 7.69 (1H, d, J=1.5 Hz), 7.51 (1H, dd, J=7.4, 6.7 Hz).

Step 4: Preparation of 2-bromo-4-chloro-1-(difluoromethyl)-3-fluorobenzene

Diethylaminosulfur trifluoride (42 μL, 0.32 mmol) was added dropwise to a stirred solution of 2-bromo-4-chloro-3-fluorobenzaldehyde (50 mg, 0.21 mmol) in DCM (1.1 mL) at 0° C., and the reaction mixture was allowed to warm to rt overnight. The reaction was quenched with satd. aq. sodium bicarbonate, and the resulting mixture was extracted with EtOAc. The layers were separated, the organics were washed with brine, dried (Na₂SO₄), filtered and concentrated to afford the title compound. ¹H NMR (500 MHz, CDCl₃) δ: 7.50 (1H, dd, J=8.2, 6.9 Hz), 7.43 (1H, d, J=8.8 Hz), 6.88 (1H, t, J=14.6 Hz).

1-(4-chloro-2-(trimethylstannyl)phenyl)-4-(difluoromethyl)-1H-pyrazole

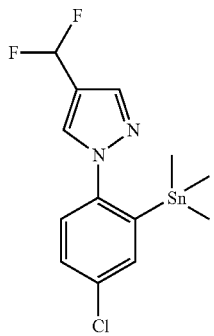 [SMILES: [CH3][Sn]([CH3])([CH3])[c]1cc(Cl)ccc1-n1cc(C(F)F)cn1]

Step 1: 1-(2-bromo-4-chlorophenyl)-1H-pyrazole

To a round bottom flask was added 2-bromo-4-chloro-1-fluorobenzene (1 g, 4.77 mmol), 1H-pyrazole (0.390 g, 5.73 mmol), CS₂CO₃ (3.89 g, 11.94 mmol) and DMF (25 mL). The reaction mixture was stirred at 100° C. for 6 h. LCMS showed the reaction was complete. The mixture was filtered and concentrated; the residue was diluted with water (50 mL) and extracted with EtOAc (20 mL×3). The combined organic layers were washed with brine (15 mL×3), dried over anhydrous sodium sulfate, filtered and concentrated. The residue was purified by normal phase chromatography (ISCO, SiO₂, 20 g Agela Flash column, 0-15% EtOAc/PE, 40 min, dry loaded) to give the title compound. ¹H NMR (CDCl₃, 400 MHz): 7.81 (d, J=2.0 Hz, 1H), 7.69-7.77 (m, 2H), 7.44-7.48 (m, 1H), 7.38-7.43 (m, 1H), 6.47 (s, 1H). MS (ESI) m/z 258.9 (M+H).

Step 2: 1-(2-bromo-4-chlorophenyl)-1H-pyrazole-4-carbaldehyde

To a round bottom flask was added 1-(2-bromo-4-chlorophenyl)-1H-pyrazole (200 mg, 0.777 mmol), TFA (1.5 mL) and 1,3,5,7-tetraazaadamantane (163 mg, 1.165 mmol). The reaction mixture was stirred at 75° C. for 18 h. LCMS showed no reaction. The temperature was raised to 100° C. and the reaction mixture was stirred for another 24 h. LCMS showed ~42% conversion. The mixture was quenched with sat. NaHCO₃ solution and adjusted to pH 7-8, followed by water (20 mL) and extracted with EtOAc (10 mL×3). The combined organic layers were dried over anhydrous sodium sulfate, filtered and concentrated. The residue was purified by prep-TLC (SiO₂, PE:EtOAc=5:1) to give the title compound. ¹H NMR (CDCl₃, 400 MHz): 9.99 (s, 1H), 8.33 (s, 1H), 8.19 (s, 1H), 7.76 (d, J=1.8 Hz, 1H), 7.43-7.54 (m, 2H). MS (ESI) m/z 327.1 (M+CH₃CN+H).

Step 3: 1-(2-bromo-4-chlorophenyl)-4-(difluoromethyl)-1H-pyrazole

To a solution of 1-(2-bromo-4-chlorophenyl)-1H-pyrazole-4-carbaldehyde (85 mg, 0.298 mmol) in DCM (2 mL) was added DAST (0.079 mL, 0.595 mmol). The resulting mixture was stirred at 25° C. for 18 h, LCMS showed the reaction was complete. The mixture was quenched with sat. NaHCO₃ solution (4 mL), followed by water (30 mL) and extracted with DCM (10 mL×3). The combined organic layers were dried over anhydrous sodium sulfate, filtered and concentrated. The residue was purified by prep-TLC (SiO₂, PE:EtOAc=5:1) to give the title compound. ¹H NMR (CDCl₃, 400 MHz): 7.98 (s, 1H), 7.87 (s, 1H), 7.74 (d, J=1.8 Hz, 1H), 7.40-7.49 (m, 2H), 6.63-6.96 (m, 1H). MS (ESI) m/z 308.9 (M+H).

Step 4: 1-(4-chloro-2-(trimethylstannyl)phenyl)-4-(difluoromethyl)-1H-pyrazole

To a solution of 1-(2-bromo-4-chlorophenyl)-4-(difluoromethyl)-1H-pyrazole (55 mg, 0.179 mmol) and 1,1,1,2,2,2-hexamethyldistannane (117 mg, 0.358 mmol) in toluene (2 mL) was added tetrakis(triphenylphosphine)palladium (41.3 mg, 0.036 mmol) and the mixture was stirred at 120° C. for 18 h. LCMS indicated that the reaction was complete. The mixture was filtered and concentrated. The residue was purified by prep-TLC (SiO₂, PE:EtOAc=10:1) to give the title compound. ¹H NMR (CDCl₃, 400 MHz): 7.82 (s, 1H), 7.59 (s, 1H), 7.41 (d, J=1.8 Hz, 1H), 7.12-7.21 (m, 2H), 6.46-6.77 (m, 1H), −0.05-0.07 (m, 9H). MS (ESI) m/z 434.0 (M+CH₃CN+H).

1-(4-chloro-2-(trimethylstannyl)phenyl)-4-(difluoromethyl)-1H-1,2,3-triazole

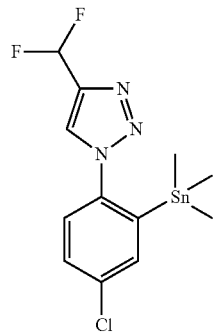 [SMILES: [CH3][Sn]([CH3])([CH3])[c]1cc(Cl)ccc1-n1cc(C(F)F)nn1]

Step 1: (1-(2-bromo-4-chlorophenyl)-1H-1,2,3-triazol-4-yl)methanol

To a round bottom flask was added 1-azido-2-bromo-4-chlorobenzene (5 g, 21.51 mmol), prop-2-yn-1-ol (2.412 g, 43.0 mmol), sodium (R)-2-((S)-1,2-dihydroxyethyl)-4-hydroxy-5-oxo-2,5-dihydrofuran-3-olate (2.130 g, 10.75 mmol), copper(II) sulfate (1.716 g, 10.75 mmol), THF (60 mL) and water (60 mL). The reaction mixture was stirred at 100° C. for 6 h. LCMS showed the reaction was complete. The mixture was filtered and concentrated. The residue was diluted with water (100 mL) and extracted with EtOAc (50 mL×3). The combined organic layers were dried over anhydrous sodium sulfate, filtered and concentrated. The residue was purified by normal phase chromatography (ISCO, SiO₂, 20 g Agela Flash column, 0-40% EtOAc/PE, 40 min, dry loaded) to give the title compound. ¹H NMR (CDCl₃, 400 MHz): 7.95 (br. s., 1H), 7.77 (s, 1H), 7.43-7.53 (m, 2H), 4.91 (br. s., 2H), 2.71 (br. s., 1H). MS (ESI) m/z 289.8 (M+H).

Step 2: 1-(2-bromo-4-chlorophenyl)-1H-1,2,3-triazole-4-carbaldehyde

To a round bottom flask was added (1-(2-bromo-4-chlorophenyl)-1H-1,2,3-triazol-4-yl)methanol (5 g, 12.48 mmol), DCM (100 mL) and manganese (IV) oxide (10.85 g, 125 mmol). The reaction mixture was stirred at 25° C. for 18 h. TLC showed the reaction was complete. The mixture was filtered and concentrated. The residue was purified by normal phase chromatography (ISCO, SiO$_2$, 20 g Agela Flash column, 0-20% EtOAc/PE, 40 min, dry loaded) to give the title compound. $^1$H NMR (CDCl$_3$, 400 MHz): 10.23 (d, J=9.7 Hz, 1H), 8.51 (d, J=4.0 Hz, 1H), 7.73 (d, J=8.6 Hz, 1H), 7.50-7.59 (m, 2H).

Step 3: 1-(2-bromo-4-chlorophenyl)-4-(difluoromethyl)-1H-1,2,3-triazole

To a solution of 1-(2-bromo-4-chlorophenyl)-1H-1,2,3-triazole-4-carbaldehyde (1.6 g, 5.58 mmol) in DCM (20 mL) was added DAST (1.476 mL, 11.17 mmol). The resulting mixture was stirred at 20° C. for 2 h, TLC showed the reaction was complete. The mixture was quenched with sat. NaHCO$_3$ solution (20 mL), followed by water (50 mL) and extracted with DCM (20 mL×3). The combined organic layers were dried over anhydrous sodium sulfate, filtered and concentrated to give the title compound which was directly used for next step without further purification. $^1$H NMR (CDCl$_3$, 400 MHz): 8.19 (d, J=9.9 Hz, 1H), 7.70 (d, J=8.6 Hz, 1H), 7.47-7.57 (m, 2H), 6.80-7.12 (m, 1H).

Step 4: 1-(4-chloro-2-(trimethylstannyl)phenyl)-4-(difluoromethyl)-1H-1,2,3-triazole To a solution of 1-(2-bromo-4-chlorophenyl)-4-(difluoromethyl)-1H-1,2,3-triazole (1.8 g, 4.38 mmol) and 1,1,1,2,2,2-hexamethyldistannane (4.30 g, 13.13 mmol) in toluene (30 mL) was added tetrakis(triphenylphosphine)palladium (1.011 g, 0.875 mmol), the mixture was stirred at 120° C. for 18 h. LCMS indicated that the reaction was complete. The mixture was filtered and concentrated. The residue was purified by normal phase chromatography (ISCO, SiO$_2$, 40 g Agela Flash column, 0-10% EtOAc/PE, 40 min, dry loaded) to give the title compound. $^1$H NMR (CDCl$_3$, 400 MHz): 7.92 (s, 1H), 7.45 (d, J=2.4 Hz, 1H), 7.28 (dd, J=8.4, 2.2 Hz, 1H), 7.14 (d, J=8.6 Hz, 1H), 6.64-6.91 (m, 1H), −0.09-0.10 (m, 9H). MS (ESI) m/z 394.0 (M+H).

4-(4-chloro-2-(trimethylstannyl)phenyl)oxazole

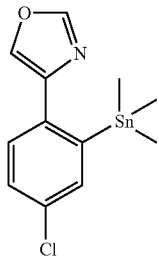 [SMILES: [CH3][Sn]([CH3])([CH3])[c]1cc(Cl)ccc1-c1cocn1]

Step 1: 2-bromo-1-(2-bromo-4-chlorophenyl)ethanone

To a solution of 1-(2-bromo-4-chlorophenyl)ethanone (4 g, 17.13 mmol) in 80 mL of CHCl$_3$ was added a solution of bromine (2875 mg, 17.99 mmol) in 20 mL of CHCl$_3$ at 0° C. The mixture was stirred at 0° C. for 3 h. HPLC showed the reaction was complete. The reaction mixture was diluted with water (50 mL) and extracted with EtOAc (70 mL×3). The combined organic layers were washed with sat. NaHCO$_3$ solution (20 mL×2), then brine (50 mL), dried over anhydrous sodium sulfate, filtered and concentrated to give the title compound which was used for the next step without further purification. $^1$H NMR (CDCl$_3$, 400 MHz): 7.67 (d, J=1.5 Hz, 1H), 7.37-7.50 (m, 2H), 4.47 (s, 2H).

Step 2: 4-(2-bromo-4-chlorophenyl)oxazole

A solution of 2-bromo-1-(2-bromo-4-chlorophenyl)ethanone (2.9 g, 9.28 mmol) in H$_2$NCHO (30 mL) was stirred at 110° C. under microwave for 2 h. LCMS showed the reaction was complete. Then the mixture was treated with water (40 mL) and extracted with EtOAc (40 mL×3). The combined organic layers were washed with brine (30 mL×4), dried over anhydrous sodium sulfate, filtered and concentrated. The residue was purified by column chromatography (silca, PE/EtOAc=1/0-20/1) to give the title compound. $^1$H NMR (CDCl$_3$, 400 MHz): 8.47 (s, 1H), 8.01 (d, J=8.6 Hz, 1H), 7.96 (s, 1H), 7.68 (d, J=1.6 Hz, 1H), 7.40 (dd, J=8.6, 2.0 Hz, 1H). MS (ESI) m/z 257.9 (M+H).

Step 3: 4-(4-chloro-2-(trimethylstannyl)phenyl)oxazole

To a solution of 4-(2-bromo-4-chlorophenyl)oxazole (400 mg, 1.547 mmol) and 1,1,1,2,2,2-hexamethyldistannane (1014 mg, 3.09 mmol) in toluene (5 mL) was added Pd(Ph$_3$P)$_4$ (179 mg, 0.155 mmol) under N$_2$, the mixture was stirred at 90° C. for 16 h. TLC (PE/EtOAc=10/1) indicated that the starting material was consumed. It was filtered and the filtrate was concentrated. The mixture was purified by p-TLC (SiO$_2$, PE/EtOAc=10/1) to give the title compound. $^1$H NMR (CDCl$_3$, 400 MHz): 7.91 (d, J=9.4 Hz, 1H), 7.60 (d, J=1.6 Hz, 1H), 7.49 (d, J=8.6 Hz, 1H), 7.31 (dd, J=8.2, 1.6 Hz, 1H), 0.25 (s, 9H).

1-(2-bromo-4-chlorophenyl)-4-chloro-1H-1,2,3-triazole

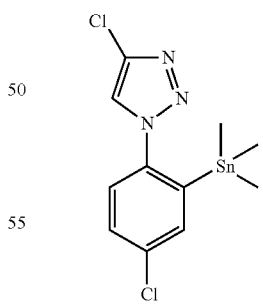

Step 1: 1-azido-2-bromo-4-chlorobenzene

To a suspension of 2-bromo-4-chloroaniline (20 g, 97 mmol) in concentrated HCl (30 mL, 365 mmol)/water (200 mL) at −5° C. was added a solution of sodium nitrite (7.35 g, 107 mmol) in 200 mL of water dropwise at −5° C. The mixture was stirred at −5° C. for 1 h. A solution of sodium azide (6.93 g, 107 mmol) in 10 mL of water was added dropwise at −5° C. Precipitates appeared during the addition and the suspension was stirred at −5° C. for 0.5 h after complete addition. The mixture was then extracted with EtOAc (700 mL×3). The combined organic layers were washed successively with sat. NaHCO$_3$ solution (200 mL), water (400 mL) and brine (500 mL), dried over anhydrous sodium sulfate, filtered and concentrated to give the title compound.

Step 2: 1-(2-bromo-4-chlorophenyl)-4-(tributylstannyl)-1H-1,2,3-triazole

To a solution of 1-azido-2-bromo-4-chlorobenzene (3.5 g, 15.06 mmol) in toluene (40 mL) was added tributyl(ethynyl)stannane (9.49 g, 30.1 mmol). The mixture was stirred at 110° C. for 8 h under N$_2$. LCMS showed the reaction was complete. Then the mixture was treated with water (40 mL) and extracted with EtOAc (40 mL×3). The combined organic layers were washed with brine (45 mL×3), dried over anhydrous sodium sulfate, filtered and concentrated. The residue was purified by column chromatography PE/EtOAc=1/0-20/1) to give the title compound. MS (ESI) m/z 548.1 (M+H).

Step 3: 1-(2-bromo-4-chlorophenyl)-4-chloro-1H-1,2,3-triazole

To a solution of 1-(2-bromo-4-chlorophenyl)-4-(tributylstannyl)-1H-1,2,3-triazole (7 g, 12.78 mmol) in acetonitrile (70 mL) was added NCS (2.56 g, 19.18 mmol) at 15° C. The mixture was stirred at 90° C. for 18 h. LCMS showed the starting material was not consumed. The mixture was stirred at 90° C. for another 24 h and concentrated. The residue was purified by column chromatography (SiO$_2$, PE/EtOAc=1/0-10/1) to give the title compound. MS (ESI) m/z 332.1 (M+H).

Step 4: 4-chloro-1-(4-chloro-2-(trimethylstannyl)phenyl)-1H-1,2,3-triazole

To a solution of 1-(2-bromo-4-chlorophenyl)-4-chloro-1H-1,2,3-triazole (2 g, 6.83 mmol) and 1,1,1,2,2,2-hexamethyldistannane (6.71 g, 20.48 mmol) in toluene (50 mL) was added Pd(Ph$_3$P)$_4$ (1.578 g, 1.365 mmol) and the mixture was stirred at 120° C. for 36 h. TLC indicated that the reaction was complete. The mixture was filtered and concentrated. The residue was diluted with water (100 mL) and extracted with EtOAc (30 mL×3). The combined organic layers were dried over anhydrous sodium sulfate, filtered and concentrated. The residue was purified by normal phase chromatography (ISCO, SiO$_2$, 20 g Agela Flash column, 0-10% EtOAc/PE, 40 min, dry loaded) to give the title compound. $^1$H NMR (CDCl$_3$, 400 MHz): 7.64 (s, 1H), 7.43 (d, J=1.98 Hz, 1H), 7.24 (dd, J=8.49, 2.09 Hz, 1H), 7.07 (s, 1H), 0.00 (s, 9H).

Examples 1 and 2

(R) 5-(5-Chloro-2-(1H-tetrazol-1-yl)phenyl)-2-(1-(5-chloro-4-(4-((methoxycarbonyl)amino)phenyl)-1H-imidazol-2-yl)-2-phenylethyl)pyridine 1-oxide (Example 1) and (S) 5-(5-Chloro-2-(1H-tetrazol-1-yl)phenyl)-2-(1-(5-chloro-4-(4-((methoxycarbonyl)amino)phenyl)-1H-imidazol-2-yl)-2-phenylethyl)pyridine 1-oxide (Example 2)

Step 1. Methyl 2-(5-bromopyridin-2-yl)-3-phenylpropanoate (1-A)

To a solution of methyl 2-(5-bromopyridin-2-yl)acetate (1 g, 4.35 mmol) in THF (20 ml) was added LHMDS (4.35 ml, 4.35 mmol, 1M) at −78° C. The mixture was stirred at −78° C. for 2 hrs. (Bromomethyl)benzene (0.743 g, 4.35 mmol) was added slowly. The cold bath was removed. The mixture was stirred at rt for 2 hrs. The reaction mixture was diluted with EtOAc, washed with water, brine and dried over Na$_2$SO$_4$. Solvent was removed in vacuo. The residue was purified by column chromatography on silica gel, eluting with EtOAc/hexane to give the desired product I-A. $^1$H NMR (500 MHz, CDCl$_3$ δ:3.24 (1H, dd), 3.45 (1H, dd), 3.66 (3H, s), 4.09 (1H, t), 7.12-7.09 (4H, m), 7.24-7.12 (2H, m), 7.73 (1H, dd), 8.65 (1H, d).

Step 2. 2-(5-Bromopyridin-2-yl)-3-phenylpropanoic acid lithium salt (1-B)

To a solution of methyl 2-(5-bromopyridin-2-yl)-3-phenylpropanoate (1-A) (780 mg, 2.436 mmol) in MeOH (10 ml) was added LiOH aq. solution (2.92 ml, 2.92 mmol, 1M). The mixture was heated at 50° C. for 15 min. The solvent was removed in vacuo. It was azeotroped by toluene and MeOH twice and further dried under vacuum to obtain the desired product. MS (ESI) m/z 306.01 (M+H).

Step 3. 2-(4-((Methoxycarbonyl)amino)phenyl)-2-oxoethyl 2-(5-bromopyridin-2-yl)-3-phenylpropanoate benzoate (1-C)

To a solution of 2-(5-Bromopyridin-2-yl)-3-phenylpropanoic acid lithium salt (1-B) (500 mg, 1.56 mmol) in DMF (10 ml), was added methyl (4-(2-chloroacetyl)phenyl)carbamate (533 mg, 2.342 mmol), and Cs$_2$CO$_3$ (509 mg, 1.562 mmol). The mixture was stirred at RT for 3 hrs, then diluted with water, and extracted with EtOAc. The combined organic fractions were washed with brine, dried (Na$_2$SO$_4$), filtered and the solvent was evaporated under reduced pressure. The residue was purified by column chromatography on silica gel Biotage® 40S, eluting with EtOAc/hexane (50%, 15 cv) to give the product. MS (ESI) m/z 497.17 (M+H).

Step 4. Methyl (4-(2-(1-(5-bromopyridin-2-yl)-2-phenylethyl)-1H-imidazol-4-yl)phenyl)carbamate (1-D)

To a solution of 2-(4-((methoxycarbonyl)amino)phenyl)-2-oxoethyl 2-(5-bromopyridin-2-yl)-3-phenylpropanoate (1-C) (310 mg, 0.62 mmol) in toluene (6 mL) was added ammonium acetate (192 mg, 2.49 mmol). The reaction mixture was heated in a microwave oven at 150° C. for 15 minutes and cooled to RT. The solvent was removed and the residue was purified by column chromatography on silica gel, eluting with EtOAc/hexane to give the product (D). MS (ESI) m/z 477.20 (M+H). $^1$H NMR (500 MHz, CDCl$_3$) δ: 3.2 (1H, m), 3.51 (1H, m), 3.78 (3H, s), 4.75 (1H, m), 6.76 (1H, s), 6.92 (2H, m), 7.21 (4H, m), 7.43 (2H, m), 7.68 (3H, m), 8.72 (1H, s).

Step 5. Methyl (4-(2-(1-(5-bromopyridin-2-yl)-2-phenylethyl)-4-chloro-1H-imidazol-5-yl)phenyl)carbamate (1-E)

To a solution of methyl (4-(2-(1-(5-bromopyridin-2-yl)-2-phenylethyl)-1H-imidazol-5-yl)phenyl)carbamate (1-D) (250 mg, 0.52 mmol) in acetonitrile (2 mL) and methylene chloride (2 mL) was added NCS (84 mg, 0.62 mmol). The reaction mixture was allowed to warm to 65° C. for 5 hrs. After cooling to RT, the mixture was concentrated under reduced pressure and water was added. The aqueous mixture was extracted with EtOAc. The combined extracts were dried over MgSO$_4$, and concentrated to dryness. The residue was purified by flash chromatography (12 g SiO$_2$) with Hex/EtOAc (0-100%) to give the product. MS (ESI) m/z 513.26 (M+H).

Step 6. Methyl (4-(2-(1-(5-bromopyridin-2-yl)-2-phenylethyl)-4-chloro-1-((2-(trimethylsilyl)ethoxy)methyl)-1H-imidazol-5-yl)phenyl)carbamate (1-F)

To a solution of methyl (4-(2-(1-(5-bromopyridin-2-yl)-2-phenylethyl)-4-chloro-1H-imidazol-5-yl)phenyl)carbamate (1-E) (100 mg, 0.2 mmol) in dichloromethane (2 mL), was added DIPEA (0.064 mL, 0.4 mmol) and SEM-Cl (36 mg, 0.22 mmol, in 0.5 mL DCM). The mixture was stirred at RT overnight, washed with saturated NH$_4$Cl and brine and dried over MgSO$_4$, and concentrated to dryness. This crude was further purified by flash chromatography (12 g gold Biotage® column) Hex/EtOAc 0-40% to obtain the product. MS (ESI) m/z 643.36 (M+H).

Step 7. Methyl (4-(2-(1-(5-(2-amino-5-chlorophenyl)pyridin-2-yl)-2-phenylethyl)-5-chloro-1-((2-(trimethylsilyl)ethoxy)methyl)-1H-imidazol-4-yl)phenyl)carbamate (1-G)

To a solution of methyl (4-(2-(1-(5-bromopyridin-2-yl)-2-phenylethyl)-5-chloro-1-((2-(trimethylsilyl)ethoxy)methyl)-1H-imidazol-4-yl)phenyl)carbamate (1-F) (65 mg, 0.1 mmol) in dioxane (5 mL), was added 4-chloro-2-(4,4,5,5-tetramethyl-1,3,2-dioxaborolan-2-yl)aniline (38 mg, 1.5 mmol), PdCl$_2$(dppf) (15 mg, 0.2 mmol) and CsF (46 mg, 0.3 mmol). The mixture was sealed in a microwave vial (15 mL), de-gassed, re-filled nitrogen and heated in an oil bath at 110° C. for 1 hour. The mixture was cooled to RT, diluted with saturated NH$_4$Cl solution (10 mL), and extracted with EtOAc (3×5 mL). The organic extracts were combined, dried over MgSO$_4$, and concentrated to dryness. The residue was further purified using flash chromatography (12 g gold SiO$_2$ column) with Hex/EtOAc (0-50%) to obtain the product. MS (ESI) m/z 477.20 (M+H).

Step 8. Methyl (4-(4-chloro-2-(1-(5-(5-chloro-2-(1H-tetrazol-1-yl)phenyl)pyridin-2-yl)-2-phenylethyl)-1-((2-(trimethylsilyl)ethoxy)methyl)-1H-imidazol-5-yl)phenyl)carbamate (1-H)

A reaction mixture of methyl (4-(2-(1-(5-(2-amino-5-chlorophenyl)pyridin-2-yl)-2-phenylethyl)-5-chloro-1-((2-(trimethylsilyl)ethoxy)methyl)-1H-imidazol-4-yl)phenyl)carbamate (1-G) (30 mg, 0.044 mmol), sodium azide (15 mg, 0.22 mmol) and trimethoxymethane (23 mg, 0.22 mmol) in acetic acid (2 mL) in a flask was heated at 90° C. for 3 hrs. The mixture was cooled and the solvent was removed in vacuo. The residue was diluted with ethyl acetate, washed with water, brine and dried over MgSO$_4$. The solvent was evaporated under reduced pressure. The residue was purified by column chromatography on silica gel, eluting with EtOAc/hexane to give the product. MS (ESI) m/z 741.55 (M+H).

Step 9. Methyl (4-(5-chloro-2-(1-(5-(5-chloro-2-(1H-tetrazol-1-yl)phenyl)pyridin-2-yl)-2-phenylethyl)-1H-imidazol-4-yl)phenyl)carbamate (1-I)

A solution of methyl (4-(4-chloro-2-(1-(5-(5-chloro-2-(1H-tetrazol-1-yl)phenyl)pyridin-2-yl)-2-phenylethyl)-1-((2-(trimethylsilyl)ethoxy)methyl)-1H-imidazol-5-yl)phenyl)carbamate (1-H) (28 mg, 0.038 mmol) in neat TFA (1.5 mL) was stirred at RT for 2 hours. The reaction solution was then evaporated under nitrogen to dryness to give the desired product. MS (ESI) m/z 611.38 (M+H)

Step 10. 5-(5-chloro-2-(1H-tetrazol-1-yl)phenyl)-2-(1-(5-chloro-4-(4-((methoxycarbonyl)amino)phenyl)-1H-imidazol-2-yl)-2-phenylethyl)pyridine 1-oxide (Example 1 and 2)

To a solution of methyl (4-(5-chloro-2-(1-(5-(5-chloro-2-(1H-tetrazol-1-yl)phenyl)pyridin-2-yl)-2-phenylethyl)-1H-imidazol-4-yl)phenyl)carbamate (1-I) (30 mg, 0.049 mmol) in acetic acid (0.5 mL) was added peracetic acid (40% in acetic acid, 47 mg, 0.25 mmol). The reaction mixture was stirred at rt for 4 hrs, and concentrated to dryness in vacuo. The residue was purified by preparative reverse phase HPLC to give the racemic product, which was resolved by SFC with chiral column (AS-H) to give (R)-5-(5-chloro-2-(1H-tetrazol-1-yl)phenyl)-2-(1-(5-chloro-4-(4-((methoxycarbonyl)amino)phenyl)-1H-imidazol-2-yl)-2-phenylethyl)pyridine 1-oxide (Example 1) and (S)-5-(5-chloro-2-(1H-tetrazol-1-yl)phenyl)-2-(1-(5-chloro-4-(4-((methoxycarbonyl)amino)phenyl)-1H-imidazol-2-yl)-2-phenylethyl)pyridine 1-oxide (Example 2). MS (ESI) m/z 627.45 (M+H). $^1$H NMR (500 MHz, CD$_3$OD) δ: 3.36 (1H, dd), 3.52 (1H, dd), 4.83 (3H, s), 5.02 (1H, t), 7.15 (2H, d), 7.20 (2H, d), 7.26 (2H, m), 7.51 (4H, dd), 7.61 (1H, d), 7.72 (1H, s), 7.98 (2H, d), 8.24 (1H, s), 9.38 (1H, s).

By using procedures similar to those described above, and appropriate starting materials, the following compounds were synthesized and characterized by LC/MS.

| Ex | Structure | Chiral Separation | Exact Mass [M + H]+ | FIIa IC50 nM | PK IC50 nM |
|---|---|---|---|---|---|
| 1 | 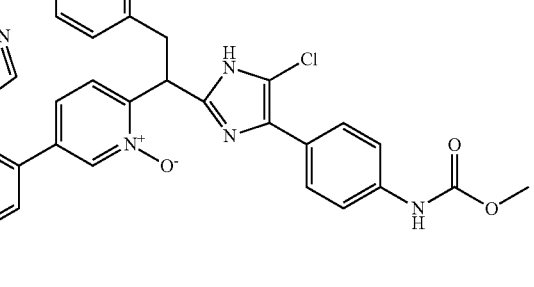 | AS-H column, fast eluting isomer | 627 | 1.34 | 1.52 |
| 2 | 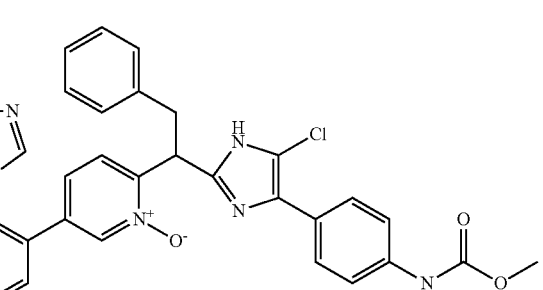 | AS-H column, slow eluting isomer | 627 | 2.82 | 76.06 |
| 3 | 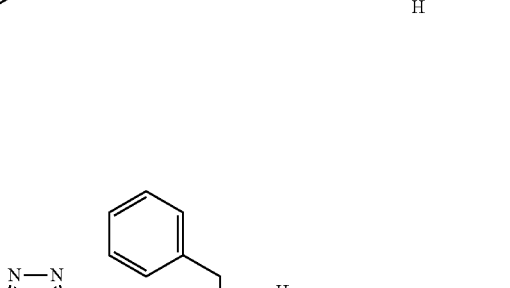 | AS-H column, fast eluting isomer | 538 | 2.87 | 27.62 |
| 4 | 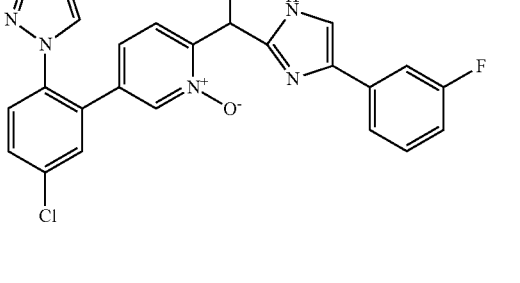 | AS-H column, slow eluting isomer | 538 | 38.89 | 624.20 |

-continued
| Ex | Structure | Chiral Separation | Exact Mass [M + H]+ | F11a IC50 nM | PK IC50 nM |
|---|---|---|---|---|---|
| 5 | 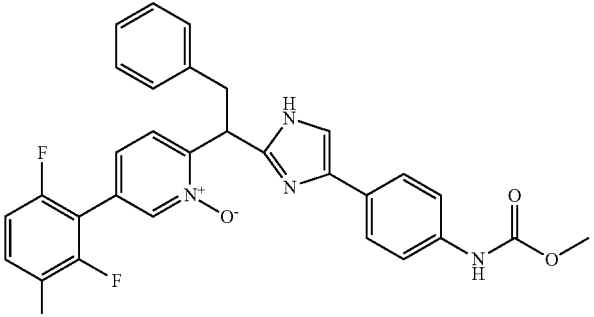 | OD-H column, fast eluting isomer | 561 | 42.18 | 137.00 |
| 6 | 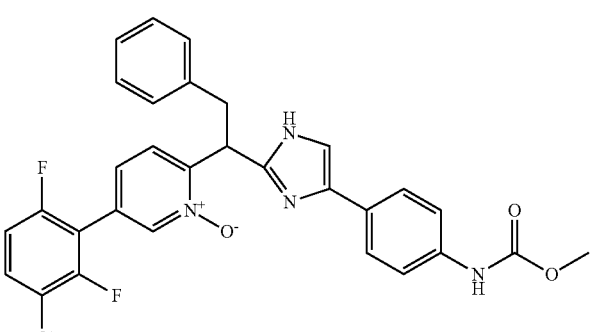 | OD-H column, slow eluting isomer | 561 | 288.90 | |
| 7 | 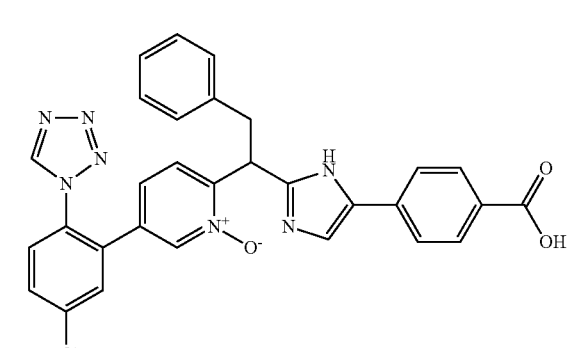 | AD-H column, fast eluting isomer | 564 | 10.16 | 469.10 |
| 8 | 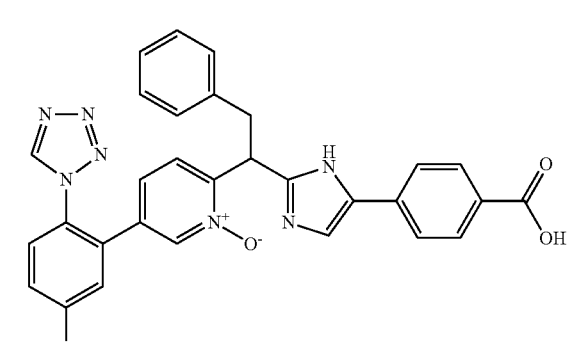 | AD-H column, slow eluting isomer | 564 | 0.67 | 25.96 |

-continued
| Ex | Structure | Chiral Separation | Exact Mass [M + H]+ | F11a IC50 nM | PK IC50 nM |
|---|---|---|---|---|---|
| 9 | 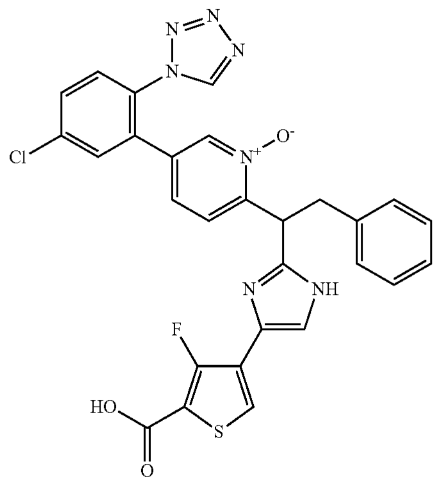 [SMILES: O=C(O)c1scc(-c2c[nH]c(C(Cc3ccccc3)c3ccc(-c4cc(Cl)ccc4-n4cnnn4)c[n+]3[O-])n2)c1F] | AS-H column, fast eluting isomer | 588 | 0.19 | 0.94 |
| 10 | 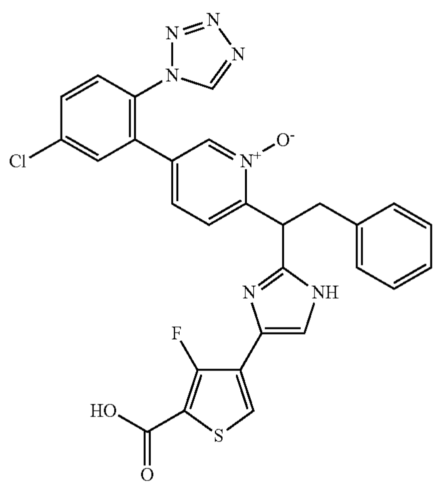 [SMILES: O=C(O)c1scc(-c2c[nH]c(C(Cc3ccccc3)c3ccc(-c4cc(Cl)ccc4-n4cnnn4)c[n+]3[O-])n2)c1F] | AS-H column, slow eluting isomer | 588 | 10.11 | 116.60 |
Examples 11 and 12
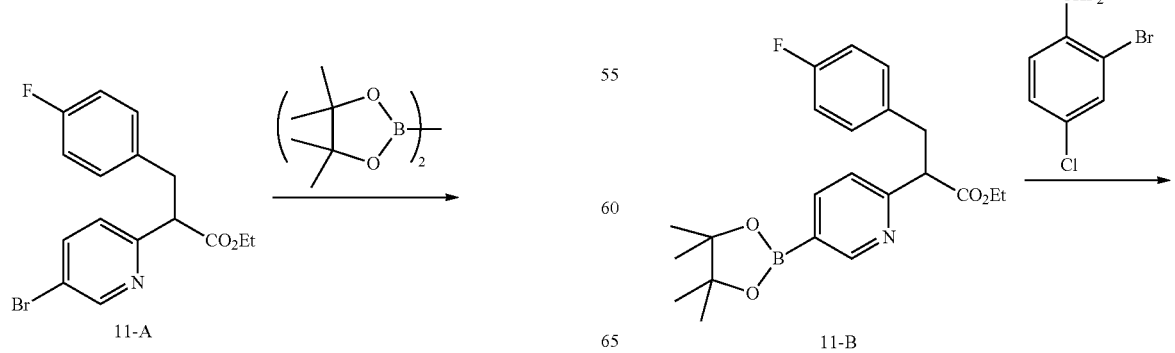
-continued

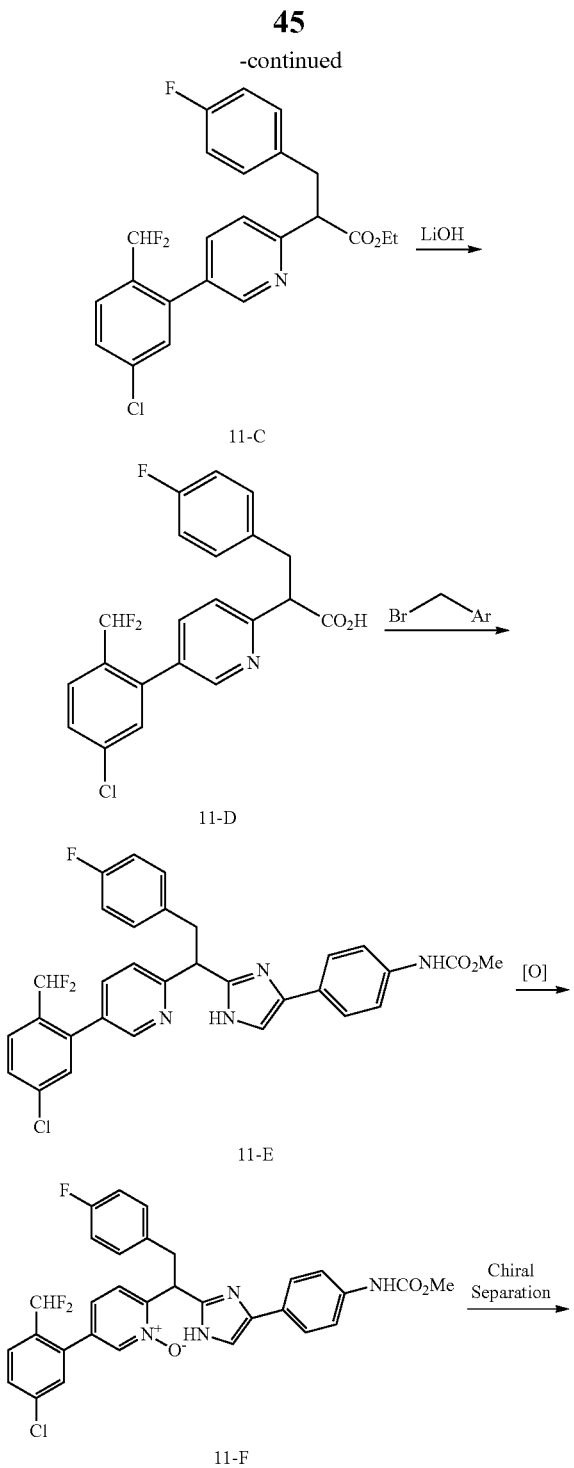

11-C

11-D

11-E

11-F

Example 11
Example 12

Preparation of ethyl 2-(5-bromopyridin-2-yl)-3-(4-fluorophenyl)propanoate (11-A)

Compound 11-A was prepared following procedures as described in step 1 of Examples 1 and 2, substituting 4-fluorobenzyl bromide for benzyl bromide. m/z (ES) 352 (MH)+.

Step 1. Ethyl 3-(4-fluorophenyl)-2-(5-(4,4,5,5-tetramethyl-1,3,2-dioxaborolan-2-yl)pyridin-2-yl)propanoate (11-B)

A mixture of compound 11-A (500 mg, 1.42 mmol), bis(pinacolato)diboron (433 mg, 1.70 mmol), potassium acetate (279 mg, 2.84 mmol) and 1,1'-bis(di-tert-butylphosphino)ferrocenepalladium dichloride (100 mg, 0.137 mmol) in dioxane (9.5 mL) was degassed via a stream of $N_2$ and heated to reflux. After 2 h, the reaction was cooled to rt, diluted with EtOAc and filtered through a pad of Celite. The organics were washed with water and brine, dried ($Na_2SO_4$), filtered and concentrated to afford the title compound 11-B. m/z (ES) 318 (M-($C_6H_{10}$))+.

Step 2. Preparation of ethyl 2-(5-(5-chloro-2-(difluoromethyl)phenyl)pyridin-2-yl)-3-(4-fluorophenyl)propanoate (11-C)

A mixture of compound 11-B (331 mg, 1.42 mmol), 2-bromo-4-chloro-1-(difluoromethyl)benzene (100 mg, 0.828 mmol; prepared following procedures reported in WO2013056060), sodium carbonate (414 μL of a 2M aq. solution, 0.828 mmol) and 1,1'-bis(di-tert-butylphosphino)ferrocenepalladium dichloride (61 mg, 0.083 mmol) in EtOH:toluene (2.75 mL of a 4:1 mixture, respectively) was degassed via a stream of $N_2$ and heated in a sealed microwave reactor to 120° C. for 20 min. After cooling to rt, the reaction mixture was diluted with EtOAc and filtered through a pad of Celite concentrated to yield a crude product that was purified by flash chromatography on silica gel (gradient elution; 10%-50% EtOAc/hexanes as eluent) as the title compound 11-C. m/z (ES) 434 (MH)+.

Step 3. Preparation of 2-(5-(5-chloro-2-(difluoromethyl)phenyl)pyridin-2-yl)-3-(4-fluorophenyl)propanoic acid (11-D)

Lithium hydroxide (22 mg, 0.92 mmol) was added to a stirred solution of compound 11-C (100 mg, 0.23 mmol) in dioxane:water (2.4 mL of a 3:1 mixture, respectively), and the resulting mixture was allowed to stir at rt. After 30 min, the reaction was quenched by addition of 1M HCl and extracted with EtOAc. The layers were separated, and the organics were washed with brine, dried ($Na_2SO_4$), filtered and concentrated to afford the title compound 11-D that was carried on without further purification. m/z (ES) 406 (MH)+.

Step 4. Preparation of methyl (4-(2-(1-(5-(5-chloro-2-(difluoromethyl)phenyl)pyridin-2-yl)-2-(4-fluorophenyl)ethyl)-1H-imidazol-4-yl)phenyl)carbamate (11-E)

Cesium carbonate (80 mg, 0.25 mmol) was added to a stirred solution of compound 11-C (100 mg, 0.25 mmol) and methyl (4-(2-chloroacetyl)phenyl)carbamate (56 mg, 0.25 mmol) in DMF (2.5 mL). The reaction mixture was allowed to stir at room temperature for 2 h, at which time, the mixture was partitioned between EtOAc and water. The layers were separated, and the organics were washed with water and brine, dried ($Na_2SO_4$), filtered and concentrated to afford a crude ester intermediate, which was dissolved in toluene (1 mL). Ammonium acetate (124 mg, 1.61 mmol) was added, and the resulting mixture was heated in a sealed microwave vial at 150° C. for 30 min. After cooling to rt, the reaction was diluted with EtOAc, filtered and concentrated to yield a crude mixture that was purified by flash chromatography on silica gel (gradient elution; 10%-100% EtOAc/hexanes as eluent) as the title compound 11-E. m/z (ES) 577 (MH)+.

Step 5 Preparation of 5-(5-chloro-2-(difluoromethyl)phenyl)-2-(2-(4-fluorophenyl)-1-(4-(4-((methoxycarbonyl)amino)phenyl)-1H-imidazol-2-yl)ethyl)pyridine 1-oxide (11-F)

Peracetic acid (92 μL, 0.56 mmol) was added to compound 11-E (64 mg, 0.11 mmol), and the resulting mixture was allowed to stir at rt. After 3.5 h, the reaction was concentrated to dryness via N₂ stream to yield a crude residue that was purified by preparative reverse phase HPLC on YMC Pack Pro C18 stationary phase (CH₃CN/H₂O as eluent, 0.05% TFA as modifier), and lyophilization of the purified fractions afforded the title compound 11-F. m/z (ES) 593.5 (MH)+.

Step 6. Chiral Separation

Compound 11-F were separated using preparative normal phase chiral SFC on a ChiralCel® OD-H (available from Chiral Technologies, Inc., Exton, Pa.) (2×25 cm) HPLC column (eluting with 25% methanol and 0.2% diethylamine/CO₂ at 60 mL/min with UV detection at 220 nm). The enantiomers were separated with the faster eluting enantiomer (Example 11) ($\alpha_D$-42.0°, methanol) having a retention time of 4.70 min, and the slower eluting enantiomer (Example 12) ($\alpha_D$+24.2°, methanol) having a retention time of 6.49 min.

Example 13

5-(3-Chloro-6-(difluoromethyl)-2-fluorophenyl)-2-(2-(4-fluorophenyl)-1-(4-(4-((methoxycarbonyl)amino)phenyl)-1H-imidazol-2-yl)ethyl)pyridine 1-oxide (Example 13)

Example 13 was prepared following procedures described in steps 1-5 of Example 12, but substituting 2-bromo-4-chloro-1-(difluoromethyl)-3-fluorobenzene for 2-bromo-4-chloro-1-(difluoromethyl)benzene in step 2. m/z (ES) 611 (MH)+.

By using procedures similar to those described above, and appropriate starting materials, the following compounds were synthesized and characterized by LC/MS.

| Ex | Structure | Chiral Separation | Exact Mass [M + H]+ | F11a IC50 nM | PK IC50 nM |
|---|---|---|---|---|---|
| 11 | 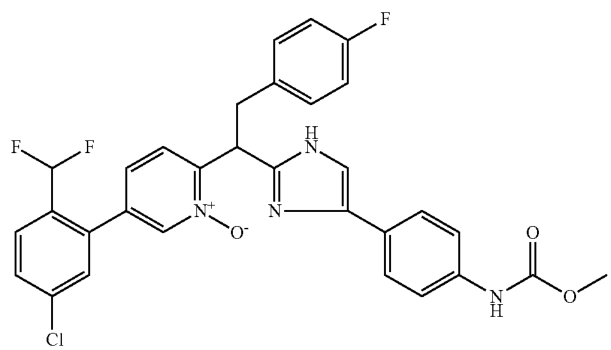 [SMILES: COC(=O)Nc1ccc(-c2c[nH]c(C(Cc3ccc(F)cc3)c3ccc(-c4cc(Cl)ccc4C(F)F)c[n+]3[O-])n2)cc1] | OD-H column, fast eluting isomer | 593 | 1.86 | 10.07 |
| 12 | 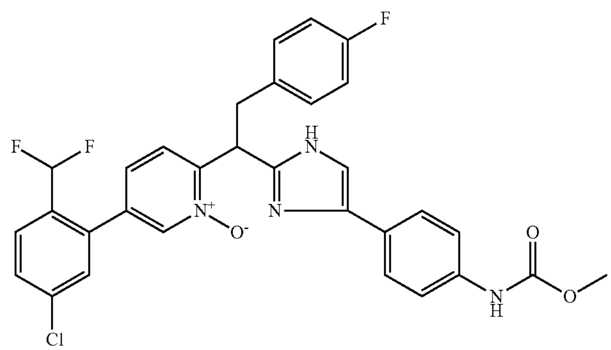 [SMILES: COC(=O)Nc1ccc(-c2c[nH]c(C(Cc3ccc(F)cc3)c3ccc(-c4cc(Cl)ccc4C(F)F)c[n+]3[O-])n2)cc1] | OD-H column, slow eluting isomer | 593 | 341.10 | |

-continued

| Ex | Structure | Chiral Separation | Exact Mass [M + H]+ | F11a IC50 nM | PK IC50 nM |
|---|---|---|---|---|---|
| 13 | 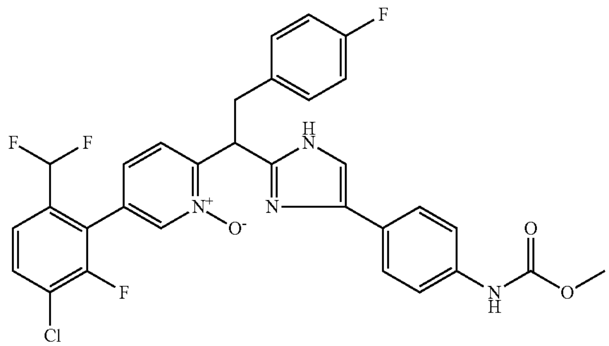 [SMILES: COC(=O)Nc1ccc(-c2c[nH]c(C(Cc3ccc(F)cc3)c3ccc(-c4c(C(F)F)ccc(Cl)c4F)c[n+]3[O-])n2)cc1] | racemic | 611 | 11.30 | 10.35 |
| 14 | 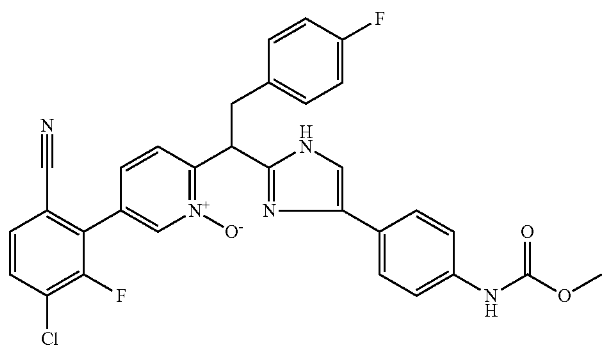 [SMILES: COC(=O)Nc1ccc(-c2c[nH]c(C(Cc3ccc(F)cc3)c3ccc(-c4c(C#N)ccc(Cl)c4F)c[n+]3[O-])n2)cc1] | racemic | 586 | 59.89 | |
| 15 | 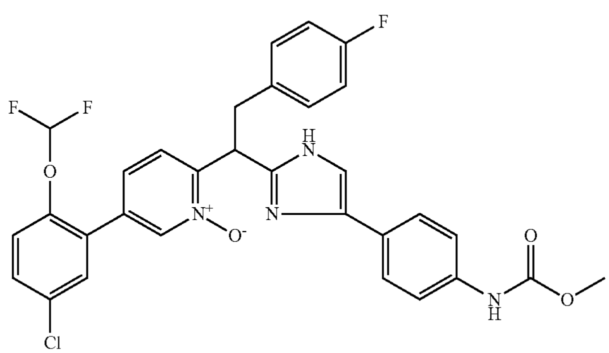 [SMILES: COC(=O)Nc1ccc(-c2c[nH]c(C(Cc3ccc(F)cc3)c3ccc(-c4cc(Cl)ccc4OC(F)F)c[n+]3[O-])n2)cc1] | racemic | 609 | 34.21 | |
| 16 | 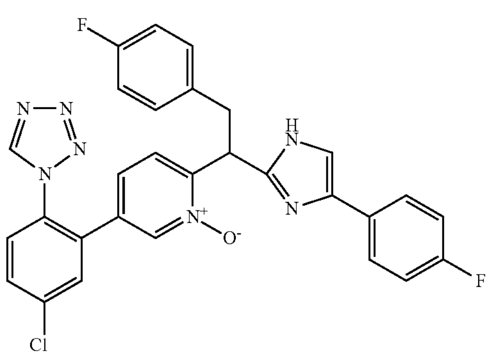 [SMILES: [O-][n+]1cc(-c2cc(Cl)ccc2-n2cnnn2)ccc1C(Cc1ccc(F)cc1)c1nc(-c2ccc(F)cc2)c[nH]1] | IA column, fast eluting isomer | 556 | 3.82 | 0.78 |

-continued

| Ex | Structure | Chiral Separation | Exact Mass [M + H]+ | F11a IC50 nM | PK IC50 nM |
|---|---|---|---|---|---|
| 17 | 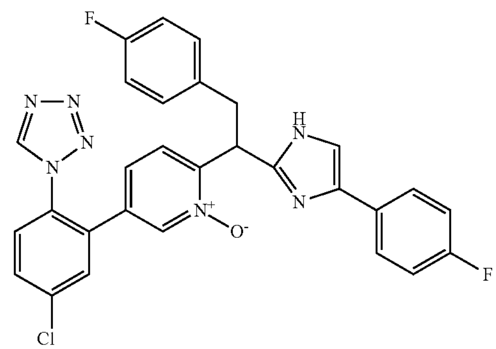 [SMILES: [O-][n+]1cc(-c2cc(Cl)ccc2-n2cnnn2)ccc1C(Cc1ccc(F)cc1)c1nc(-c2ccc(F)cc2)c[nH]1] | IA column, slow eluting isomer | 556 | 14.81 | 404.20 |
| 18 | 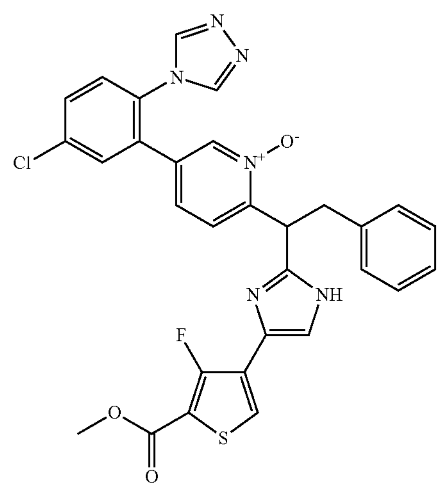 [SMILES: COC(=O)c1scc(-c2c[nH]c(C(Cc3ccccc3)c3ccc(-c4cc(Cl)ccc4-n4cnnc4)c[n+]3[O-])n2)c1F] | racemic | 602 | 8.25 | 57.20 |
| 19 | 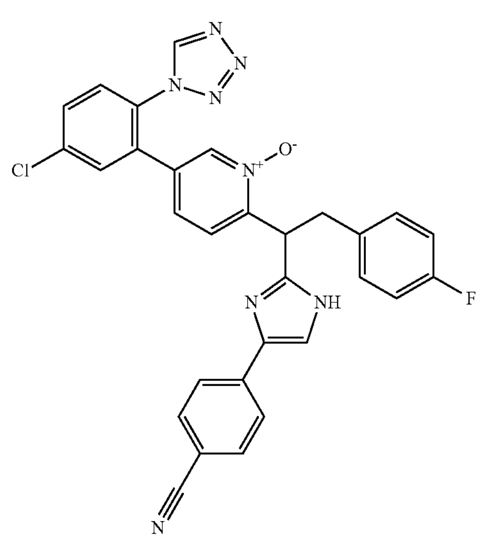 [SMILES: N#Cc1ccc(-c2c[nH]c(C(Cc3ccc(F)cc3)c3ccc(-c4cc(Cl)ccc4-n4cnnn4)c[n+]3[O-])n2)cc1] | OD-H column, fast eluting isomer | 563 | 310.90 | |

-continued

| Ex | Structure | Chiral Separation | Exact Mass [M + H]+ | F11a IC50 nM | PK IC50 nM |
|---|---|---|---|---|---|
| 20 | 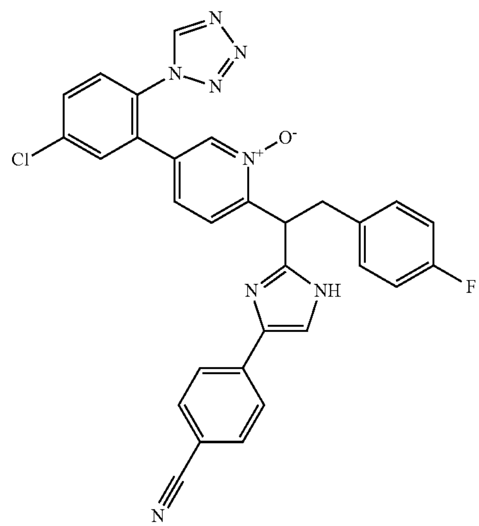 [SMILES: N#Cc1ccc(-c2c[nH]c(C(Cc3ccc(F)cc3)c3ccc(-c4cc(Cl)ccc4-n4cnnn4)c[n+]3[O-])n2)cc1] | OD-H column, slow eluting isomer | 563 | 1.54 | 28.77 |
| 21 | 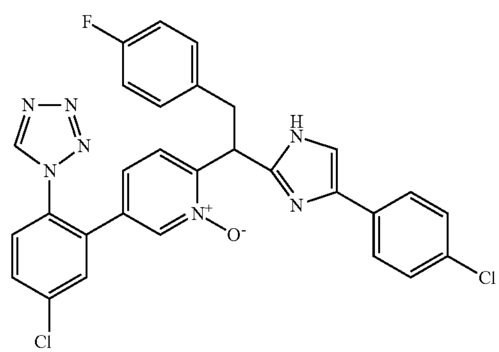 [SMILES: [O-][n+]1cc(-c2cc(Cl)ccc2-n2cnnn2)ccc1C(Cc1ccc(F)cc1)c1nc(-c2ccc(Cl)cc2)c[nH]1] | OD-H column, fast eluting isomer | 572 | 127.80 | |
| 22 | 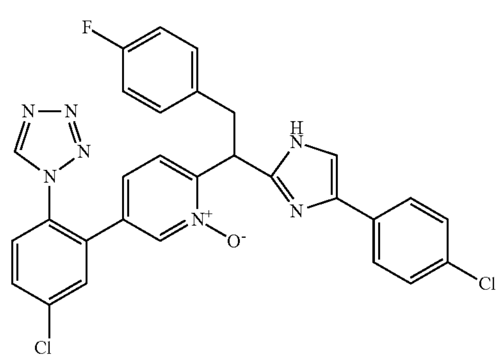 [SMILES: [O-][n+]1cc(-c2cc(Cl)ccc2-n2cnnn2)ccc1C(Cc1ccc(F)cc1)c1nc(-c2ccc(Cl)cc2)c[nH]1] | OD-H column, slow eluting isomer | 572 | 6.52 | 193.50 |

| Ex | Structure | Chiral Separation | Exact Mass [M + H]+ | F11a IC50 nM | PK IC50 nM |
|---|---|---|---|---|---|
| 23 | 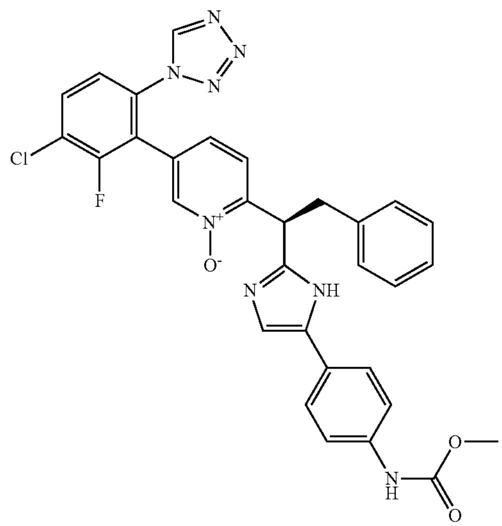 [SMILES: COC(=O)Nc1ccc(-c2cnc([C@H](Cc3ccccc3)c3ccc(-c4c(-n5cnnn5)ccc(Cl)c4F)c[n+]3[O-])[nH]2)cc1] | LUX column, fast eluting isomer | 611 | 1.04 | 1.54 |
| 24 | 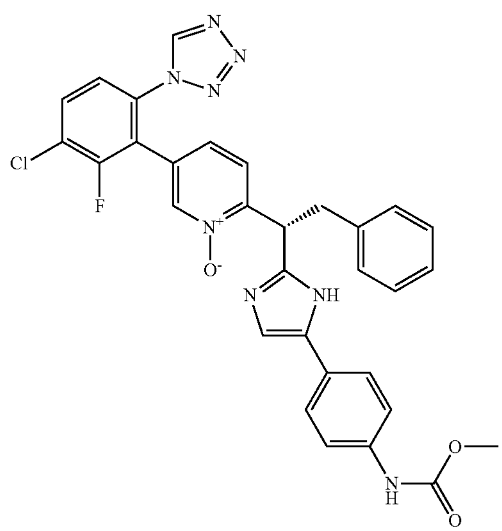 [SMILES: COC(=O)Nc1ccc(-c2cnc([C@@H](Cc3ccccc3)c3ccc(-c4c(-n5cnnn5)ccc(Cl)c4F)c[n+]3[O-])[nH]2)cc1] | LUX column, slow eluting isomer | 611 | 2.36 | 88.71 |
| 25 | 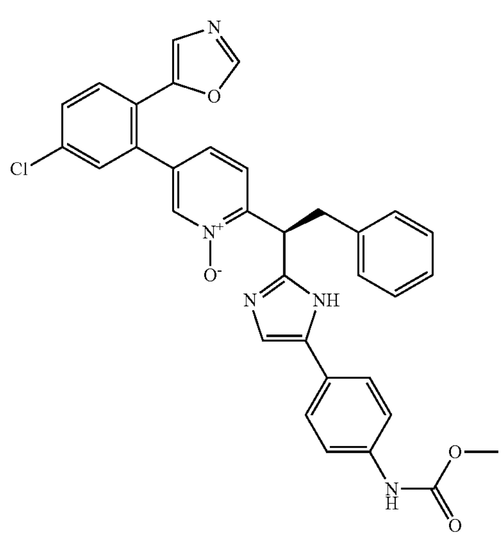 [SMILES: COC(=O)Nc1ccc(-c2cnc([C@H](Cc3ccccc3)c3ccc(-c4cc(Cl)ccc4-c4cnco4)c[n+]3[O-])[nH]2)cc1] | OD column, fast eluting isomer | 592 | 3.31 | 24.15 |

| Ex | Structure | Chiral Separation | Exact Mass [M + H]+ | F11a IC50 nM | PK IC50 nM |
|---|---|---|---|---|---|
| 26 | 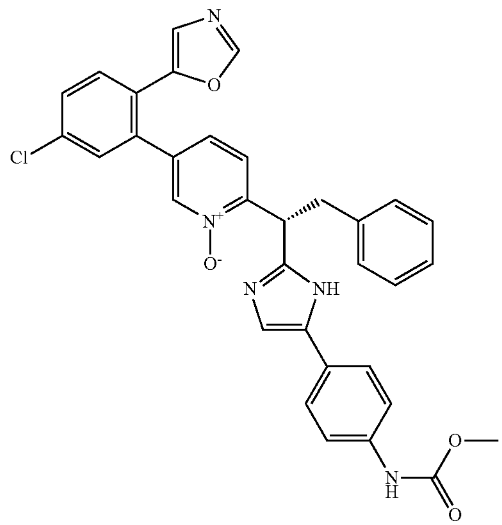 [SMILES: COC(=O)Nc1ccc(-c2cnc([C@@H](Cc3ccccc3)c3ccc(-c4cc(Cl)ccc4-c4cnco4)c[n+]3[O-])[nH]2)cc1] | OD column, slow eluting isomer | 592 | 271.40 | |

Examples 27 and 28

5-(5-chloro-2-(1H-tetrazol-1-yl)phenyl)-2-(2-cyclopropyl-1-(5-(4-((methoxycarbonyl)amino)phenyl)-1H-imidazol-2-yl)ethyl)pyridine 1-oxide Step 1: Lithium 2-(5-bromopyridin-2-yl)-3-cyclopropylpropanoate (27-B)

Lithium hydroxy monohydrate (0.89 g, 21.12 mmol) was added to the mixture of methyl 2-(5-bromopyridin-2-yl)-3-cyclopropylpropanoate (5.0 g, 17.60 mmol) in methanol (50 ml) and water (10 ml), followed by stirring at 50° C. for 30 min. After it cooled down to RT, the mixture was concentrated under reduced pressure and the residue was dried at 50° C. in a vacuum oven to give the title compound. MS (ESI) m/z 271.81 (M+H).

Step 2: 2-(4-((methoxycarbonyl)amino)phenyl)-2-oxoethyl 2-(5-bromopyridin-2-yl)-3-cyclopropylpropanoate (27-D)

Lithium 2-(5-bromopyridin-2-yl)-3-cyclopropylpropanoate (1.10 g, 4.0 mmol) was dissolved in DMF (4 ml), cesium carbonate (0.33 g, 1.0 mmol) and methyl (4-(2-bromoacetyl)phenyl) carbamate (1.09 g, 4.0 mmol) were added. The mixture was stirred at RT for 5 h. The solid was filtered through celite and the filtrate was concentrated under reduced pressure and the residue was purified by column chromatography on a silica gel (Teledyne ISCO Si; 24 g prepacked), eluting with 10-80% EtOAc/hexane to give the title compound. MS (ESI) m/z 462.91 (M+H).

Step 3: (4-(2-(1-(5-Bromopyridin-2-yl)-2-cyclopropylethyl)-1H-imidazol-5-yl)phenyl)carbamate (27-E)

A pressure release vial was charged with 2-(4-((methoxycarbonyl)amino)phenyl)-2-oxoethyl 2-(5-bromopyridin-2-yl)-3-cyclopropylpropanoate (1.64 g, 3.56 mmol), ammonium acetate (2.74 g, 35.6 mmol), acetic acid (2 ml, 34.9 mmol), and toluene (20 mL). The vial was capped, and the mixture was heated at 130° C. for 45 min by microwave reactor. The reaction mixture was diluted with ethyl acetate and washed with water. The aqueous layer was extracted with ethyl acetate (2×50 ml). The combined organic phase was washed with brine, and dried over MgSO4. After it was filtered, the solution was concentrated under reduced pressure. The residue was purified by column chromatography on silica gel (Teledyne ISCO Si; 40 g prepacked), eluting with 10-85% EtOAc/hexane to give 27-E. MS (ESI) m/z 442.75 (M+H).

Step 4: Methyl (4-(2-(1-(5-(2-amino-5-chlorophenyl)pyridin-2-yl)-2-cyclopropylethyl)-1H-imidazol-5-yl)phenyl)carbamate (27-F)

A flask was charged with 4-chloro-2-(4,4,5,5-tetramethyl-1,3,2-dioxaborolan-2-yl)aniline (0.86 g, 3.40 mmol), potassium phosphate tribasic (0.96 g, 4.53 mmol), 1,1'-bis(di-tert-butylphosphino)ferrocene palladium dichloride (0.30 g, 0.45 mmol), and methyl (4-(2-(1-(5-bromopyridin-2-yl)-2-cyclopropylethyl)-1H-imidazol-5-yl)phenyl)carbamate (1.0 g, 2.27 mmol). The flask was capped, and the air was exchanged by vacuum/back-filling nitrogen (×2). THF (15 ml) and water (3 ml) were introduced by syringe. The mixture was heated at 60° C. for 45 min in an oil bath. After cooling down, the reaction mixture was diluted with water and extracted with EtOAc (3×50 mL). The combined organic phase was dried over MgSO4, filtered, concentrated under reduced pressure. The crude was purified by flash chromatography on a silica-gel column (40 g silica-gel prepacked column), eluting with 0-10% MeOH/CH2Cl2 to give the title compound. MS (ESI) m/z 487.93 (M+H).

Step 5: Methyl (4-(2-(1-(5-(5-chloro-2-(1H-tetrazol-1-yl)phenyl)pyridin-2-yl)-2-cyclopropylethyl)-1H-imidazol-5-yl)phenyl)carbamate (27-G)

To a solution of methyl (4-(2-(1-(5-(2-amino-5-chlorophenyl)pyridin-2-yl)-2-cyclopropylethyl)-1H-imidazol-5- yl)phenyl)carbamate (0.89 g, 1.824 mmol) in acetic acid (15 ml) was added sodium azide (0.71 g, 10.94 mmol) and trimethyl orthoformate (1.21 ml, 10.94 mmol). The reaction flask was then capped, and the mixture was stirred at room temperature overnight. The solvent was removed by reduced pressure and the residue was purified by column chromatography on silica gel (Teledyne ISCO Si; 40 g prepacked), eluting with 0-15% MeOH/CH$_2$Cl$_2$ to give the title compound. MS (ESI) m/z 540.90 (M+H).

Step 6: 5-(5-Chloro-2-(1H-tetrazol-1-yl)phenyl)-2-(1-(4-chloro-5-(4-((methoxycarbonyl)amino)phenyl)-1H-imidazol-2-yl)-2-cyclopropylethyl)pyridine 1-oxide (Example 27 and 28)

Peracetic acid (1.06 ml, 6.4 mmol) was added to a solution of methyl (4-(2-(1-(5-(5-chloro-2-(1H-tetrazol-1-yl)phenyl)pyridin-2-yl)-2-cyclopropylethyl)-1H-imidazol-5-yl)phenyl)carbamate (0.69 g, 1.28 mmol) in acetic acid (5 ml). The reaction flask was capped and the mixture was stirred at room temperature for 24 hours. The solvent was removed under reduced pressure and the residue was purified by column chromatography on silica gel (Teledyne ISCO Si; 24 g prepacked), eluting with 0-15% MeOH/CH$_2$Cl$_2$ to give a racemic product. MS (ESI) m/z 556.82 (M+H), which was separated by SFC with the condition (Kromasil, 3×250 mm, 50% MeOH (0.2% NH$_4$OH)/CO$_2$, 70 ml/min, 100 mbar, 220 nM 35° C., ~50 mg/ml in MeOH) to give Example 27 (enantiomer 1) and Example 28 (enantiomer 2).

Examples 29 and 30

4-[2-(1-{5-[5-chloro-2-(1H-tetrazol-1-yl)phenyl]-1-oxidopyridin-2-yl}-2-cyclopropylethyl)-1H-imidazol-5-yl]benzonitrile Step 1: Methyl 2-(5-(2-((tert-butoxycarbonyl)amino)-5-chlorophenyl)pyridin-2-yl)-3-cyclopropylpropanoate (29-B)

To a round bottom flask was added methyl 2-(5-bromopyridin-2-yl)-3-cyclopropylpropanoate (27-A) (2.8 g, 9.85 mmol), K$_3$PO$_4$ (6.28 g, 29.6 mmol), tert-butyl (4-chloro-2-(4,4,5,5-tetramethyl-1,3,2-dioxaborolan-2-yl)phenyl)carbamate (3.83 g, 10.84 mmol), THF (80 mL), water (20 mL) and 1,1'-bis(di-tert-butylphosphino)ferrocene palladium dichloride (0.321 g, 0.493 mmol) at 20° C. The reaction mixture was stirred at 20° C. for 16 h. LCMS showed the reaction was complete. The mixture was filtered and the filtrate was concentrated. The residue was purified by silica gel gradient chromatography (SiO$_2$, PE:EtOAc=1:0-30:1) to give the title compound. $^1$H NMR (CDCl$_3$, 400 MHz): 8.56 (d, J=1.5 Hz, 1H), 8.02 (d, J=8.4 Hz, 1H), 7.66 (dd, J=7.9, 2.0 Hz, 1H), 7.46 (d, J=8.2 Hz, 1H), 7.34 (dd, J=8.8, 2.2 Hz, 1H), 7.17 (d, J=2.2 Hz, 1H), 6.24 (br. s., 1H), 4.03 (t, J=7.6 Hz, 1H), 3.75 (s, 3H), 2.04-2.12 (m, 1H), 1.85-1.95 (m, 1H), 1.45 (s, 9H), 0.70 (br. s., 1H), 0.43 (ddt, J=13.1, 8.7, 4.3 Hz, 2H), 0.09-0.16 (m, 1H), −0.02-0.05 (m, 1H) MS (ESI) m/z: 431.1 (M+H).

Step 2: 5-(2-((tert-Butoxycarbonyl)amino)-5-chlorophenyl)-2-(3-cyclopropyl-1-ethoxy-1-oxopropan-2-yl)pyridine 1-oxide (29-C)

To a round bottom flask were added ethyl 2-(5-(2-((tert-butoxycarbonyl)amino)-5-chlorophenyl)pyridin-2-yl)-3-cyclopropylpropanoate (29-B) (4 g, 8.99 mmol), DCM (70 mL) and 3-chlorobenzoperoxoic acid (2.387 g, 10.79 mmol) at 20° C. The reaction mixture was stirred at 20° C. for 16 h. LCMS showed the reaction was complete. The mixture was quenched with sat. Na$_2$SO$_3$ solution (30 mL), followed by water (150 mL) and extracted with DCM (80 mL×3). The combined organic layers were washed with sat. NaHCO$_3$ solution (100 mL×3), dried over anhydrous sodium sulfate, filtered and the filtrate was concentrated. The residue was purified by silica gel gradient chromatography (SiO$_2$, PE:EtOAc=100:0-10:1) to give the title compound. $^1$H NMR (CDCl$_3$, 400 MHz): 8.25 (s, 1H), 8.00 (d, J=8.4 Hz, 1H), 7.49 (d, J=8.2 Hz, 1H), 7.37 (d, J=6.8 Hz, 1H), 7.23 (br. s., 1H), 7.18 (s, 1H), 6.21 (br. s., 1H), 4.37-4.43 (m, 1H), 3.77 (s, 3H), 3.50 (br. s., 1H), 1.99 (q, J=7.2 Hz, 2H), 1.46 (s, 9H), 0.77 (br. s., 1H), 0.47 (d, J=7.5 Hz, 2H), 0.13 (br. s., 1H), 0.08 (br. s., 1H). MS (ESI) m/z: 447.1 (M+H).

Step 3: Lithium 2-(5-(2-(((tert-butoxycarbonyl)amino)-5-chlorophenyl)-1-oxidopyridin-2-yl)-3-cyclopropylpropanoate (29-D)

To a solution of 5-(2-((tert-butoxycarbonyl)amino)-5-chlorophenyl)-2-(3-cyclopropyl-1-methoxy-1-oxopropan-2-yl)pyridine 1-oxide (29-C) (3.6 g, 8.06 mmol) in ethanol (50 mL) and water (10 mL) was added lithium hydroxide hydrate (0.37 g, 8.8 mmol) and the mixture was stirred at 16° C. for 16 h. LC-MS showed the reaction was complete. Then the mixture was concentrated to give the title compound, which was used for next step without further purification. MS (ESI) m/z: 433.2 (M+H) (acid).

Step 4: 5-(2-((tert-Butoxycarbonyl)amino)-5-chlorophenyl)-2-(1-(2-(4-cyanophenyl)-2-oxoethoxy)-3-cyclopropyl-1-oxopropan-2-yl)pyridine 1-oxide (29-F)

To a mixture of lithium 2-(5-(2-((tert-butoxycarbonyl)amino)-5-chlorophenyl)-1-oxidopyridin-2-yl)-3-cyclopropylpropanoate (29-D) (600 mg, 1.367 mmol) and 4-(2-bromoacetyl)benzonitrile (29-E) (337 mg, 1.504 mmol) in DMF (10 mL) was added Cs$_2$CO$_3$ (579 mg, 1.777 mmol) at 20° C., and the mixture was stirred at 20° C. for 16 h. LCMS indicated that the reaction was complete. The residue was diluted with water (50 mL) and extracted with EtOAc (50 mL×3). The combined organic layers were washed with brine (50 mL), dried over anhydrous sodium sulfate, filtered, and concentrated. The residue was purified by silica gel gradient chromatography (SiO$_2$, PE:EtOAc=5:1-2:1) to give the title compound. $^1$H NMR (CDCl$_3$, 400 MHz): 8.27 (s, 1H), 7.93-8.05 (m, 3H), 7.81 (d, J=8.5 Hz, 2H), 7.60 (d, J=8.0 Hz, 1H), 7.36-7.44 (m, 1H), 7.30 (br. s., 1H), 7.19 (d, J=2.0 Hz, 1H), 6.23 (br. s., 1H), 5.29-5.47 (m, 2H), 4.52 (t, J=7.3 Hz, 1H), 2.15 (dd, J=14.1, 7.0 Hz, 1H), 2.02 (d, J=7.0 Hz, 1H), 1.34-1.53 (m, 9H), 0.87 (br. s., 1H), 0.50 (d, J=7.0 Hz, 2H), 0.06-0.21 (m, 2H). MS (ESI) m/z: 576.2 (M+H).

Step 5: 5-(2-((tert-butoxycarbonyl)amino)-5-chlorophenyl)-2-(1-(5-(4-cyanophenyl)-1H-imidazol-2-yl)-2-cyclopropylethyl)pyridine 1-oxide (29-G)

To a microwave tube were added a solution of 5-(2-((tert-butoxycarbonyl)amino)-5-chlorophenyl)-2-(1-(2-(4-cyanophenyl)-2-oxoethoxy)-3-cyclopropyl-1-oxopropan-2-yl) pyridine 1-oxide (29-F) (250 mg, 0.434 mmol) and ammonium acetate (669 mg, 8.68 mmol) in toluene (5 ml). The reaction mixture was stirred at 120° C. 40 min in a microwave. The mixture was diluted with water (30 mL) and extracted with EtOAc (30 mL×3). The combined organic layers were washed with brine (30 mL), dried over anhydrous sodium sulfate, filtered and concentrated. The residue was purified by silica gel gradient chromatography (SiO$_2$, PE:EtOAc=3:1-1:2) to give the title compound. $^1$H NMR (CDCl$_3$, 400 MHz): 8.15 (s, 1H), 7.69 (d, J=7.9 Hz, 2H), 7.45 (dd, J=13.0, 8.2 Hz, 3H), 7.13-7.26 (m, 3H), 7.01 (br. s., 2H), 5.99 (br. s., 1H), 4.71 (br. s., 1H), 2.27 (br. s., 1H), 2.15 (br. s., 1H), 1.25 (s, 9H), 0.63 (br. s., 1H), 0.27 (br. s., 2H), 0.00 (br. s., 2H). MS (ESI) m/z: 556.3 (M+H).

Step 6: 5-(2-Amino-5-chlorophenyl)-2-(1-(5-(4-cyanophenyl)-1H-imidazol-2-yl)-2-cyclopropylethyl)pyridine 1-oxide (29-H)

To a mixture of 5-(2-((tert-butoxycarbonyl)amino)-5-chlorophenyl)-2-(1-(5-(4-cyanophenyl)-1H-imidazol-2-yl)-2-cyclopropylethyl)pyridine 1-oxide (29-G) (180 mg, 0.32 mmol) in DCM (4 mL) was added TFA (2.5 mL, 32 mmol) and the mixture was stirred at 20° C. for 15 h. The reaction was concentrated to give the crude title compound, which was used for next step without further purification. MS (ESI) m/z: 456.2 (M+H).

Step 7: 5-(5-Chloro-2-(1H-tetrazol-1-yl)phenyl)-2-(1-(5-(4-cyanophenyl)-1H-imidazol-2-yl)-2-cyclopropylethyl)pyridine 1-oxide (Racemic Product)

A mixture of 5-(2-amino-5-chlorophenyl)-2-(1-(5-(4-cyanophenyl)-1H-imidazol-2-yl)-2-cyclopropylethyl)pyridine 1-oxide (29-H) (180 mg, 0.395 mmol), sodium azide (513 mg, 7.90 mmol) and trimethyl orthoformate (838 mg, 7.90 mmol) in HOAc (5 mL) was stirred at 30° C. for 16 h. The mixture was adjusted to pH 8 with sat. NaHCO$_3$ and extracted with EtOAc (30 mL×3). The combined organic layers were dried over anhydrous sodium sulfate, filtered, and concentrated. The residue was purified by prep-HPLC (TFA) to give the title compound. $^1$H NMR (CD$_3$OD, 400 MHz): 9.42 (s, 1H), 8.28 (s, 1H), 7.99 (s, 1H), 7.88 (s, 4H), 7.77-7.82 (m, 2H), 7.68-7.75 (m, 2H), 7.30 (d, J=8.4 Hz, 1H), 4.94-5.00 (m, 1H), 2.32 (dt, J=13.5, 6.8 Hz, 1H), 2.10-2.18 (m, 1H), 0.70 (br. s., 1H), 0.46 (dd, J=8.5, 3.9 Hz, 2H), 0.08-0.15 (m, 1H), −0.05-0.01 (m, 1H). MS (ESI) m/z: 509.3 (M+H).

Step 8: 5-(5-Chloro-2-(1H-tetrazol-1-yl)phenyl)-2-(1-(5-(4-cyanophenyl)-1H-imidazol-2-yl)-2-cyclopropylethyl)pyridine 1-oxide (Example 29 and 30)

A sample of the racemic 5-(5-chloro-2-(1H-tetrazol-1-yl)phenyl)-2-(1-(5-(4-cyanophenyl)-1H-imidazol-2-yl)-2-cyclopropylethyl)pyridine 1-oxide (70 mg, 0.138 mmol) was purified by SFC on chiral AS column (250 mm×30 mm, 10 um), eluting with 50% EtOH/CO$_2$ to give 5-(5-chloro-2-(1H-tetrazol-1-yl)phenyl)-2-(1-(5-(4-cyanophenyl)-1H-imidazol-2-yl)-2-cyclopropylethyl)pyridine 1-oxide, the fast eluting enantiomer (Example 29), and 5-(5-chloro-2-(1H-tetrazol-1-yl)phenyl)-2-(1-(5-(4-cyanophenyl)-1H-imidazol-2-yl)-2-cyclopropylethyl)pyridine 1-oxide, the slow eluting enantiomer (Example 30). Example 29: $^1$H NMR (CD$_3$OD, 400 MHz): 9.36 (s, 1H), 8.21 (s, 1H), 7.86 (d, J=6.7 Hz, 2H), 7.73-7.79 (m, 2H), 7.69 (d, J=8.2 Hz, 3H), 7.57 (br. s., 2H), 7.18 (d, J=8.2 Hz, 1H), 4.98 (br. s., 1H), 2.16 (br. s., 1H), 1.95 (br. s., 1H), 0.70 (br. s., 1H), 0.37 (d, J=3.9 Hz, 2H), 0.08 (br. s., 1H), 0.00 (br. s., 1H). MS (ESI) m/z: 509.0 (M+H). Example 30: $^1$H NMR (CD$_3$OD, 400 MHz): 9.36 (s, 1H), 8.22 (s, 1H), 7.85 (d, J=8.2 Hz, 2H), 7.73-7.79 (m, 2H), 7.65-7.73 (m, 3H), 7.54-7.62 (m, 2H), 7.19 (d, J=7.8 Hz, 1H), 4.99 (dd, J=8.8, 6.1 Hz, 1H), 2.13-2.19 (m, 1H), 2.00 (dd, J=13.7, 6.7 Hz, 1H), 0.70 (br. s., 1H), 0.35-0.43 (m, 2H), 0.07-0.11 (m, 1H), −0.03-0.02 (m, 1H). MS (ESI) m/z: 509.0 (M+H).

By using procedures similar to those described above, and appropriate starting materials, the following compounds were synthesized and characterized by LC/MS.

| Ex | Structure | Chiral Separation | Exact Mass [M + H]+ | F11a IC50 nM | PK IC50 nM |
|---|---|---|---|---|---|
| 27 | 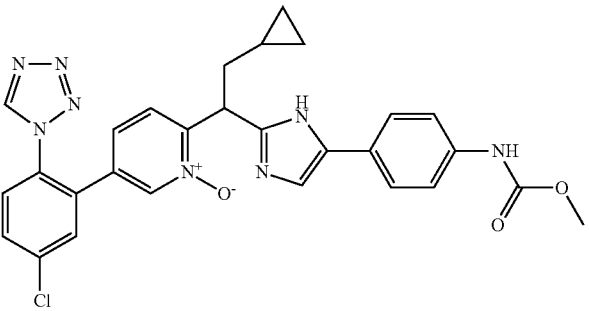 [SMILES: COC(=O)Nc1ccc(-c2cnc(C(CC3CC3)c3ccc(-c4cc(Cl)ccc4-n4cnnn4)c[n+]3[O-])[nH]2)cc1] | Kromasil column, slow eluting isomer | 557 | 13.98 | 207.10 |

-continued

| Ex | Structure | Chiral Separation | Exact Mass [M + H]+ | F11a IC50 nM | PK IC50 nM |
|---|---|---|---|---|---|
| 28 | 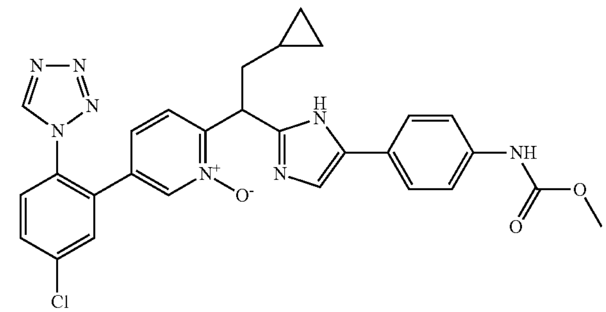 [SMILES: COC(=O)Nc1ccc(-c2cnc(C(CC3CC3)c3ccc(-c4cc(Cl)ccc4-n4cnnn4)c[n+]3[O-])[nH]2)cc1] | Kromasil column, fast eluting isomer | 557 | 0.25 | 20.82 |
| 29 | 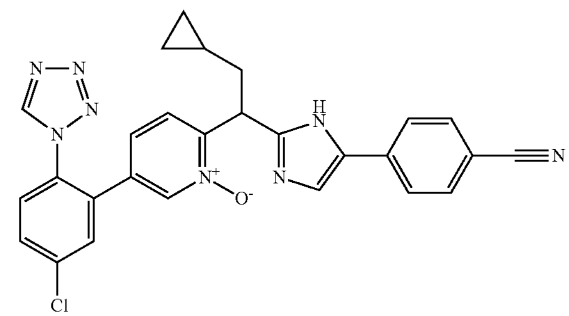 [SMILES: N#Cc1ccc(-c2cnc(C(CC3CC3)c3ccc(-c4cc(Cl)ccc4-n4cnnn4)c[n+]3[O-])[nH]2)cc1] | AS column, Fast eluting isomer | 509 | 2.85 | 225.80 |
| 30 | 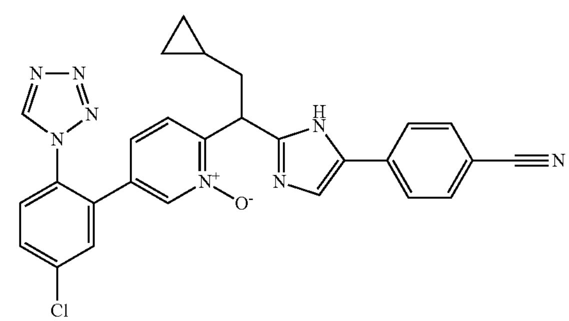 [SMILES: N#Cc1ccc(-c2cnc(C(CC3CC3)c3ccc(-c4cc(Cl)ccc4-n4cnnn4)c[n+]3[O-])[nH]2)cc1] | AS column, slow eluting isomer | 509 | 266.30 | |
| 31 | 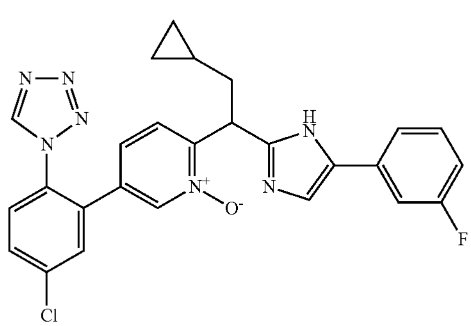 [SMILES: [O-][n+]1cc(-c2cc(Cl)ccc2-n2cnnn2)ccc1C(CC1CC1)c1ncc(-c2cccc(F)c2)[nH]1] | Fast eluting isomer | 502 | 1000.00 | |

-continued
| Ex | Structure | Chiral Separation | Exact Mass [M + H]+ | F11a IC50 nM | PK IC50 nM |
|---|---|---|---|---|---|
| 32 | 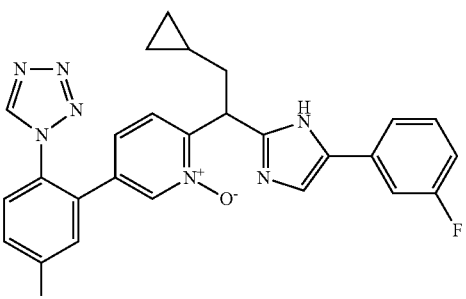 | Slow eluting isomer | 502 | 14.71 | 427.90 |
| 33 | 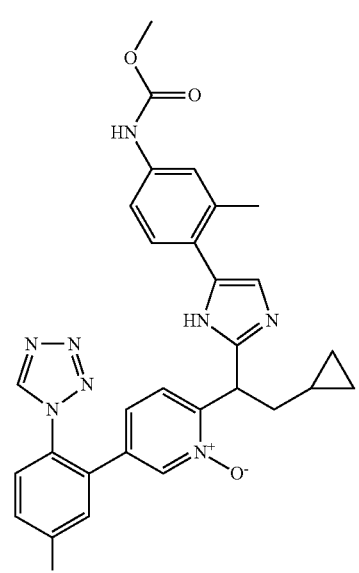 | IC column, fast eluting isomer | 571 | 18.96 | 625.10 |
| 34 | 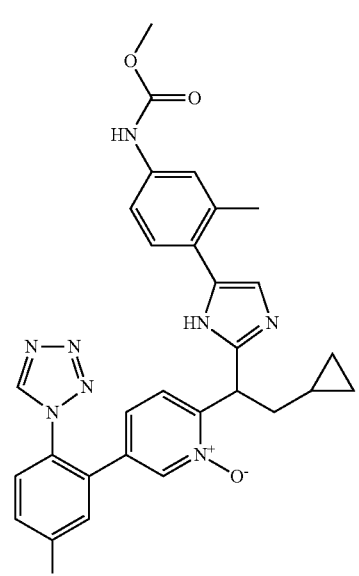 | IC column, slow eluting isomer | 571 | 0.24 | 31.35 |

-continued

| Ex | Structure | Chiral Separation | Exact Mass [M + H]+ | F11a IC50 nM | PK IC50 nM |
|---|---|---|---|---|---|
| 35 | 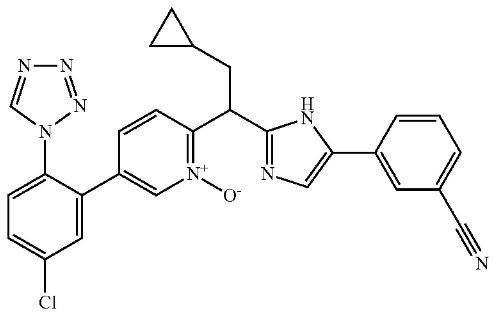 | Fast eluting isomer | 509 | 1000.00 | |
| 36 | 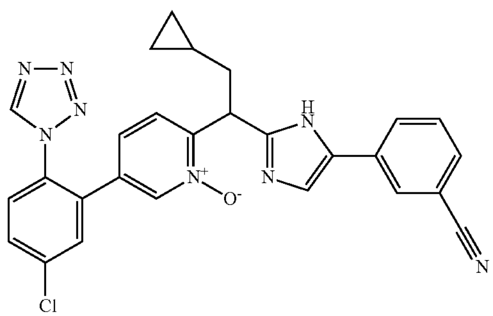 | Slow eluting isomer | 509 | 27.43 | 376.90 |
| 37 | 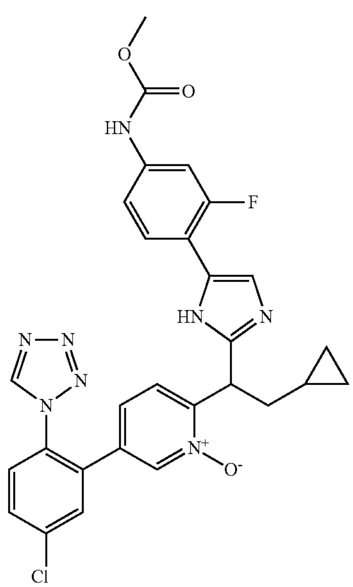 [SMILES: COC(=O)Nc1ccc(-c2cnc(C(CC3CC3)c3ccc(-c4cc(Cl)ccc4-n4cnnn4)c[n+]3[O-])[nH]2)c(C)c1] | ID column, fast eluting isomer | 575 | 74.77 | |

| Ex | Structure | Chiral Separation | Exact Mass [M + H]+ | F11a IC50 nM | PK IC50 nM |
|---|---|---|---|---|---|
| 38 | 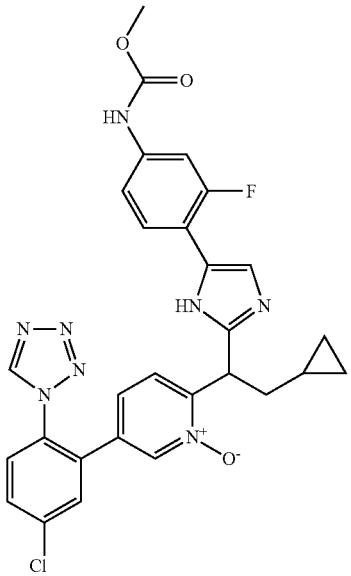 [SMILES: COC(=O)Nc1ccc(-c2cnc(C(CC3CC3)c3ccc(-c4cc(Cl)ccc4-n4cnnn4)c[n+]3[O-])[nH]2)c(C)c1] | IC column, slow eluting isomer | 575 | 0.48 | 38.54 |
| 39 | 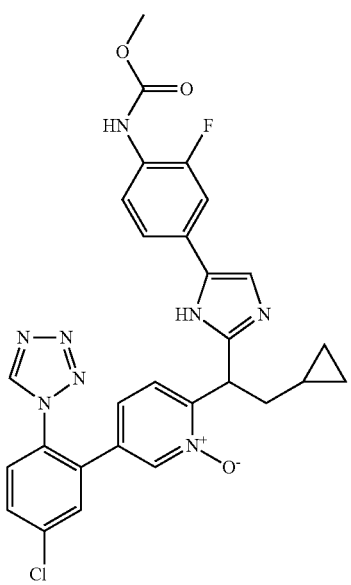 [SMILES: COC(=O)Nc1ccc(-c2cnc(C(CC3CC3)c3ccc(-c4cc(Cl)ccc4-n4cnnn4)c[n+]3[O-])[nH]2)cc1F] | IC column, fast eluting isomer | 575 | | |

-continued
| Ex | Structure | Chiral Separation | Exact Mass [M + H]+ | F11a IC50 nM | PK IC50 nM |
|---|---|---|---|---|---|
| 40 | 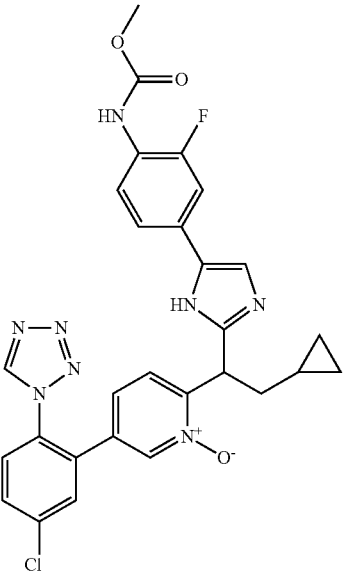 [SMILES: COC(=O)Nc1ccc(-c2cnc(C(CC3CC3)c3ccc(-c4cc(Cl)ccc4-n4cnnn4)c[n+]3[O-])[nH]2)cc1F] | IC column, slow eluting isomer | 575 | 1.52 | 39.02 |
| 41 | 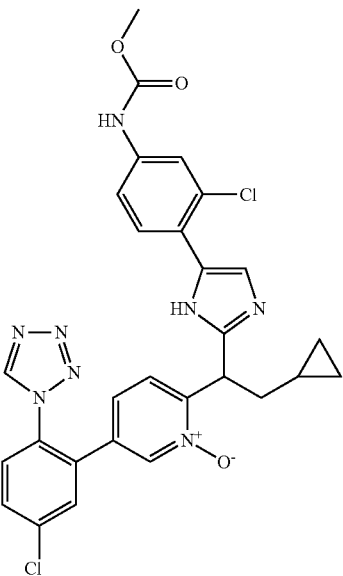 | ID column, fast eluting isomer | 591 | 23.69 | 399.20 |

-continued

| Ex | Structure | Chiral Separation | Exact Mass [M + H]+ | F11a IC50 nM | PK IC50 nM |
|---|---|---|---|---|---|
| 42 | 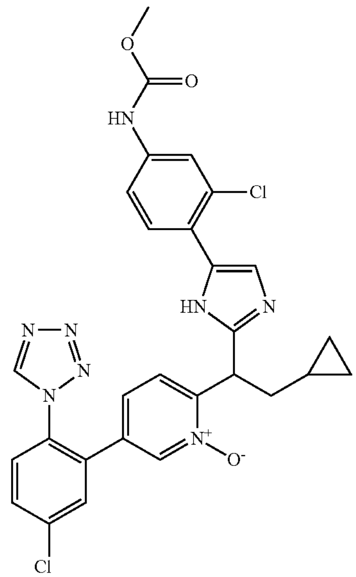 | ID column, slow eluting isomer | 591 | 0.58 | 28.06 |
| 43 | 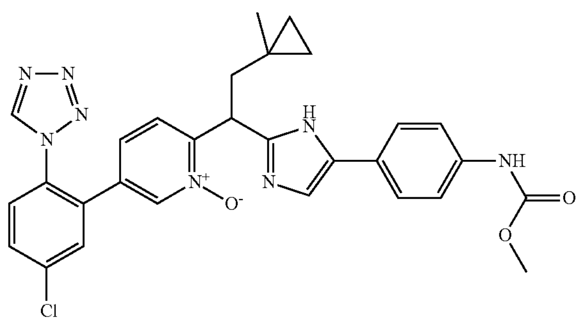 [SMILES: COC(=O)Nc1ccc(-c2cnc(C(CC3(C)CC3)c3ccc(-c4cc(Cl)ccc4-n4cnnn4)c[n+]3[O-])[nH]2)cc1] | Fast eluting isomer | 571 | 48.24 | 887.00 |
| 44 | 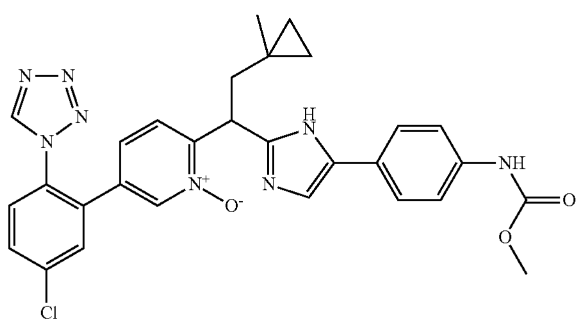 [SMILES: COC(=O)Nc1ccc(-c2cnc(C(CC3(C)CC3)c3ccc(-c4cc(Cl)ccc4-n4cnnn4)c[n+]3[O-])[nH]2)cc1] | Slow eluting isomer | 571 | 1.52 | 14.71 |
| 45 | 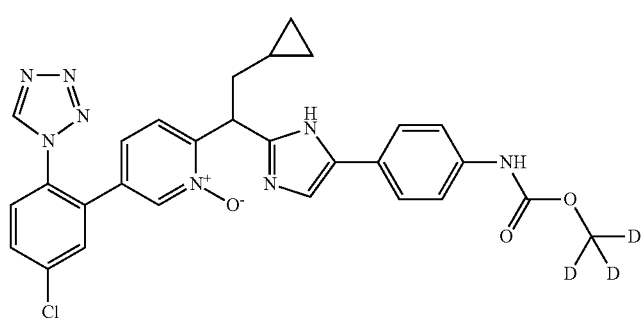 [SMILES: [2H]C([2H])([2H])OC(=O)Nc1ccc(-c2cnc(C(CC3CC3)c3ccc(-c4cc(Cl)ccc4-n4cnnn4)c[n+]3[O-])[nH]2)cc1] | racemic | 560 | 0.43 | |

| Ex | Structure | Chiral Separation | Exact Mass [M + H]+ | F11a IC50 nM | PK IC50 nM |
|---|---|---|---|---|---|
| 46 | 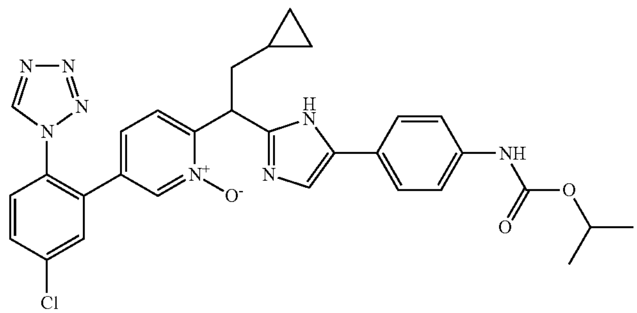 [SMILES: CC(C)OC(=O)Nc1ccc(-c2cnc(C(CC3CC3)c3ccc(-c4cc(Cl)ccc4-n4cnnn4)c[n+]3[O-])[nH]2)cc1] | racemic | 585 | 2.91 | |

Examples 47 and 48

6-chloro-5-[2-(1-{5-[5-chloro-2-(1H-tetrazol-1-yl)phenyl]-1-oxidopyridin-2-yl}-2-cyclopropylethyl)-1H-imidazol-5-yl]pyridin-2-amine Step 1: 2-(1-(2-(6-acetamido-2-chloropyridin-3-yl)-2-oxoethoxy)-3-cyclopropyl-1-oxopropan-2-yl)-5-(2-((tert-butoxycarbonyl)amino)-5-chlorophenyl)pyridine 1-oxide (47-B)

To a mixture of lithium 2-(5-(2-((tert-butoxycarbonyl)amino)-5-chlorophenyl)-1-oxidopyridin-2-yl)-3-cyclopropylpropanoate (29-D) (800 mg, 1.823 mmol) and N-(5-(2-bromoacetyl)-6-chloropyridin-2-yl)acetamide (47-A) (585 mg, 2.005 mmol) in DMF (10 mL) was added $Cs_2CO_3$ (772 mg, 2.370 mmol) at 20° C. and the mixture was stirred at 20° C. for 16 h. The residue was diluted with water (50 mL) and extracted with EtOAc (50 mL×3). The combined organic layers were washed with brine (50 mL), dried over anhydrous sodium sulfate, filtered, and concentrated. The residue was purified by silica gel gradient chromatography ($SiO_2$, PE:EtOAc=5:1-1:1) to give the title compound. $^1$H NMR ($CDCl_3$, 400 MHz): 8.18-8.25 (m, 2H), 8.06 (d, J=8.5 Hz, 1H), 7.96 (d, J=9.0 Hz, 1H), 7.49 (d, J=8.0 Hz, 1H), 7.39 (dd, J=8.8, 2.3 Hz, 1H), 7.18-7.26 (m, 2H), 6.43 (s, 1H), 5.18-5.36 (m, 2H), 4.48 (t, J=7.3 Hz, 1H), 2.18 (s, 3H), 2.07-2.14 (m, 1H), 1.98 (dt, J=14.3, 7.4 Hz, 1H), 1.47 (s, 9H), 0.81 (br. s., 1H), 0.40-0.53 (m, 2H), 0.03-0.19 (m, 2H). MS (ESI) m/z: 643.2 (M+H).

Step 2: 2-(1-(5-(6-acetamido-2-chloropyridin-3-yl)-1H-imidazol-2-yl)-2-cyclopropylethyl)-5-(2-((tert-butoxycarbonyl)amino)-5-chlorophenyl)pyridine 1-oxide (47-C)

To a microwave tube were added a mixture of 2-(1-(2-(6-acetamido-2-chloropyridin-3-yl)-2-oxoethoxy)-3-cyclopropyl-1-oxopropan-2-yl)-5-(2-((tert-butoxycarbonyl)amino)-5-chlorophenyl)pyridine 1-oxide (47-B) (500 mg, 0.777 mmol), and ammonium acetate (1.198 g, 15.54 mmol) in toluene (4 mL). The mixture was stirred at 150° C. for 50 min under MW. LCMS indicated that the reaction was complete. The mixture was diluted with water (30 mL) and extracted with EtOAc (30 mL×3). The combined organic layers were washed with brine (30 mL), dried over anhydrous sodium sulfate, filtered, and concentrated. The residue was purified by silica gel gradient chromatography ($SiO_2$, PE: ethyl acetate=2:1-1:3) to give the title compound. MS (ESI) m/z: 623.3 (M+H).

Step 3: 2-(1-(5-(6-acetamido-2-chloropyridin-3-yl)-1H-imidazol-2-yl)-2-cyclopropylethyl)-5-(2-amino-5-chlorophenyl)pyridine 1-oxide (47-D)

To a mixture of 2-(1-(5-(6-acetamido-2-chloropyridin-3-yl)-1H-imidazol-2-yl)-2-cyclopropylethyl)-5-(2-((tert-butoxycarbonyl)amino)-5-chlorophenyl)pyridine 1-oxide (47-C) (170 mg, 0.273 mmol) in DCM (4 mL) was added TFA (2.101 mL, 27.3 mmol) and the mixture was stirred at 20° C. for 15 h. The reaction was concentrated to give the crude title compound, which was used for next step without further purification. MS (ESI) m/z: 523.1 (M+H).

Step 4: 2-(1-(5-(6-acetamido-2-chloropyridin-3-yl)-1H-imidazol-2-yl)-2-cyclopropylethyl)-5-(5-chloro-2-(1H-tetrazol-1-yl)phenyl)pyridine 1-oxide (47-E)

A mixture of 2-(1-(5-(6-acetamido-2-chloropyridin-3-yl)-1H-imidazol-2-yl)-2-cyclopropylethyl)-5-(2-amino-5-chlorophenyl)pyridine 1-oxide (47-D) (170 mg, 0.325 mmol), sodium azide (422 mg, 6.50 mmol) and trimethyl orthoformate (690 mg, 6.50 mmol) in HOAc (5 mL) was stirred at 30° C. for 16 h. The mixture was adjusted to pH 8 with sat. $NaHCO_3$ and extracted with EtOAc (30 mL×3). The combined organic layers were dried over anhydrous sodium sulfate, filtered, and concentrated to give the crude title compound, which was used for next step without further purification. $^1$H NMR ($CDCl_3$, 400 MHz): 8.51 (s, 1H), 8.44 (br. s., 1H), 8.11-8.22 (m, 2H), 7.88 (br. s., 1H), 7.65 (d, J=8.6 Hz, 1H), 7.48-7.58 (m, 3H), 7.38 (d, J=8.2 Hz, 1H), 6.83 (d, J=8.6 Hz, 1H), 4.78 (br. s., 1H), 3.32 (s, 3H), 2.39 (br. s., 1H), 1.93-2.02 (m, 1H), 0.69 (br. s., 1H), 0.41 (br. s., 2H), 0.02-0.16 (m, 2H). MS (ESI) m/z: 576.2 (M+H).

Step 5: 2-(1-(5-(6-amino-2-chloropyridin-3-yl)-1H-imidazol-2-yl)-2-cyclopropylethyl)-5-(5-chloro-2-(1H-tetrazol-1-yl)phenyl)pyridine 1-oxide (Example 47 and 48)

To a solution 2-(1-(5-(6-acetamido-2-chloropyridin-3-yl)-1H-imidazol-2-yl)-2-cyclopropylethyl)-5-(5-chloro-2-(1H-tetrazol-1-yl)phenyl)pyridine 1-oxide (47-E) (20 mg, 0.035 mmol) in MeOH (2.5 mL) and water (1 mL) was added 10% $H_2SO_4$ (0.111 mL, 0.208 mmol) and the mixture was stirred at 20° C. for 4 h. The reaction was diluted with sat. NaHCO₃ (30 mL) and extracted with EtOAc (3×50 mL). The combined organic phases were dried over anhydrous sodium sulfate, filtered and concentrated. The residue was purified by prep-HPLC (TFA condition) to give the racemic product.

A sample of the racemic product (40 mg, 0.075 mmol) was purified by SFC on chiral AD column, eluting with 55% EtOH/CO₂ to give 1 2-(1-(5-(6-amino-2-chloropyridin-3-yl)-1H-imidazol-2-yl)-2-cyclopropylethyl)-5-(5-chloro-2-(1H-tetrazol-1-yl)phenyl)pyridine 1-oxide, fast eluting enantiomer (Example 47) and 2-(1-(5-(6-amino-2-chloropyridin-3-yl)-1H-imidazol-2-yl)-2-cyclopropylethyl)-5-(5-chloro-2-(1H-tetrazol-1-yl)phenyl)pyridine 1-oxide, slow eluting enantiomer (Example 48).

Example 47

¹H NMR (CD3OD, 400 MHz): 9.38 (s, 1H), 8.25 (s, 1H), 7.74-7.82 (m, 2H), 7.68-7.73 (m, 1H), 7.65 (d, J=8.6 Hz, 1H), 7.58 (d, J=8.2 Hz, 1H), 7.43 (s, 1H), 7.22 (d, J=7.8 Hz, 1H), 6.54 (d, J=8.2 Hz, 1H), 4.93-4.98 (m, 1H), 2.11 (t, J=7.2 Hz, 2H), 0.68 (br. s., 1H), 0.42 (d, J=7.0 Hz, 2H), 0.08 (br. s., 1H), −0.01 (br. s., 1H). MS (ESI) m/z: 534.0 (M+H).

Example 48

¹H NMR (CD₃OD, 400 MHz): 9.36 (s, 1H), 8.21 (s, 1H), 7.63-7.87 (m, 4H), 7.51 (d, J=8.2 Hz, 1H), 7.31 (br. s., 1H), 7.17 (d, J=7.4 Hz, 1H), 6.53 (d, J=8.2 Hz, 1H), 4.96-5.03 (m, 1H), 2.11-2.21 (m, 1H), 1.86-1.95 (m, 1H), 0.70 (br. s., 1H), 0.38 (d, J=7.4 Hz, 2H), 0.08 (br. s., 1H), 0.01 (br. s., 1H). MS (ESI) m/z: 534.0 (M+H).

By using procedures similar to those described above, and appropriate starting materials, the following compounds were synthesized and characterized by LC/MS.

| Ex | Structure | Chiral Separation | Exact Mass [M + H]+ | F11a IC50 nM | PK IC50 nM |
|---|---|---|---|---|---|
| 47 | 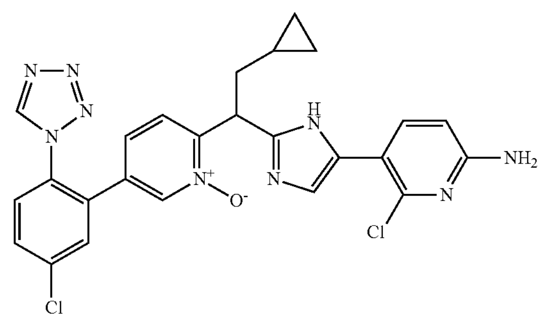 [SMILES: Nc1ccc(-c2cnc(C(CC3CC3)c3ccc(-c4cc(Cl)ccc4-n4cnnn4)c[n+]3[O-])[nH]2)c(Cl)n1] | AD column Fast eluting isomer | 534 | 0.32 | 80 |
| 48 | 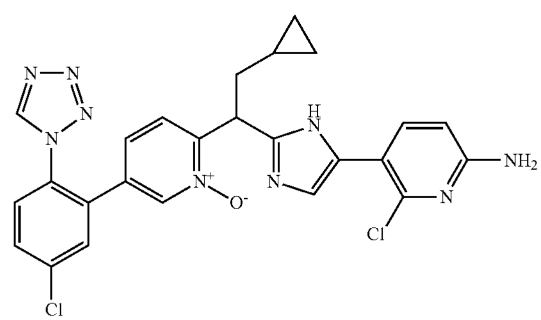 [SMILES: Nc1ccc(-c2cnc(C(CC3CC3)c3ccc(-c4cc(Cl)ccc4-n4cnnn4)c[n+]3[O-])[nH]2)c(Cl)n1] | AD column slow eluting isomer | 534 | 71.97 | |
| 49 | 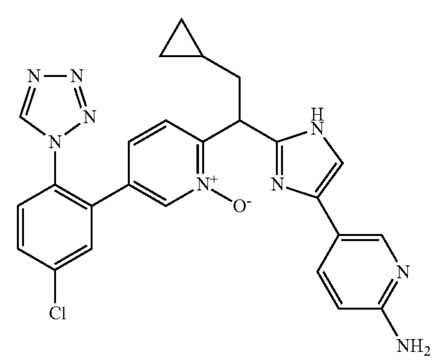 [SMILES: Nc1ccc(-c2c[nH]c(C(CC3CC3)c3ccc(-c4cc(Cl)ccc4-n4cnnn4)c[n+]3[O-])n2)cn1] | Whelk0-1 column, fast eluting isomer | 500 | 19.47 | 2118 |

| Ex | Structure | Chiral Separation | Exact Mass [M + H]+ | F11a IC50 nM | PK IC50 nM |
|---|---|---|---|---|---|
| 50 | 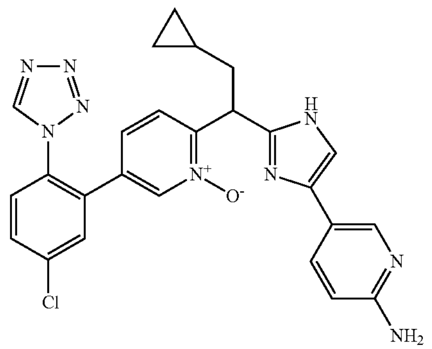 [SMILES: Nc1ccc(-c2c[nH]c(C(CC3CC3)c3ccc(-c4cc(Cl)ccc4-n4cnnn4)c[n+]3[O-])n2)cn1] | Whelk0-1 column, slow eluting isomer | 500 | 1.08 | 228 |

Examples 51 and 52

3-[2-(1-{5-[5-chloro-2-(1H-tetrazol-1-yl)phenyl]-1-oxidopyridin-2-yl}-2-cyclopropylethyl)-1H-imidazol-5-yl]-2-fluorobenzoic acid Step 1: 5-(2-((tert-butoxycarbonyl)amino)-5-chlorophenyl)-2-(3-cyclopropyl-1-(2-(2-fluoro-3-(methoxycarbonyl)phenyl)-2-oxoethoxy)-1-oxopropan-2-yl)pyridine 1-oxide (51-B)

To a mixture of lithium 2-(5-(2-((tert-butoxycarbonyl)amino)-5-chlorophenyl)-1-oxidopyridin-2-yl)-3-cyclopropylpropanoate (29-D) (400 mg, 0.912 mmol) and methyl 3-(2-bromoacetyl)-2-fluorobenzoate (51-A) (276 mg, 1.003 mmol) in DMF (5 ml) was added $Cs_2CO_3$ (386 mg, 1.185 mmol) at 20° C. and the mixture was stirred at 20° C. for 16 h. The mixture was diluted with water (50 mL) and extracted with EtOAc (50 mL×3). The combined organic layers were washed with brine (50 mL), dried over anhydrous sodium sulfate, filtered, and concentrated. The residue was purified by silica gel gradient chromatography ($SiO_2$, PE:EtOAc=5:1-1:1) to give the title compound. $^1$H NMR ($CDCl_3$, 400 MHz): 8.24 (s, 1H), 8.07-8.18 (m, 2H), 7.96-8.03 (m, 1H), 7.61 (d, J=8.2 Hz, 1H), 7.30-7.41 (m, 2H), 7.26 (br. s., 1H), 7.17 (d, J=2.3 Hz, 1H), 6.24 (br. s., 1H), 5.22-5.38 (m, 2H), 4.63 (t, J=7.0 Hz, 1H), 3.95 (s, 3H), 2.11-2.18 (m, 1H), 1.93-2.01 (m, 1H), 1.41-1.47 (m, 9H), 0.84-0.90 (m, 1H), 0.47 (d, J=7.8 Hz, 2H), 0.06-0.14 (m, 2H). MS (ESI) m/z 627.1 (M+H).

Step 2: 5-(2-((tert-butoxycarbonyl)amino)-5-chlorophenyl)-2-(2-cyclopropyl-1-(5-(2-fluoro-3-(methoxycarbonyl)phenyl)-1H-imidazol-2-yl)ethyl)pyridine 1-oxide (51-C)

To a microwave tube were added a mixture of 5-(2-((tert-butoxycarbonyl)amino)-5-chlorophenyl)-2-(3-cyclopropyl-1-(2-(2-fluoro-3-(methoxycarbonyl)phenyl)-2-oxoethoxy)-1-oxopropan-2-yl)pyridine 1-oxide (51-B) (300 mg, 0.478 mmol) and ammonium acetate (738 mg, 9.57 mmol) in toluene (5 mL). The mixture was stirred at 120° C. for 40 min in a microwave. The mixture was diluted with water (30 mL) and extracted with EtOAc (30 mL×3). The combined organic layers were washed with brine (30 mL), dried over anhydrous sodium sulfate, filtered and concentrated. The residue was purified by silica gel gradient chromatography ($SiO_2$, PE:EtOAc=3:1-1:2) to give the title compound. $^1$H NMR ($CDCl_3$, 400 MHz): 8.21-8.34 (m, 2H), 7.85 (d, J=8.2 Hz, 1H), 7.68 (t, J=6.7 Hz, 1H), 7.53 (d, J=7.8 Hz, 1H), 7.37 (br. s., 1H), 7.24-7.33 (m, 2H), 7.13-7.18 (m, 1H), 7.11 (d, J=2.0 Hz, 1H), 6.11 (br. s., 1H), 4.83 (br. s., 1H), 4.01-4.09 (m, 1H), 3.87 (s, 3H), 2.37 (br. s., 1H), 2.22 (br. s., 1H), 1.34 (s, 9H), 0.73 (br. s., 1H), 0.36 (br. s., 2H), 0.10 (d, J=5.5 Hz, 2H). MS (ESI) m/z 607.1 (M+H).

Step 3: lithium 3-(2-(1-(5-(2-((tert-butoxycarbonyl)amino)-5-chlorophenyl)-1-oxidopyridin-2-yl)-2-cyclopropylethyl)-1H-imidazol-5-yl)-2-fluorobenzoate (51-D)

To a solution of 5-(2-((tert-butoxycarbonyl)amino)-5-chlorophenyl)-2-(2-cyclopropyl-1-(5-(2-fluoro-3-(methoxycarbonyl)phenyl)-1H-imidazol-2-yl)ethyl)pyridine 1-oxide (51-C) (300 mg, 0.494 mmol)) in MeOH (10 mL) and water (2 mL) was added lithium hydroxide hydrate (20.74 mg, 0.494 mmol) and the mixture was stirred at 45° C. for 16 h. Then the mixture was concentrated to give the crude title compound, which was used for next step without further purification. MS (ESI) m/z 593.2 (M+H).

Step 4: 5-(2-amino-5-chlorophenyl)-2-(1-(5-(3-carboxy-2-fluorophenyl)-1H-imidazol-2-yl)-2-cyclopropylethyl)pyridine 1-oxide (51-E)

To a solution of lithium 3-(2-(1-(5-(2-((tert-butoxycarbonyl)amino)-5-chlorophenyl)-1-oxidopyridin-2-yl)-2-cyclopropylethyl)-1H-imidazol-5-yl)-2-fluorobenzoate (51-D) (300 mg, 0.401 mmol) in DCM (5 mL) was added TFA (1.543 mL, 20.03 mmol), and the mixture was stirred at 20° C. for 15 h. The reaction was concentrated to give the crude title compound, which was used for next step without further purification. MS (ESI) m/z 493.1 (M+H).

Step 5: 2-(1-(5-(3-carboxy-2-fluorophenyl)-1H-imidazol-2-yl)-2-cyclopropylethyl)-5-(5-chloro-2-(1H-tetrazol-1-yl)phenyl)pyridine 1-oxide (Example 51 and 52)

A mixture of 5-(2-amino-5-chlorophenyl)-2-(1-(5-(3-carboxy-2-fluorophenyl)-1H-imidazol-2-yl)-2-cyclopropylethyl)pyridine 1-oxide (51-E) (200 mg, 0.406 mmol), sodium azide (528 mg, 8.11 mmol) and trimethyl orthoformate (861 mg, 8.11 mmol) in HOAc (5 mL) was stirred at 30° C. for 16 h. The mixture was adjusted to pH 8 with sat. NaHCO$_3$ and extracted with EtOAc (30 mL×3). The combined organic layers were dried over anhydrous sodium sulfate, filtered, and concentrated. The residue was purified by prep-HPLC (TFA) to give the racemic product, which was separated by SFC on chiral AD column, eluting with 50% EtOH/CO$_2$ to give 2-(1-(5-(3-carboxy-2-fluorophenyl)-1H-imidazol-2-yl)-2-cyclopropylethyl)-5-(5-chloro-2-(1H-tetrazol-1-yl)phenyl)pyridine 1-oxide, fast eluting isomer (Example 51) and 2-(1-(5-(3-carboxy-2-fluorophenyl)-1H-imidazol-2-yl)-2-cyclopropylethyl)-5-(5-chloro-2-(1H-tetrazol-1-yl)phenyl)pyridine 1-oxide, slow eluting isomer (Example 52).

Example 51

$^1$H NMR (CD$_3$OD, 400 MHz): 9.36 (s, 1H), 8.22 (br. s., 1H), 8.02 (s, 1H), 7.63-7.84 (m, 3H), 7.55 (d, J=8.6 Hz, 2H), 7.45 (br. s., 1H), 7.14-7.29 (m, 2H), 5.19 (br. s., 1H), 2.19 (s, 1H), 1.96 (d, J=7.0 Hz, 1H), 0.73 (s, 1H), 0.40 (br. s., 1H), 0.08 (br. s., 1H), 0.01 (s, 1H).

MS (ESI) m/z: 546.1 (M+H).

Example 52

$^1$H NMR (CD$_3$OD, 400 MHz): 9.36 (s, 1H), 8.21 (br. s., 1H), 7.93 (br. s., 1H), 7.72-7.81 (m, 2H), 7.68 (d, J=8.6 Hz, 1H), 7.60 (br. s., 1H), 7.54 (d, J=8.2 Hz, 1H), 7.43 (br. s., 1H), 7.19 (t, J=9.0 Hz, 2H), 5.03 (br. s., 1H), 2.19 (br. s., 1H), 1.93 (d, J=14.1 Hz, 1H), 0.72 (br. s., 1H), 0.38 (d, J=7.4 Hz, 2H), 0.08 (br. s., 1H), 0.02 (br. s., 1H).

MS (ESI) m/z: 546.1 (M+H).

By using procedures similar to those described above, and appropriate starting materials, the following compounds were synthesized and characterized by LC/MS.

| Ex | Structure | Chiral Separation | Exact Mass [M + H]+ | F11a IC50 nM | PK IC50 nM |
|---|---|---|---|---|---|
| 51 | 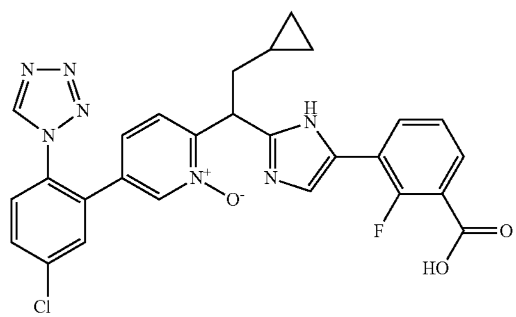 [SMILES: O=C(O)c1cccc(-c2cnc(C(CC3CC3)c3ccc(-c4cc(Cl)ccc4-n4cnnn4)c[n+]3[O-])[nH]2)c1F] | AD column Fast eluting isomer | 546 | 0.87 | 80 |
| 52 | 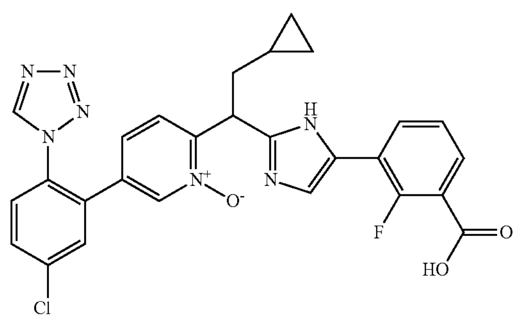 [SMILES: O=C(O)c1cccc(-c2cnc(C(CC3CC3)c3ccc(-c4cc(Cl)ccc4-n4cnnn4)c[n+]3[O-])[nH]2)c1F] | AD column slow eluting isomer | 546 | 204 | |
| 53 | 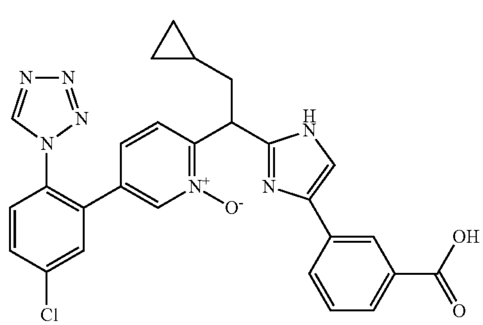 [SMILES: O=C(O)c1cccc(-c2c[nH]c(C(CC3CC3)c3ccc(-c4cc(Cl)ccc4-n4cnnn4)c[n+]3[O-])n2)c1] | IA column, fast eluting isomer | 528 | 0.90 | 62 |

| Ex | Structure | Chiral Separation | Exact Mass [M + H]+ | F11a IC50 nM | PK IC50 nM |
|---|---|---|---|---|---|
| 54 | 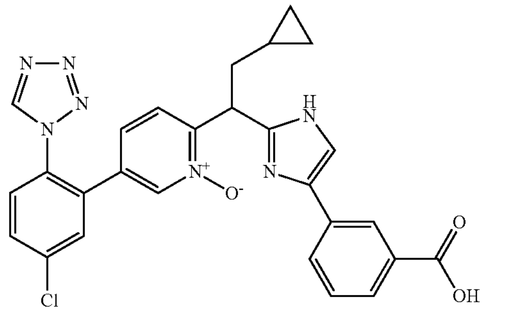 [SMILES: O=C(O)c1cccc(-c2c[nH]c(C(CC3CC3)c3ccc(-c4cc(Cl)ccc4-n4cnnn4)c[n+]3[O-])n2)c1] | IA column, slow eluting isomer | 528 | 71 | |
| 55 | 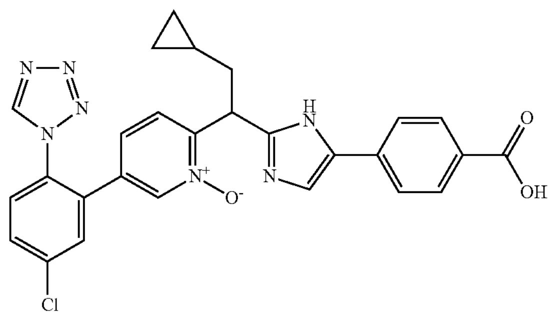 [SMILES: O=C(O)c1ccc(-c2cnc(C(CC3CC3)c3ccc(-c4cc(Cl)ccc4-n4cnnn4)c[n+]3[O-])[nH]2)cc1] | Fast eluting isomer | 528 | 593 | |
| 56 | 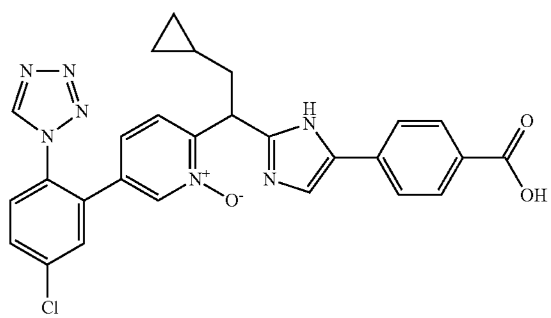 [SMILES: O=C(O)c1ccc(-c2cnc(C(CC3CC3)c3ccc(-c4cc(Cl)ccc4-n4cnnn4)c[n+]3[O-])[nH]2)cc1] | slow eluting isomer | 528 | 11 | 241 |
Examples 57 and 58
2-(1-(5-(5-carboxy-4-fluorothiophen-3-yl)-1H-imidazol-2-yl)-2-cyclopropylethyl)-5-(5-chloro-2-(1H-tetrazol-1-yl)phenyl)pyridine 1-oxide
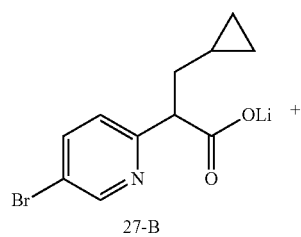
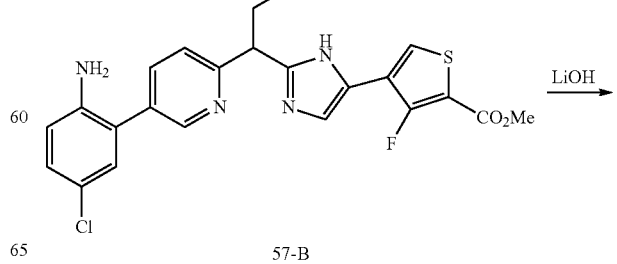

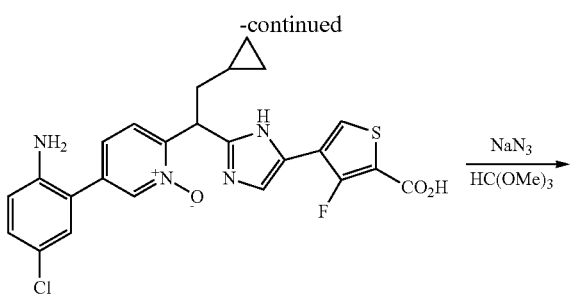

57-C

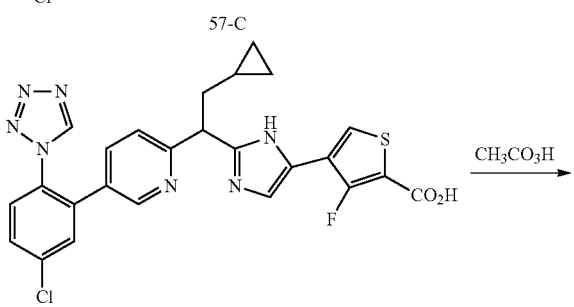

57-D

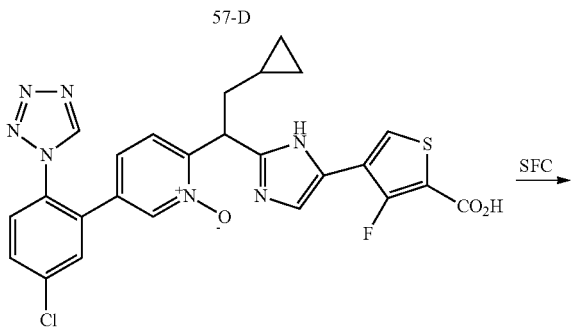

57-E

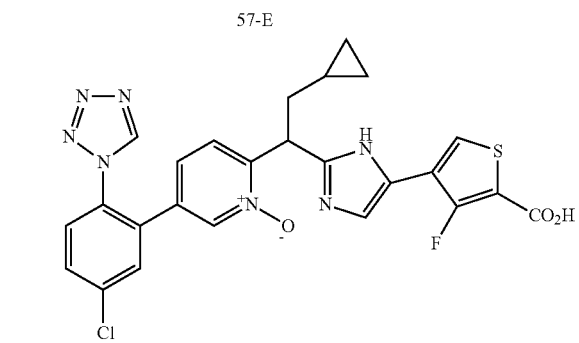

Example 57 (enantiomer 1)
Example 58 (enantiomer 2)

Step 1: methyl 4-(2-(1-(5-(2-amino-5-chlorophenyl) pyridin-2-yl)-2-cyclopropylethyl)-1H-imidazol-5-yl)-3-fluorothiophene-2-carboxylate (57-B)

Intermediate (57-B) was prepared in 3 steps by using procedures similar to those described for example 27-F.

Step 2: 4-(2-(1-(5-(2-amino-5-chlorophenyl)pyridin-2-yl)-2-cyclopropylethyl)-1H-imidazol-5-yl)-3-fluorothiophene-2-carboxylic acid (57-C)

Lithium hydroxide anhydrate (0.25 g, 6.0 mmol) was added to a solution of methyl 4-(2-(1-(5-(2-amino-5-chlorophenyl)pyridin-2-yl)-2-cyclopropylethyl)-1H-imidazol-5-yl)-3-fluorothiophene-2-carboxylate (0.6 g, 1.2 mmol) in MeOH (6 ml), THF (3 ml) and water (3 ml), followed by stirring at 50° C. for 90 min. The mixture was neutralized with 4M HCl in dioxane (1.81 ml, 7.24 mmol) and concentrated under reduced pressure and the residue was purified by column chromatography on a silica gel (40 g prepacked column), eluting with 0-20% MeOH/CH$_2$Cl$_2$ to give the title compound. MS (ESI) m/z 483.05 (M+H).

Step 3: 4-(2-(1-(5-(5-chloro-2-(1H-tetrazol-1-yl) phenyl)pyridin-2-yl)-2-cyclopropylethyl)-1H-imidazol-5-yl)-3-fluorothiophene-2-carboxylic acid (57-D)

To a solution of 4-(2-(1-(5-(2-amino-5-chlorophenyl) pyridin-2-yl)-2-cyclopropylethyl)-1H-imidazol-5-yl)-3-fluorothiophene-2-carboxylic acid in acetic acid (10 ml) was added sodium azide (0.47 g, 7.20 mmol) and trimethyl orthoformate (0.80 ml, 7.20 mmol) at RT. The flask was capped and the mixture was stirred at rt for overnight. The solvent was removed under reduced pressure and the residue was purified by column chromatography (prepacked 12 g silica-gel column), eluting with 0-15% MeOH/CH$_2$Cl$_2$ to give the title compound. MS (ESI) m/z 536.07 (M+H).

Step 4: 2-(1-(5-(5-carboxy-4-fluorothiophen-3-yl)-1H-imidazol-2-yl)-2-cyclopropylethyl)-5-(5-chloro-2-(1H-tetrazol-1-yl)phenyl)pyridine 1-oxide (57-E, Example 57 and 58)

Peracetic acid (0.67 ml, 4.03 mmol) was added to a solution of 4-(2-(1-(5-(5-chloro-2-(1H-tetrazol-1-yl)phenyl) pyridin-2-yl)-2-cyclopropylethyl)-1H-imidazol-5-yl)-3-fluorothiophene-2-carboxylic acid (0.36 g, 0.67 mmol) in acetic acid (6 ml) in a flask, which was then capped. The mixture was stirred at rt for 24 h. The solvent was removed under reduced pressure and the residue was purified by column chromatography (prepacked 40 g silica-gel column), eluting with 0-15% MeOH/CH$_2$Cl$_2$ to give the racemic product (57-E), which was separated by chiral SFC on AD-H column, eluting with 35% isopropanol/CO$_2$ to give 2-(1-(5-(5-carboxy-4-fluorothiophen-3-yl)-1H-imidazol-2-yl)-2-cyclopropylethyl)-5-(5-chloro-2-(1H-tetrazol-1-yl)phenyl) pyridine 1-oxide, fast eluting enantiomer (Example 57), MS (ESI) m/z 552.10 (M+H), and 2-(1-(5-(5-carboxy-4-fluorothiophen-3-yl)-1H-imidazol-2-yl)-2-cyclopropylethyl)-5-(5-chloro-2-(1H-tetrazol-1-yl)phenyl)pyridine 1-oxide, slow eluting enantiomer (Example 58), MS (ESI) m/z 552.10 (M+H).

Examples 59 and 60

2-(1-(5-(5-carbamoyl-4-fluorothiophen-3-yl)-1H-imidazol-2-yl)-2-cyclopropylethyl)-5-(5-chloro-2-(1H-tetrazol-1-yl)phenyl)pyridine 1-oxide (Examples 59 and 60)

Step 1: 4-(2-(1-(5-(5-chloro-2-(1H-tetrazol-1-yl) phenyl)pyridin-2-yl)-2-cyclopropylethyl)-1H-imidazol-5-yl)-3-fluorothiophene-2-carboxamide (59-B)

A mixture of 4-(2-(1-(5-(5-chloro-2-(1H-tetrazol-1-yl) phenyl)pyridin-2-yl)-2-cyclopropylethyl)-1H-imidazol-5-yl)-3-fluorothiophene-2-carboxylic acid (0.15 g, 0.28 mmol), ammonium chloride (0.08 g, 1.40 mmol), HATU (0.16 g, 0.42 mmol) and Hunig's Base (0.34 ml, 1.96 mmol) in DMF (2 ml) was stirred at RT for 2 h. The solvent was removed under reduced pressure and the residue was purified by column chromatography (prepacked 12 g silica-gel column), eluting with 0-60% MeOH/CH$_2$Cl$_2$ to give the title compound. MS (ESI) m/z 535.21 (M+H).

Step 2: 2-(1-(5-(5-carbamoyl-4-fluorothiophen-3-yl)-1H-imidazol-2-yl)-2-cyclopropylethyl)-5-(5-chloro-2-(1H-tetrazol-1-yl)phenyl)pyridine 1-oxide (Example 59 and 60)

A vial was charged with 4-(2-(1-(5-(5-chloro-2-(1H-tetrazol-1-yl)phenyl)pyridin-2-yl)-2-cyclopropylethyl)-1H-imidazol-5-yl)-3-fluorothiophene-2-carboxamide (84 mg, 0.16 mmol), peracetic acid (0.16 ml, 0.94 mmol) and acetic acid (2 ml), then was capped. The reaction mixture was stirred at RT for 24 h. The solvent was removed under reduced pressure and the residue was purified by column chromatography (prepacked 24 g silica-gel column), eluting with 0-60% MeOH/CH$_2$Cl$_2$ to give the racemic product, which was then separated by SFC on chiral WhelkO-1 column, eluting with MeOH/CO$_2$ (with 0.25% isopropylamine) to give 2-(1-(5-(5-carbamoyl-4-fluorothiophen-3-yl)-1H-imidazol-2-yl)-2-cyclopropylethyl)-5-(5-chloro-2-(1H-tetrazol-1-yl)phenyl)pyridine 1-oxide, fast eluting enantiomer (example 59), MS (ESI) m/z 551.02 (M+H), and 2-(1-(5-(5-carbamoyl-4-fluorothiophen-3-yl)-1H-imidazol-2-yl)-2-cyclopropylethyl)-5-(5-chloro-2-(1H-tetrazol-1-yl)phenyl)pyridine 1-oxide, slow eluting enantiomer (Example 60), MS (ESI) m/z 551.02 (M+H).

Examples 61 and 62

Methyl 4-[2-(1-{5-[5-chloro-2-(1H-tetrazol-1-yl)phenyl]-1-oxidopyridin-2-yl}-2-cyclopropylethyl)-1H-imidazol-5-yl]-3-fluorothiophene-2-carboxylate (Examples 61 and 62)

Examples 61 and 62 were prepared by using procedures similar to those described for Examples 27 and 28.

| Ex | Structure | Chiral Separation | Exact Mass [M + H]+ | F11a IC50 nM | PK IC50 nM |
|---|---|---|---|---|---|
| 57 | 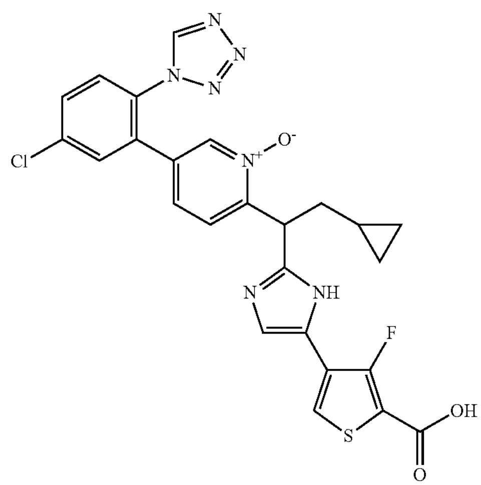 [SMILES: O=C(O)c1scc(-c2cnc(C(CC3CC3)c3ccc(-c4cc(Cl)ccc4-n4cnnn4)c[n+]3[O-])[nH]2)c1F] | AD-H column, fast eluting isomer | 552 | 1.5 | 58 |
| 58 | 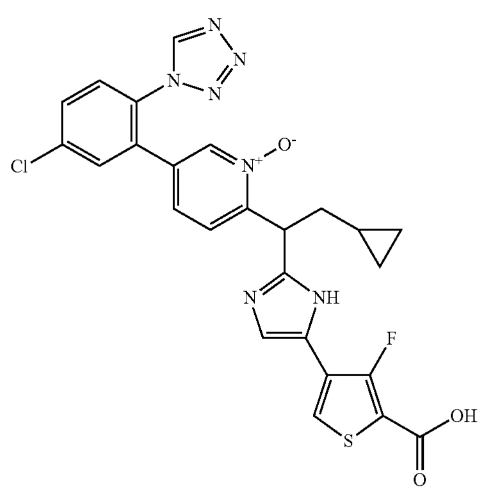 [SMILES: O=C(O)c1scc(-c2cnc(C(CC3CC3)c3ccc(-c4cc(Cl)ccc4-n4cnnn4)c[n+]3[O-])[nH]2)c1F] | AD-H column, slow eluting isomer | 552 | 11.8 | 1048 |

-continued

| Ex | Structure | Chiral Separation | Exact Mass [M + H]+ | F11a IC50 nM | PK IC50 nM |
|---|---|---|---|---|---|
| 59 | 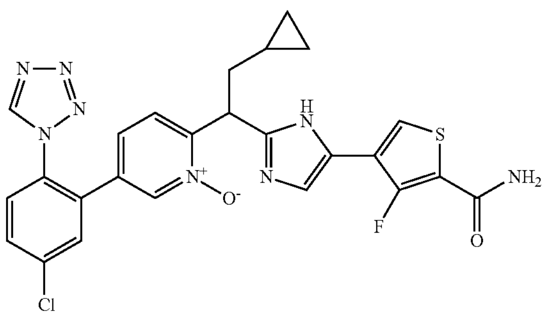 [SMILES: NC(=O)c1scc(-c2cnc(C(CC3CC3)c3ccc(-c4cc(Cl)ccc4-n4cnnn4)c[n+]3[O-])[nH]2)c1F] | WhelkO-1 column, Fast eluting isomer | 551 | 110 | |
| 60 | 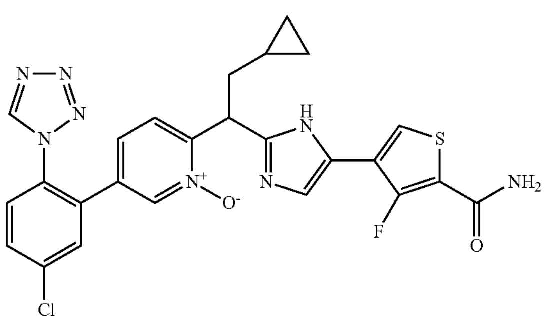 [SMILES: NC(=O)c1scc(-c2cnc(C(CC3CC3)c3ccc(-c4cc(Cl)ccc4-n4cnnn4)c[n+]3[O-])[nH]2)c1F] | WhelkO-1 column, slow eluting isomer | 551 | 4.9 | 76 |
| 61 | 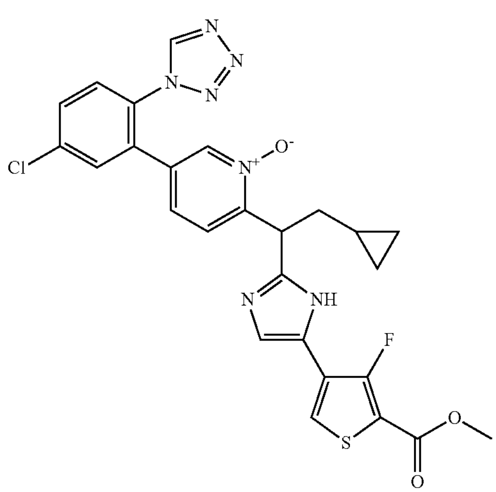 [SMILES: COC(=O)c1scc(-c2cnc(C(CC3CC3)c3ccc(-c4cc(Cl)ccc4-n4cnnn4)c[n+]3[O-])[nH]2)c1F] | AS-H column, Fast eluting isomer | 566 | 53 | 343 |

| Ex | Structure | Chiral Separation | Exact Mass [M + H]+ | F11a IC50 nM | PK IC50 nM |
|----|-----------|-------------------|---------------------|--------------|------------|
| 62 | 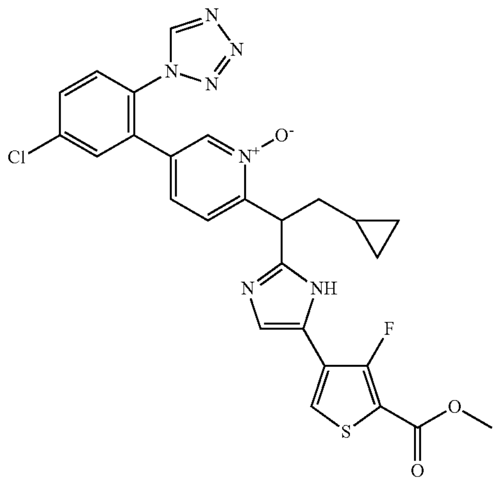 [SMILES: COC(=O)c1scc(-c2cnc(C(CC3CC3)c3ccc(-c4cc(Cl)ccc4-n4cnnn4)c[n+]3[O-])[nH]2)c1F] | AS-H column, slow eluting isomer | 566 | 1000 | |

Examples 63 and 64

5-(3-chloro-2-fluoro-6-(1H-tetrazol-1-yl)phenyl)-2-(2-cyclopropyl-1-(4-(4-((methoxycarbonyl) amino) phenyl)-1H-imidazol-2-yl)ethyl)pyridine 1-oxide (Examples 63 and 64)

Step 1: methyl 2-(5-(6-((tert-butoxycarbonyl) amino)-3-chloro-2-fluorophenyl)pyridin-2-yl)-3-cyclopropylpropanoate (63-B)

4,4,4',4',5,5,5',5'-Octamethyl-2,2'-bi(1,3,2-dioxaborolane) (600 mg, 2.3 mmol), [1,1'-bis(diphenylphosphino)ferrocene]dichloropalladium(II) (344 mg, 0.47 mmol), and potassium acetate (690 mg, 7.0 mmol) were mixed in a microwave reaction vial. The vial was then capped. Air was removed by vacuum and back-filled with nitrogen (×3). Ethyl 2-(5-bromopyridin-2-yl)-3-cyclopropylpropanoate (700 mg, 2.348 mmol) in 1,4-dioxane (10 ml) was added. The mixture was heated to 110° C. for 1 hour. After it was cooled to room temperature, tert-butyl (4-chloro-3-fluoro-2-iodophenyl)carbamate (870 mg, 2.3 mmol), [1,1'-bis(diphenylphosphino)ferrocene]dic hloropalladium(II) (170 mg, 0.24 mmol), and K$_2$CO$_3$ (1M, 7.04 ml, 7.04 mmol) were added, then it was heated to 100° C. for 2 hours. The mixture was diluted with ethyl acetate, and filtered. The organic layer was separated and dried over anhydrous sodium sulfate. After it was filtered and concentrated, the crude was purified by column chromatography on silica gel Isolute Flash Si; 100 g prepacked, eluting with gradient 0~70% EtOAc/isohexane to give the product. MS (ESI) m/z 499 (M+H).

Step 2: 2-(5-(6-((tert-butoxycarbonyl)amino)-3-chloro-2-fluorophenyl)pyridin-2-yl)-3-cyclo propyl-propanoic acid, lithium salt (63-C)

Methyl 2-(5-(6-((tert-butoxycarbonyl)amino)-3-chloro-2-fluorophenyl)pyridin-2-yl)-3-cyclopropylpropanoate (63-B, 820 mg, 1.8 mmol) in MeOH (6 ml) was mixed with LiOH (1M, 2.74 ml, 2.74 mmol) and heated to 50° C. for 1 hour. The mixture was then concentrated, and further dried in a vacuum oven at 50° C. overnight. The product was used in the next step without further purification. MS (ESI) m/z 435 (M+H).

Step 3: 2-(4-((methoxycarbonyl)amino)phenyl)-2-oxoethyl 2-(5-(6-((tert-butoxycarbonyl) amino)-3-chloro-2-fluorophenyl)pyridin-2-yl)-3-cyclopropylpropanoate (63-D)

Lithium 2-(5-(6-((tert-butoxycarbonyl)amino)-3-chloro-2-fluorophenyl)pyridin-2-yl)-3-cyclopropylpropanoate (63-C, 793 mg, 1.8 mmol) in DMF (5.5 ml) was mixed with methyl (4-(2-chloroacetyl)phenyl)carbamate (410 mg, 1.8 mmol) and heated to 50° C. for 5 hours. The mixture was concentrated by rotavapor. The product was taken up with ethyl acetate (50 mL), and washed with brine. The organic layer was separated, and dried over anhydrous sodium sulfate. After it was filtered, and concentrated, the crude was purified by column chromatography on silica gel Isolute Flash Si; 50 g prepacked, eluting with gradient 0~50% EtOAc/isohexane to give the product. MS (ESI) m/z 626 (M+H).

Step 4: tert-Butyl (4-chloro-2-(6-(2-cyclopropyl-1-(5-(4-((methoxycarbonyl)amino)phenyl)-1H-imidazol-2-yl)ethyl)pyridin-3-yl)phenyl)carbamate (63-E)

2-(4-((Methoxycarbonyl)amino)phenyl)-2-oxoethyl 2-(5-(6-((tert-butoxycarbonyl)amino)-3-chloro-2-fluorophenyl) pyridin-2-yl)-3-cyclopropylpropanoate (63-D, 800 mg, 1.3 mmol) in toluene (5.5 ml) was mixed with ammonium acetate (990 mg, 13 mmol) and acetic acid (0.2 ml, 3.8 mmol), then heated to 100° C. for 15 hours. The mixture was diluted with ethyl acetate (100 mL), and washed with saturated NaHCO$_3$ solution, and brine. The solution was dried over anhydrous sodium sulfate. After it was filtered and concentrated, the crude was purified by column chromatography on silica gel Isolute Flash Si; 100 g prepacked, eluting with 0~8% gradient CH$_2$Cl$_2$/MeOH to give the product. MS (ESI) m/z 606 (M+H).

Step 5: 5-(6-((tert-butoxycarbonyl)amino)-3-chloro-2-fluorophenyl)-2-(2-cyclopropyl-1-(4-(4-((methoxycarbonyl)amino)phenyl)-1H-imidazol-2-yl)ethyl)pyridine 1-oxide (63-F)

Intermediate 63-E (570 mg, 0.94 mmol) in acetic acid (6 ml) was mixed with peracetic acid (1.56 ml, 9.4 mmol). The mixture was stirred at room temperature overnight. Toluene was added and the mixture was concentrated. The crude was purified by column chromatography on silica gel Isolute Flash Si; 50 g prepacked, eluting with first with 0~10% $CH_2Cl_2$/MeOH to give the titled product, then eluting with 3~10% $CH_2Cl_2$/MeOH/$NH_3$(Aq.) to give another portion of the titled product. MS (ESI) m/z 622 (M+H).

Step 6: 5-(6-amino-3-chloro-2-fluorophenyl)-2-(2-cyclopropyl-1-(4-(4-((methoxycarbonyl) amino) phenyl)-1H-imidazol-2-yl)ethyl)pyridine 1-oxide (63-G)

5-(6-((tert-butoxycarbonyl)amino)-3-chloro-2-fluorophenyl)-2-(2-cyclopropyl-1-(4-(4-((methoxycarbonyl)amino) phenyl)-1H-imidazol-2-yl)ethyl)pyridine 1-oxide (63-F, 470 mg, 0.756 mmol) in DCM (4 ml) was mixed with TFA (4 ml). The mixture was stirred at room temperature for 30 minutes. Toluene was added and the mixture was concentrated. The crude was used in the next step without further purification. MS (ESI) m/z 522 (M+H).

Step 7: 5-(3-chloro-2-fluoro-6-(1H-tetrazol-1-yl) phenyl)-2-(2-cyclopropyl-1-(4-(4-((methoxycarbonyl)amino)phenyl)-1H-imidazol-2-yl)ethyl)pyridine 1-oxide (Example 63 and 64)

5-(6-amino-3-chloro-2-fluorophenyl)-2-(2-cyclopropyl-1-(4-(4-((methoxycarbonyl)amino) phenyl)-1H-imidazol-2-yl)ethyl)pyridine 1-oxide (390 mg, 0.75 mmol) was mixed with sodium azide (293 mg, 4.50 mmol) and trimethyl orthoformate (0.5 ml, 4.5 mmol). The flask was capped. Acetic acid (4 ml) was then added with a syringe. The resulting mixture was stirred at room temperature overnight. Toluene was added and the mixture was concentrated. The crude was diluted with ethyl acetate (100 mL) and washed with saturated $NaHCO_3$ solution, and brine. After it was dried over anhydrous sodium sulfate, the mixture was filtered, and the solution was concentrated. The crude was purified by column chromatography on silica gel Isolute Flash Si; 100 g prepacked, eluting with first with 0~10% $CH_2Cl_2$/MeOH to give the racemic product after the fractions were concentrated. The racemic product was separated by SFC on a IC chiral column, eluting with 65% 2:1 MeOH: MeCN/$CO_2$ to give 5-(3-chloro-2-fluoro-6-(1H-tetrazol-1-yl)phenyl)-2-(2-cyclopropyl-1-(4-(4-((methoxycarbonyl) amino)phenyl)-1H-imidazol-2-yl)ethyl)pyridine 1-oxide, fast eluting enantiomer (Example 63), MS (ESI) m/z 575 (M+H), and 5-(3-chloro-2-fluoro-6-(1H-tetrazol-1-yl)phenyl)-2-(2-cyclopropyl-1-(4-(4-((methoxycarbonyl)amino) phenyl)-1H-imidazol-2-yl)ethyl)pyridine 1-oxide, fast eluting enantiomer (Example 64), MS (ESI) m/z 575 (M+H).

Example 65

5-(5-Chloro-2-(1H-1,2,3-triazol-1-yl)phenyl)-2-(2-cyclopropyl-1-(5-(4-((methoxycarbonyl)amino)phenyl)-1H-imidazol-2-yl)ethyl)pyridine 1-oxide Step 1: 5-bromo-2-(2-cyclopropyl-1-(5-(4-((methoxycarbonyl)amino)phenyl)-1H-imidazol-2-yl)ethyl)pyridine 1-oxide (65-B)

To a solution of methyl (4-(2-(1-(5-bromopyridin-2-yl)-2-cyclopropylethyl)-1H-imidazol-5-yl)phenyl)carbamate (1.1 g, 2.5 mmol) in DCM (20 mL) was added mCPBA (0.61 g, 2.5 mmol) at 0° C. The mixture was stirred at 20° C. for 12 h under $N_2$ atmosphere. The mixture was quenched with sat. $Na_2SO_3$ (20 mL) and extracted with EtOAc (20 mL×4). The combined EtOAc extracts were dried over sodium sulfate and concentrated. The residue was purified by chromatography column ($SiO_2$, PE/EA=1:2) to give the title compound. MS (ESI) m/z 459.1 (M+H).

Step 2: 5-bromo-2-(2-cyclopropyl-1-(5-(4-((methoxycarbonyl)amino)phenyl)-1-((2-(trimethyl silyl)ethoxy)methyl)-1H-imidazol-2-yl)ethyl)pyridine 1-oxide (65-C)

To a solution of 5-bromo-2-(2-cyclopropyl-1-(5-(4-((methoxycarbonyl)amino)phenyl)-1H-imidazol-2-yl)ethyl) pyridine 1-oxide (65-B) (860 mg, 1.9 mmol) in DCM (10 mL) was added SEM-Cl (0.43 mL, 2.4 mmol) at 0° C. and then DIPEA (0.66 mL, 3.8 mmol) was added. The mixture was stirred at 0° C. for 3 h under $N_2$ atmosphere. The mixture was quenched with sat. $NaHCO_3$ (20 mL) and extracted with EtOAc (20 mL×2). The combined EtOAc extracts were dried over sodium sulfate and concentrated. The residue was purified by chromatography column ($SiO_2$, PE/EtOAc=20:1) to give the title compound. MS (ESI) m/z 489.2 (M+H).

Step 3: 5-(5-chloro-2-(1H-1,2,3-triazol-1-yl)phenyl)-2-(2-cyclopropyl-1-(5-(4((methoxycarbonyl) amino)phenyl)-1-((2-(trimethylsilyl)ethoxy)methyl)-1H-imidazol-2-yl)ethyl)pyridine 1-oxide (65-E)

To a microwave tube was added 5-bromo-2-(2-cyclopropyl-1-(5-(4-((methoxycarbonyl) amino)phenyl)-1-((2-(trimethylsilyl)ethoxy)methyl)-1H-imidazol-2-yl)ethyl)pyridine 1-oxide (65-C) (154 mg, 0.26 mmol), 1-(4-chloro-2-(trimethylstannyl)phenyl)-1H-1,2,3-triazole (65-D) (90 mg, 0.263 mmol), toluene (2.5 mL) and tetrakis(triphenylphosphine)palladium (60.7 mg, 0.053 mmol). The reaction mixture was stirred at 150° C. for 50 min under microwave irradiation. After it was cooled to RT, the mixture was filtered and concentrated. The residue was purified by prep-TLC ($SiO_2$, PE:EtOAc=1:3) to give the title compound. MS (ESI) m/z 686.3 (M+H).

Step 4: 5-(5-chloro-2-(1H-1,2,3-triazol-1-yl)phenyl)-2-(2-cyclopropyl-1-(5-(4-((methoxy carbonyl) amino)phenyl)-1H-imidazol-2-yl)ethyl)pyridine 1-oxide (Example 65)

To a round bottom flask was added 5-(5-chloro-2-(1H-1,2,3-triazol-1-yl)phenyl)-2-(2-cyclopropyl-1-(5-(4-((methoxycarbonyl)amino)phenyl)-1-((2-(trimethylsilyl) ethoxy)methyl)-1H-imidazol-2-yl)ethyl)pyridine 1-oxide (65-E) (50 mg, 0.035 mmol), DCM (3 mL) and TFA (1 mL). The reaction mixture was stirred at 25° C. for 18 h. The mixture was concentrated. The residue was purified by prep-HPLC to give the title compound. $^1$H NMR (CD$_3$OD, 400 MHz): 8.20 (d, J=15.4 Hz, 2H) 7.78 (d, J=19.4 Hz, 3H) 7.65-7.72 (m, 3H) 7.60 (s, 4H) 7.28 (d, J=8.2 Hz, 1H) 4.95 (br. s., 1H) 3.75 (s, 3H) 2.28-2.36 (m, 1H) 2.07-2.15 (m, 1H) 0.69 (br. s., 1H) 0.46 (br. s., 2H) 0.12 (d, J=4.4 Hz, 1H) −0.05-0.01 (m, 1H). MS (ESI) m/z 556.2 (M+H).

Example 66

5-(5-chloro-2-(4H-1,2,4-triazol-4-yl)phenyl)-2-(2-cyclopropyl-1-(5-(4-((methoxycarbonyl)amino)phenyl)-1H-imidazol-2-yl)ethyl)pyridine 1-oxide

Step 1: 5-(2-amino-5-chlorophenyl)-2-(2-cyclopropyl-1-(5-(4-((methoxycarbonyl)amino)phenyl)-1H-imidazol-2-yl)ethyl)pyridine 1-oxide (66-B)

To a round bottom flask was added 5-bromo-2-(2-cyclopropyl-1-(5-(4-((methoxycarbonyl)amino)phenyl)-1H-imidazol-2-yl)ethyl)pyridine 1-oxide (65-B) (650 mg, 1.4 mmol), 4-chloro-2-(4,4,5,5-tetramethyl-1,3,2-dioxaborolan-2-yl)aniline (410 mg, 1.6 mmol), 1,1'-bis(di-tert-butylphosphino)ferrocene palladium dichloride (190 mg, 0.28 mmol), $K_3PO_4$ (754 mg, 3.55 mmol), THF (15 mL) and water (3 mL). The reaction mixture was stirred at 50° C. for 18 h. The mixture was filtered and concentrated. The residue was purified by normal phase chromatography (ISCO, $SiO_2$, 12 g Agela Flash column, 0-75% EtOAc/PE, 40 min, dry loaded) to give the title compound. $^1$H NMR (CD$_3$OD, 400 MHz): 8.38 (s, 1H), 7.67-7.73 (m, 1H), 7.52-7.64 (m, 3H), 7.44 (d, J=8.4 Hz, 2H), 7.27 (s, 1H), 7.03-7.14 (m, 2H), 6.78 (d, J=8.6 Hz, 1H), 5.10 (dd, J=9.0, 6.0 Hz, 1H), 3.73 (s, 3H), 2.15-2.25 (m, 1H), 2.05 (dd, J=13.2, 6.6 Hz, 1H), 0.78 (br. s., 1H), 0.44 (ddd, J=12.5, 8.2, 4.2 Hz, 2H), 0.20 (dd, J=8.7, 4.1 Hz, 1H), 0.02-0.12 (m, 1H). MS (ESI) m/z 504.2 (M+H).

Step 2: 5-(5-chloro-2-(4H-1,2,4-triazol-4-yl)phenyl)-2-(2-cyclopropyl-1-(5-(4-((methoxycarbonyl)amino)phenyl)-1H-imidazol-2-yl)ethyl)pyridine 1-oxide (Example 66)

To a round bottom flask was added 5-(2-amino-5-chlorophenyl)-2-(2-cyclopropyl-1-(5-(4-((methoxycarbonyl)amino)phenyl)-1H-imidazol-2-yl)ethyl)pyridine 1-oxide (66-B) (100 mg, 0.198 mmol), (1E,N'E)-N'-((dimethylamino)methylene)-N,N-dimethylformohydrazonamide dihydrochloride (213 mg, 0.992 mmol), 4-methylbenzenesulfonic acid hydrate (7.55 mg, 0.040 mmol) and toluene (4 mL) at 20° C. The reaction mixture was stirred at 120° C. for 5 h. The reaction mixture was filtered and concentrated. The residue was purified by prep-HPLC to give the title compound. $^1$H NMR (CD$_3$OD, 400 MHz): 8.68 (s, 2H), 8.37 (s, 1H), 7.71-7.83 (m, 4H), 7.60-7.70 (m, 5H), 7.36 (d, J=7.3 Hz, 1H), 5.00 (d, J=7.3 Hz, 1H), 3.79 (s, 3H), 2.33-2.41 (m, 1H), 2.13-2.21 (m, 1H), 0.73 (br. s., 1H), 0.50 (dd, J=8.5, 3.9 Hz, 2H), 0.15 (d, J=4.6 Hz, 1H), −0.01-0.05 (m, 1H). MS (ESI) m/z 556.1 (M+H).

By using procedures similar to those described above, and appropriate starting materials, the following compounds were synthesized and characterized by LC/MS.

| Ex | Structure | Chiral Separation | Exact Mass [M + H]+ | F11a IC50 nM | PK IC50 nM |
|---|---|---|---|---|---|
| 63 | 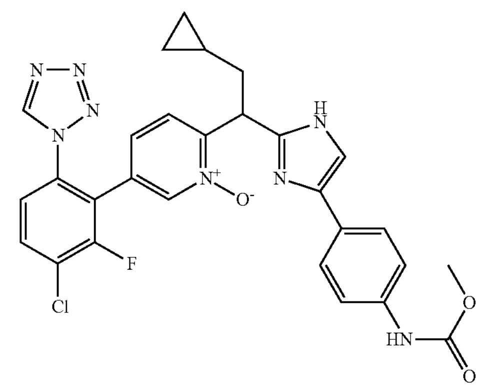 [SMILES: COC(=O)Nc1ccc(-c2c[nH]c(C(CC3CC3)c3ccc(-c4c(-n5cnnn5)ccc(Cl)c4F)c[n+]3[O-])n2)cc1] | IC column, Fast eluting isomer | 575 | 21.03 | 231 |
| 64 | 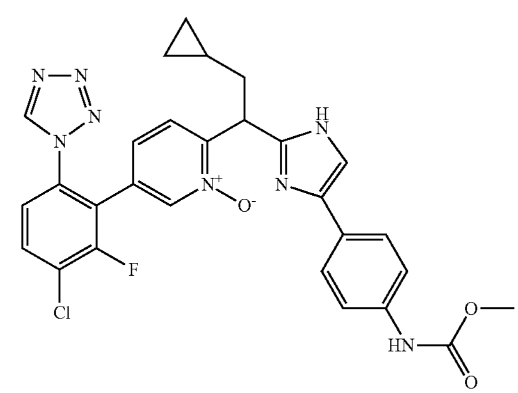 [SMILES: COC(=O)Nc1ccc(-c2c[nH]c(C(CC3CC3)c3ccc(-c4c(-n5cnnn5)ccc(Cl)c4F)c[n+]3[O-])n2)cc1] | IC column, slow eluting isomer | 575 | 0.22 | 5.60 |

-continued

| Ex | Structure | Chiral Separation | Exact Mass [M + H]+ | F11a IC50 nM | PK IC50 nM |
|---|---|---|---|---|---|
| 65 | 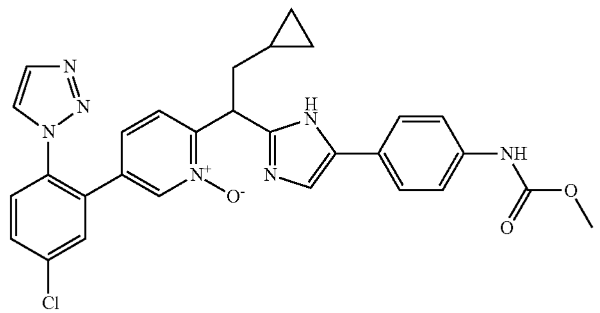 | racemic | 556 | 11.94 | |
| 66 | 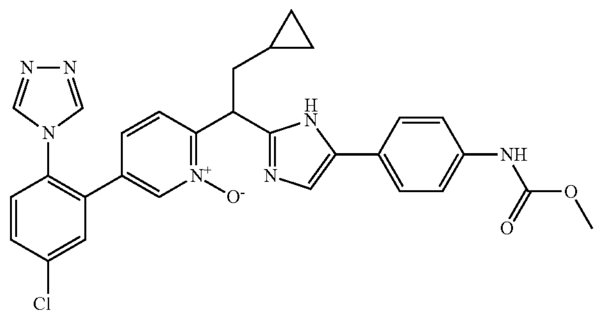 [SMILES: COC(=O)Nc1ccc(-c2cnc(C(CC3CC3)c3ccc(-c4cc(Cl)ccc4-n4cnnc4)c[n+]3[O-])[nH]2)cc1] | racemic | 556 | 12.89 | |
| 67 | 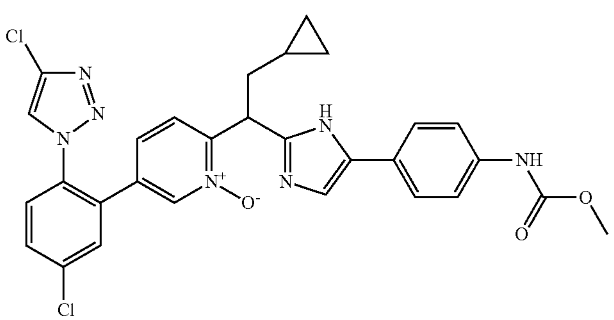 [SMILES: COC(=O)Nc1ccc(-c2cnc(C(CC3CC3)c3ccc(-c4cc(Cl)ccc4-n4cc(Cl)nn4)c[n+]3[O-])[nH]2)cc1] | racemic | 590 | 6.51 | 208 |
| 68 | 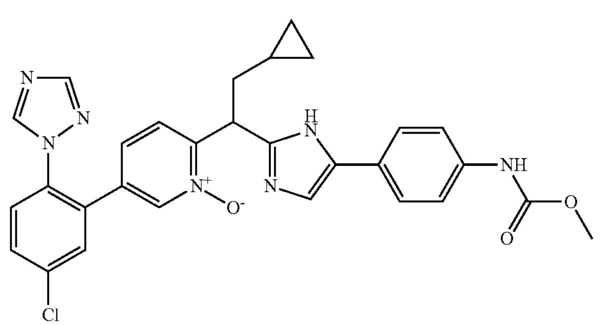 | racemic | 556 | 631 | |

-continued
| Ex | Structure | Chiral Separation | Exact Mass [M + H]+ | F11a IC50 nM | PK IC50 nM |
|---|---|---|---|---|---|
| 69 | 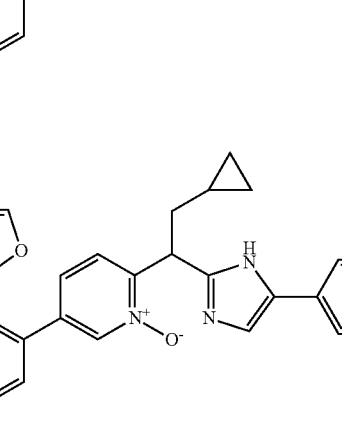 | Fast eluting isomer | 556 | 48 | 358 |
| 70 | 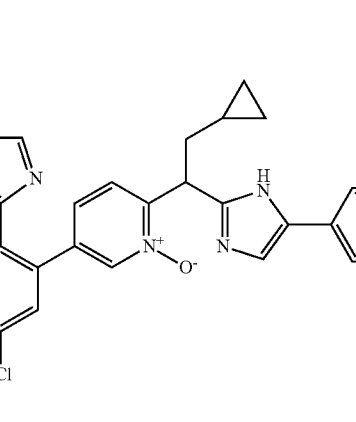 | Slow eluting isomer | 556 | 1000 | |
| 71 | 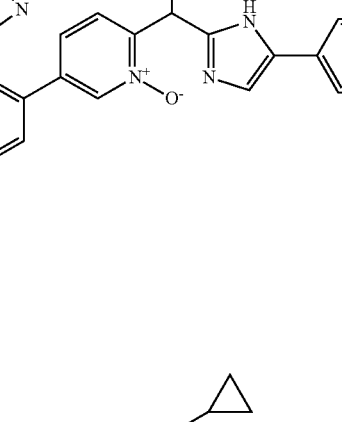 | racemic | 556 | 834 | |
| 72 | 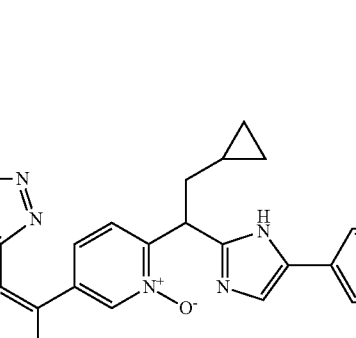 | racemic | 573 | 51.51 | 2613 |

-continued

| Ex | Structure | Chiral Separation | Exact Mass [M + H]+ | F11a IC50 nM | PK IC50 nM |
|---|---|---|---|---|---|
| 73 | 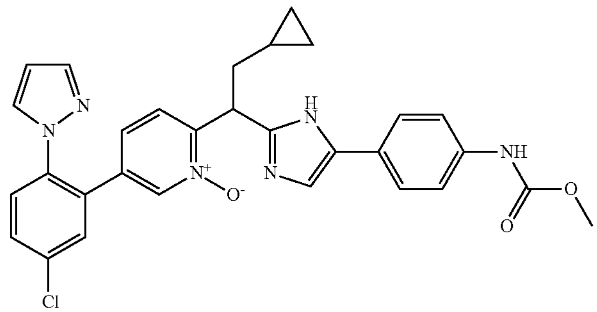 [SMILES: COC(=O)Nc1ccc(-c2cnc(C(CC3CC3)c3ccc(-c4cc(Cl)ccc4-n4cncn4)c[n+]3[O-])[nH]2)cc1] | racemic | 555 | 1000 | |
| 74 | 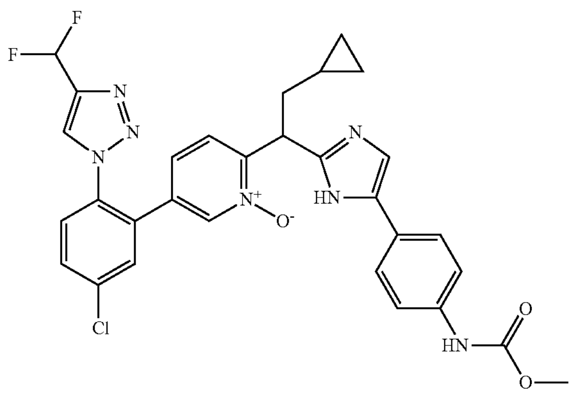 | racemic | 606 | 11 | |
| 75 | 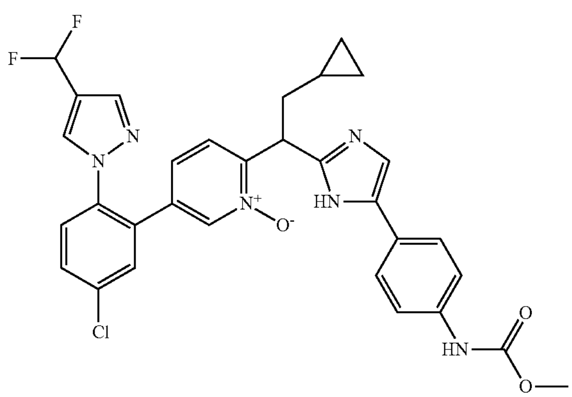 [SMILES: COC(=O)Nc1ccc(-c2cnc(C(CC3CC3)c3ccc(-c4cc(Cl)ccc4-n4cc(C(F)F)cn4)c[n+]3[O-])[nH]2)cc1] | racemic | 605 | 931 | |

Example 76 and 77 methyl {4-[2-(1-{5-[5-chloro-2-(1H-tetrazol-1-yl)phenyl]-1-oxidopyridin-2-yl}-2-cyclopropylethyl)-4-methyl-1H-imidazol-5-yl]phenyl}carbamate (Examples 76 and 77)

Step 1: 1-(4-((methoxycarbonyl)amino)phenyl)-1-oxopropan-2-yl 2-(5-bromopyridin-2-yl)-3-cyclopropylpropanoate (76-B)

Cesium carbonate (0.33 g, 1.00 mmol) was added to a mixture of lithium 2-(5-bromopyridin-2-yl)-3-cyclopropylpropanoate (0.55 g, 2.0 mmol) and methyl (4-(2-bromopropanoyl)phenyl) carbamate (0.69 g, 2.40 mmol) in DMF (10 ml). The mixture was stirred at 85° C. for 2 h, then the solid was filtered through celite and washed with EtOAc. The filtrate was concentrated under reduced pressure and the residue was purified by column chromatography on the silica-gel (prepacked 40 g silica-gel) with eluant 0-55% EtOAc/hexanr to give the title compound. MS (ESI) m/z 476.89 (M+H).

Step 2: methyl (4-(2-(1-(5-bromopyridin-2-yl)-2-cyclopropylethyl)-4-methyl-1H-imidazol-5-yl)phenyl)carbamate (76-C)

A pressure release vial was charged with 1-(4-((methoxycarbonyl)amino)phenyl)-1-oxopropan-2-yl 2-(5-bromopyridin-2-yl)-3-cyclopropylpropanoate (0.64 g, 1.35 mmol), ammonium sodium acetate (1.04 g, 13.46 mmol), acetic acid (0.75 ml) and toluene (15 ml). Then, the vial was capped, and the mixture was heated at 150° C. for 45 min under microwave. The mixture was concentrated under reduced pressure and the residue was purified by column chromatography on silica gel (Teledyne ISCO Si; 40 g prepacked), eluting with 0-90% EtOAc/hexane to give the title compound. MS (ESI) m/z 457.91 (M+H).

Step 3: methyl (4-(2-(1-(5-(2-amino-5-chlorophenyl)pyridin-2-yl)-2-cyclopropylethyl)-4-methyl-1H-imidazol-5-yl)phenyl)carbamate (76-D)

A flask was charged with methyl (4-(2-(1-(5-bromopyridin-2-yl)-2-cyclopropylethyl)-4-methyl-1H-imidazol-5-yl)phenyl)carbamate (0.28 g, 0.62 mmol), 4-chloro-2-(4,4,5,5-tetramethyl-1,3,2-dioxaborolan-2-yl)aniline (0.218 g, 0.86 mmol), potassium phosphate tribasic (0.26 g, 1.23 mmol), 1,1'-bis(di-tert-butylphosphino)ferrocene palladium dichloride (0.08 g, 0.12 mmol), and was then capped. Air was removed by vacuum and back-filled with $N_2$, followed by adding THF (10 ml) and qater (2 ml). The mixture was heated at 60° C. for 45 min in an oil bath. After cooling down, the reaction mixture was diluted with water and extracted with EtOAc (3×50 mL). The combined organic phase was dried over $MgSO_4$, filtered, concentrated and purified by flash chromatography on a silica-gel column (prepacked 40 g silica-gel column) with 0-90% EtOAc/$CH_2Cl_2$ to give the title compound. MS (ESI) m/z 502.18 (M+H).

Step 4: methyl (4-(2-(1-(5-(5-chloro-2-(1H-tetrazol-1-yl)phenyl)pyridin-2-yl)-2-cyclopropylethyl)-4-methyl-1H-imidazol-5-yl)phenyl)carbamate (76-E)

To a mixture of methyl (4-(2-(1-(5-(2-amino-5-chlorophenyl)pyridin-2-yl)-2-cyclopropylethyl)-4-methyl-1H-imidazol-5-yl)phenyl)carbamate (0.11 g, 0.22 mmol) in acetic acid (3 ml) was added sodium azide (0.09 g, 1.32 mmol) and trimethyl orthoformate (0.15 ml, 1.32 mmol). The flask was capped and the mixture was stirred at rt overnight. The solvent was removed under reduced pressure and the residue was purified by column chromatography (prepacked 12 g silica-gel column), eluting with 0-90% EtOAc/$CH_2Cl_2$ to give the title compound. MS (ESI) m/z 555.18 (M+H).

Step 5: 5-(5-chloro-2-(1H-tetrazol-1-yl)phenyl)-2-(2-cyclopropyl-1-(5-(4-((methoxycarbonyl)-amino)phenyl)-4-methyl-1H-imidazol-2-yl)ethyl)pyridine 1-oxide (Examples 76 and 77)

Peracetic acid (0.18 ml, 1.08 mmol) was added to a mixture of methyl (4-(2-(1-(5-(5-chloro-2-(1H-tetrazol-1-yl)phenyl)pyridin-2-yl)-2-cyclopropylethyl)-4-methyl-1H-imidazol-5-yl)phenyl)carbamate (0.10 g, 0.18 mmol) in acetic acid (2 ml), the flask was then capped and the mixture was stirred at rt for 24 h. The solvent was removed under reduced pressure and the residue was purified by column chromatography (prepacked 40 g silica-gel column), eluting with 0-12% MeOH/$CH_2Cl_2$ to give the racemic product, which was separated by SFC on chiral OD-H column, eluting with 35% MeOH (with 0.1% DEA)/$CO_2$ to give 5-(5-chloro-2-(1H-tetrazol-1-yl)phenyl)-2-(2-cyclopropyl-1-(5-(4-((methoxycarbonyl)-amino)phenyl)-4-methyl-1H-imidazol-2-yl)ethyl)pyridine 1-oxide, fast eluting enantiomer (Examples 76), MS (ESI) m/z 570.98 (M+H), and 5-(5-chloro-2-(1H-tetrazol-1-yl)phenyl)-2-(2-cyclopropyl-1-(5-(4-((methoxycarbonyl)-amino)phenyl)-4-methyl-1H-imidazol-2-yl)ethyl)pyridine 1-oxide, slow eluting enantiomer (Examples 77), MS (ESI) m/z 570.98 (M+H).

Examples 78 and 79

5-(5-chloro-2-(1H-tetrazol-1-yl)phenyl)-2-(1-(4-chloro-5-(4-((methoxycarbonyl)amino) phenyl)-1H-imidazol-2-yl)-2-cyclopropylethyl)pyridine 1-oxide (Example 78 and 79)

Step 1: methyl (4-(2-(1-(5-bromopyridin-2-yl)-2-cyclopropylethyl)-4-chloro-1H-imidazol-5-yl)phenyl)carbamate (78-B)

1,3-Dichloro-5,5-dimethylhydantoin (0.58 g, 2.9 mmol) was added to a solution of methyl (4-(2-(1-(5-bromopyridin-2-yl)-2-cyclopropylethyl)-1H-imidazol-5-yl)phenyl)carbamate (1.29 g, 2.92 mmol) in DCM (29.2 ml) at 0° C., and stirred for 30 min. The mixture was then concentrated under reduced pressure and the residue was taken up in $CH_2Cl_2$ and purified on a silica-gel column with 0-60% EtOAc/hexane to give 78-B. MS (ESI) m/z 476.9 (M+H).

Step 2: 5-(5-chloro-2-(1H-tetrazol-1-yl)phenyl)-2-(1-(4-chloro-5-(4-((methoxycarbonyl)amino) phenyl)-1H-imidazol-2-yl)-2-cyclopropylethyl)pyridine 1-oxide (Example 78 and 79)

By using procedures similar to steps 4-6 for Examples 27 and 28, the racemic product of Examples 78 and 79 was prepared from 78-B, which was separated by SFC on chiral OD column, eluting with 50% (2:1 MeOH:MeCN)/$CO_2$ to give 5-(5-chloro-2-(1H-tetrazol-1-yl)phenyl)-2-(1-(4-chloro-5-(4-((methoxycarbonyl)amino) phenyl)-1H-imidazol-2-yl)-2-cyclopropylethyl)pyridine 1-oxide, fast eluting enantiomer (Example 78), MS (ESI) m/z 591.1 (M+H), and 5-(5-chloro-2-(1H-tetrazol-1-yl)phenyl)-2-(1-(4-chloro-5-(4-((methoxycarbonyl)amino) phenyl)-1H-imidazol-2-yl)-2-cyclopropylethyl)pyridine 1-oxide, slow eluting enantiomer (Example 79), MS (ESI) m/z 591.1 (M+H).

By using procedures similar to those described above, and appropriate starting materials, the following compounds were synthesized and characterized by LC/MS.
| Ex | Structure | Chiral Separation | Exact Mass [M + H]+ | F11a IC50 nM | PK IC50 nM |
|---|---|---|---|---|---|
| 76 | 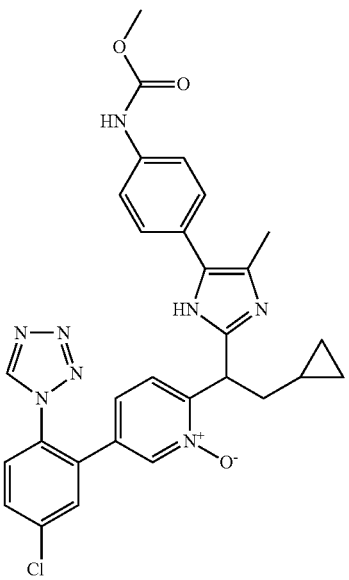 [SMILES: COC(=O)Nc1ccc(-c2[nH]c(C(CC3CC3)c3ccc(-c4cc(Cl)ccc4-n4cnnn4)c[n+]3[O-])nc2C)cc1] | OD-H column, fast eluting isomer | 571 | 36.79 | 802 |
| 77 | 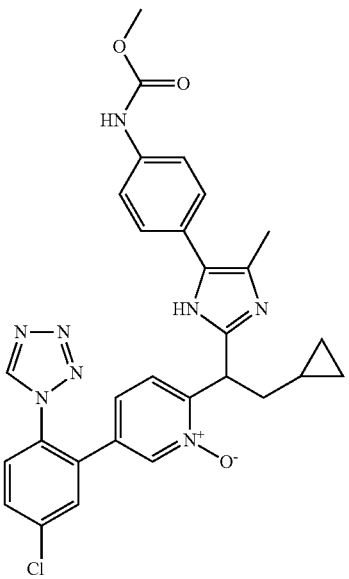 [SMILES: COC(=O)Nc1ccc(-c2[nH]c(C(CC3CC3)c3ccc(-c4cc(Cl)ccc4-n4cnnn4)c[n+]3[O-])nc2C)cc1] | OD-H column, slow eluting isomer | 571 | 1.52 | 48 |
| 78 | 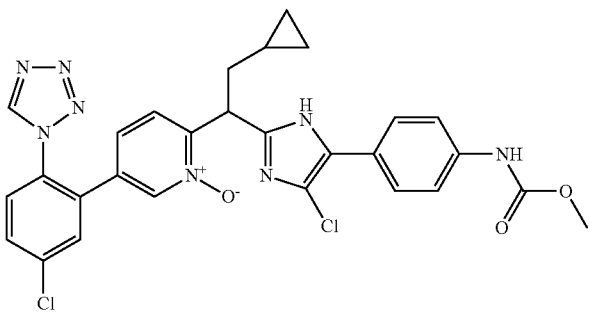 [SMILES: COC(=O)Nc1ccc(-c2[nH]c(C(CC3CC3)c3ccc(-c4cc(Cl)ccc4-n4cnnn4)c[n+]3[O-])nc2Cl)cc1] | OD column, fast eluting isomer | 591 | 54.37 | |

| Ex | Structure | Chiral Separation | Exact Mass [M + H]+ | F11a IC50 nM | PK IC50 nM |
|---|---|---|---|---|---|
| 79 | 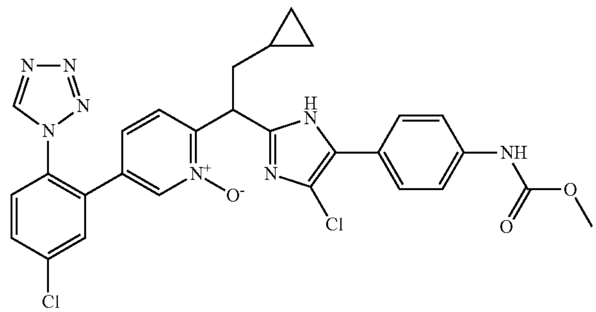 [SMILES: COC(=O)Nc1ccc(-c2[nH]c(C(CC3CC3)c3ccc(-c4cc(Cl)ccc4-n4cnnn4)c[n+]3[O-])nc2Cl)cc1] | OD column, slow eluting isomer | 591 | 0.50 | 24 |
| 80 | 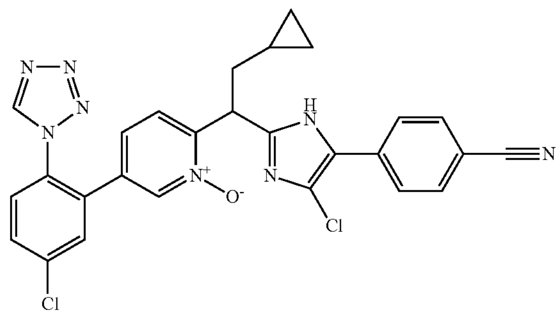 [SMILES: N#Cc1ccc(-c2[nH]c(C(CC3CC3)c3ccc(-c4cc(Cl)ccc4-n4cnnn4)c[n+]3[O-])nc2Cl)cc1] | racemic | 543 | | |

Examples 81 and 82

Step 1. (5-Bromopyridin-2-yl)(4-chloropyridin-2-yl)methanol (81-A)

n-BuLi (3.7 ml, 5.9 mmol) was dropped into a solution of 2-bromo-4-chloropyridine (1.14 g, 5.94 mmol) in toluene (60 ml) at −78° C., followed by stirring for 15 min. To it was added a solution of 5-bromopicolinaldehyde (0.88 g, 4.7 mmol) in toluene (15 ml) and it was stirred for 2 h while the temperature was slowly warmed up to 0° C. Then, the reaction mixture was quenched with 2M NH$_4$Cl, diluted with water and extracted with EtOAc. The organic phase was dried over MgSO$_4$, filtered and concentrated. The residue was taken up in ethanol (20 ml), followed by adding sodium borohydride (0.18 g, 4.75 mmol) and stirring for 1 h. The mixture was diluted with EtOAc and washed with water. The organic phase was dried over MgSO$_4$, filtered, concentrated and purified by flash chromatography on a silica-gel column with 0-50% EtOAc/CH$_2$Cl$_2$ to give the product 81-A. MS (ESI) m/z 300.98 (M+H).

Step 2. (5-Bromopyridin-2-yl)(4-chloropyridin-2-yl)methanone (81-B)

Manganese dioxide (1.22 g, 14.02 mmol) was added to a solution of (5-bromopyridin-2-yl)(4-chloropyridin-2-yl)methanol (0.42 g, 1.40 mmol) in CH$_2$Cl$_2$ (10 ml) at RT, followed by stirring at 50° C. for 1 h. The hot mixture was filtered and washed with hot EtOAc/EtOH (1:1, 10 ml). The filtrate was concentrated and purified by flash chromatography on a silica-gel column with 0-50% EtOAc/hexane to give the product 81-B. MS (ESI) m/z 298.53 (M+H).

Step 3. 2-(1-(5-Bromopyridin-2-yl)-2-phenylvinyl)-4-chloropyridine (81-C)

Lithium bis(trimethylsilyl)amide (1M, 1.70 ml, 1.70 mmol) was dropped to a solution of benzylchlorotriphenylphosphorane (0.66 g, 1.70 mmol) in THF (10 ml) at 0° C., followed by stirring at RT for 15 min. To it was added a solution of (5-bromopyridin-2-yl)(4-chloropyridin-2-yl)methanone (0.42 g, 1.42 mmol) in THF (5 ml), stirred at RT for 60 min. The mixture was quenched with 1.0 M NH$_4$Cl aq. (20 ml) and extracted with ethyl acetate. The organic phase was dried over MgSO$_4$, filtered and purified by flash chromatography on a silica-gel column with 0-40% EtOAc/hexane to give the product (81-C). MS (ESI) m/z 372.98 (M+H).

Step 4. 4-Chloro-2-(6-(1-(4-chloropyridin-2-yl)-2-phenylvinyl)pyridin-3-yl)aniline (81-D)

A vial was charged with (E)-2-(1-(5-bromopyridin-2-yl)-2-phenylvinyl)-4-chloropyridine (0.37 g, 1.00 mmol) 4-chloro-2-(4,4,5,5-tetramethyl-1,3,2-dioxaborolan-2-yl)aniline (0.25 g, 1.00 mmol), Tetrakis (0.23 g, 0.20 mmol) and sodium carbonate (0.26 g, 2.50 mmol) and the air was exchanged with N$_2$. Then, 1,4-dioxane (5 ml) and water (1 ml) were added, followed by stirring at 100° C. for 3 h. The mixture was diluted with EtOAc and washed with water. The organic phase was dried over MgSO$_4$, filtered, concentrated and purified by a flash chromatography on a silica-gel column with 0-65% EtOAc/CH$_2$Cl$_2$ to give the product (81-D). MS (ESI) m/z 418.14 (M+H).

Step 5. Methyl (4-(2-(1-(5-(2-amino-5-chlorophenyl)pyridin-2-yl)-2-phenylvinyl)pyridin-4-yl)phenyl)carbamate (81-E)

A vial was charged with 4-chloro-2-(6-(1-(4-chloropyridin-2-yl)-2-phenylvinyl)pyridin-3-yl)aniline (0.22 g, 0.53 mmol), (4-((methoxycarbonyl)amino) phenyl) boronic acid (0.13 g, 0.66 mmol), PdCl$_2$(dppf) (0.08 g, 0.11 mmol) and sodium carbonate (0.17 g, 1.58 mmol). It was then capped and air was removed by vacuum and back-filled with N$_2$. Then, 1, 4-dioxane (4 ml) and H$_2$O (1 ml) were added, followed by stirring at 100° C. for 90 min. The mixture was diluted with EtOAc and washed with water. The organic phase was dried over MgSO$_4$, filtered, concentrated and purified by a flash chromatography on a silica-gel column with 0-60% EtOAc/CH$_2$Cl$_2$ to give the product (81-E). MS (ESI) m/z 533.34 (M+H).

Step 6. Methyl (4-(2-(1-(5-(5-chloro-2-(1H-tetrazol-1-yl)phenyl)pyridin-2-yl)-2-phenylvinyl) pyridin-4-yl)phenyl)carbamate (81-F)

A mixture of methyl (4-(2-(1-(5-(2-amino-5-chlorophenyl)pyridin-2-yl)-2-phenylvinyl)pyridin-4-yl)phenyl)carbamate (0.18 g, 0.34 mmol), sodium azide (0.07 g, 1.01 mmol) and trimethyl orthoformate (0.19 ml, 1.69 mmol) in acetic acid (2 ml) was stirred at 80° C. for 2 h. The solvent was removed and the residue was purified by a flash chromatograpy on a silica-gel with 0-60% EtOAc/CH$_2$Cl$_2$ to give the product 81-F. MS (ESI) m/z 586.35 (M+H).

Step 7. (4-(2-(1-(5-(5-Chloro-2-(1H-tetrazol-1-yl)phenyl)pyridin-2-yl)-2-phenylethyl)pyridin-4-yl)phenyl)carbamate (81-G)

A flask was charged with a mixture of methyl (4-(2-(1-(5-(5-chloro-2-(1H-tetrazol-1-yl)phenyl)pyridin-2-yl)-2-phenylvinyl)pyridin-4-yl)phenyl)carbamate (0.14 g, 0.24 mmol), Pd—C (10%) (0.03 g) and solvents of EtOAc (2.00 ml) and EtOH (2.00 ml) and the air was exchanged with N$_2$, followed by stirring under H$_2$ from a balloon at RT for 2 h. The catalyst was filtered through celite and the filtrate was concentrated and purified by flash chromatography on a silica-gel with 0-60% EtOAc/CH$_2$Cl$_2$ to give the product 81-G. MS (ESI) m/z 588.36 (M+H).

Step 8. 5-(5-Chloro-2-(1H-tetrazol-1-yl)phenyl)-2-(1-(4-(4-((methoxycarbonyl)amino)phenyl) pyridin-2-yl)-2-phenylethyl)pyridine 1-oxide (Examples 81 and 82)

mCPBA (0.035 g, 0.204 mmol) was added to a solution of methyl (4-(2-(1-(5-(5-chloro-2-(1H-tetrazol-1-yl)phenyl)pyridin-2-yl)-2-phenylethyl)pyridin-4-yl)phenyl)carbamate (81-G) (0.10 g, 0.17 mmol) in CH$_2$Cl$_2$ (1.5 ml), followed by stirring at RT over the weekend. The solvent was removed and purified by preparative HPLC Reverse phase (C-18), eluting with acetonitrile/water+0.1% TFA, to give the racemic product, which was resolved by SFC with chiral OJ-H column to give 5-(5-Chloro-2-(1H-tetrazol-1-yl)phenyl)-2-(1-(4-(4-((methoxycarbonyl)amino)phenyl)pyridin-2-yl)-2-phenylethyl)pyridine 1-oxide, fast eluting enantiomer (Example 81), MS (ESI) m/z 604.14, and 5-(5-Chloro-2-(1H-tetrazol-1-yl)phenyl)-2-(1-(4-(4-((methoxycarbonyl)amino)phenyl)pyridin-2-yl)-2-phenylethyl)pyridine 1-oxide, slow eluting enantiomer (Example 82), MS (ESI) m/z 604.14 (M+H).
$^1$H NMR (500 MHz, (CD$_3$)$_2$SO δ: 3.24 (2H, dd), 3.65 (3H, s), 5.15 (1H, t), 7.08 (4H, m), 7.20 (3H, m), 7.41 (1H, d), 7.61 (3H, m), 7.67 (2H, d), 7.78 (2H, d), 7.90 (1H, s), 8.20 (1H, d), 8.78 (1H, s), 9.88 (1H, s).

Example 83

5-(5-chloro-2-(1H-tetrazol-1-yl)phenyl)-2-(1-(5-(4-((methoxycarbonyl)amino)phenyl)-1,3,4-oxadiazol-2-yl)-2-phenylethyl)pyridine 1-oxide (Example 83)

Step 1. methyl (4-(2-(2-(5-bromopyridin-2-yl)-3-phenylpropanoyl)hydrazinecarbonyl)phenyl) carbamate (83-B)

2-(5-bromopyridin-2-yl)-3-phenylpropanoic acid (620 mg, 2.0 mmol) was mixed with methyl (4-(hydrazinecarbonyl)phenyl)carbamate (424 mg, 2.0 mmol), HATU (770 mg, 2.0 mmol) and N-methylmorpholine (0.45 mL, 4 mmol) in DMF (13 mL), and stirred at room temperature for 16 hours. The reaction mixture was diluted with ethyl acetate and washed with diluted sodium bicarbonate, and brine. After it was dried over anhydrous sodium sulfate, and filtered, the solution was concentrated to give 83-B. The crude product was used in the next step without further purification. MS (ESI) m/z 499.4 (M+H).

Step 2. Methyl (4-(5-(1-(5-bromopyridin-2-yl)-2-phenylethyl)-1,3,4-oxadiazol-2-yl)phenyl) carbamate (83-C)

Methyl (4-(2-(2-(5-bromopyridin-2-yl)-3-phenylpropanoyl)hydrazinecarbonyl)phenyl)carbamate (600 mg, 1.2 mmol) was mixed with Burgess reagent (345 mg, 1.5 mmol) in THF (12 mL) in a microwave reaction vial. The vial was capped, and heated to 140° C. for 10 min. The reaction mixture was diluted with ethyl acetate and washed with water and brine. After it was dried over anhydrous sodium sulfate, and filtered, the solution was concentrated, and the crude was purified by column chromatography on a 40 g ISCO column, eluting with gradient Hex/EtOAc to give 83-C. MS (ESI) m/z 481.3 (M+H).

Step 3. methyl (4-(5-(1-(5-(2-amino-5-chlorophenyl)pyridin-2-yl)-2-phenylethyl)-1,3,4-oxadiazol-2-yl)phenyl) carbamate (83-D)

Methyl (4-(5-(1-(5-bromopyridin-2-yl)-2-phenylethyl)-1, 3,4-oxadiazol-2-yl)phenyl)carbamate (83-C, 172 mg, 0.36 mmol), was mixed with 4-chloro-2-(4,4,5,5-tetramethyl-1, 3,2-dioxaborolan-2-yl)aniline (109 mg, 0.43 mmol), PdCl2 (dppf) (52 mg, 0.07 mmol), and cesium fluoride (164 mg, 1.1 mmol) in a microwave reaction vial. The vial was degassed, and 1,4-dioxane (3.6 mL) was introduced. The mixture was heated to 120° C. for 10 min. The crude was purified by flask chromatography on ISCO 12 g prepacked column, eluting with gradient 0~40% EtOAc/DCM to give 83-D. MS (ESI) m/z 526.1 (M+H).

Step 4. methyl (4-(5-(1-(5-(5-chloro-2-(1H-tetrazol-1-yl)phenyl)pyridin-2-yl)-2-phenylethyl)-1,3,4-oxadiazol-2-yl)phenyl)carbamate (83-E)

Methyl (4-(5-(1-(5-(2-amino-5-chlorophenyl)pyridin-2-yl)-2-phenylethyl)-1,3,4-oxadiazol-2-yl)phenyl) carbamate (83-D, 33 mg, 0.063 mmol) was mixed with sodium azide (12 mg, 0.19 mmol) and trimethyl orthoformate (20 mg, 0.19 mmol) in acetic acid (0.63 mL). The resulting mixture was stirred at room temperature overnight. The mixture was concentrated, the crude was dissolved in ethyl acetate, and washed with sodium bicarbonate and brine. The organic layer was separated, dried and concentrated. The crude was purified by flask chromatography on ISCO 12 g prepacked column, eluting with gradient 0~100% EtOAc/hexane to give 83-E. MS (ESI) m/z 579.4 (M+H).

Step 5. 5-(5-chloro-2-(1H-tetrazol-1-yl)phenyl)-2-(1-(5-(4-((methoxycarbonyl)amino)phenyl)-1,3,4-oxadiazol-2-yl)-2-phenylethyl)pyridine 1-oxide (Example 83)

Methyl (4-(5-(1-(5-(5-chloro-2-(1H-tetrazol-1-yl)phenyl)pyridin-2-yl)-2-phenylethyl)-1,3,4-oxadiazol-2-yl)phenyl)carbamate (83-E, 28 mg, 0.046 mmol) was mixed with methyltrioxorhenium (6 mg, 0.024 mmol) and hydrogen peroxide (30%, 0.05 mL, 0.48 mmol) in methanol (0.48 mL). The resulting mixture was stirred at room temperature for 1 hour. The excess hydrogen peroxide was quenched with 10% NaHSO$_3$. The crude was purified by reverse phase prep HPLC to give Example 83. MS (ESI) m/z 595 (M+H).

Factor XIa Assay

The effectiveness of a compound of the present invention as an inhibitor of Coagulation Factor XIa can be determined using a relevant purified serine protease, and an appropriate synthetic substrate. The rate of hydrolysis of the chromogenic or fluorogenic substrate by the relevant serine protease was measured both in the absence and presence of compounds of the present invention. Assays were conducted at room temperature or at 37° C. Hydrolysis of the substrate resulted in release of amino trifluoromethylcoumarin (AFC), which was monitored spectrofluorometrically by measuring the increase in emission at 510 nm with excitation at 405 nm. A decrease in the rate of fluorescence change in the presence of inhibitor is indicative of enzyme inhibition. Such methods are known to one skilled in the art. The results of this assay are expressed as the inhibitory constant, $K_i$.

| Ex | Structure | Chiral Separation | Exact Mass [M + H]+ | F11a IC50 nM | PK IC50 nM |
|---|---|---|---|---|---|
| 81 | 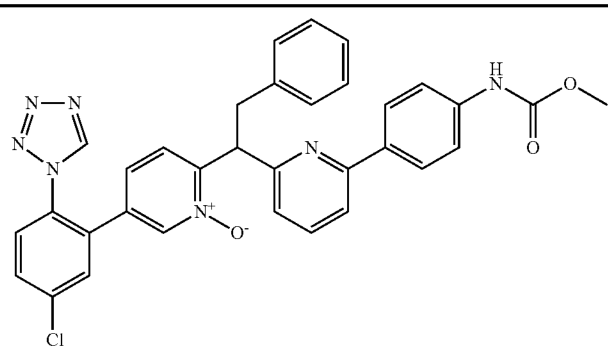 | OJ-H column, Fast eluting isomer | 604 | 1270 | |
| 82 | 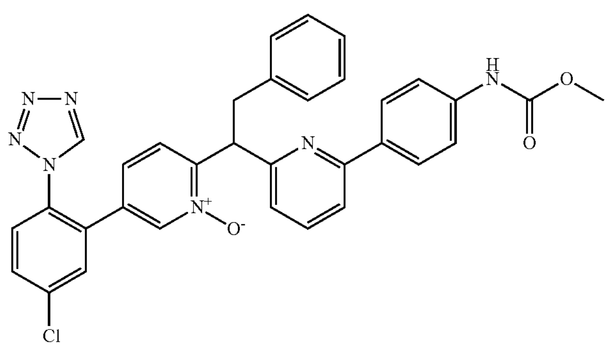 [SMILES: COC(=O)Nc1ccc(-c2cccc(C(Cc3ccccc3)c3ccc(-c4cc(Cl)ccc4-n4cnnn4)c[n+]3[O-])n2)cc1] | OJ-H column, Fast eluting isomer | 604 | 125 | |
| 83 | 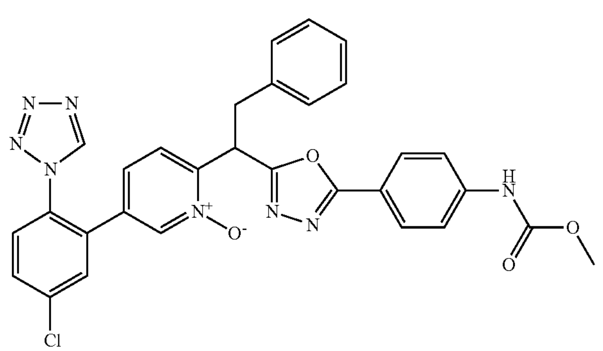 [SMILES: COC(=O)Nc1ccc(-c2nnc(C(Cc3ccccc3)c3ccc(-c4cc(Cl)ccc4-n4cnnn4)c[n+]3[O-])o2)cc1] | racemic | 595 | 1.2 | 68 |

Factor XIa determinations were made in 50 mM HEPES buffer at pH 7.4 containing 150 mM NaCl, 5 mM CaCl$_2$, and 0.1% PEG 8000 (polyethylene glycol; JT Baker or Fisher Scientific). Determinations were made using purified human Factor XIa at a final concentration of 40 pM (Sekisui Diagnostics) and he synthetic substrate, Z-Gly-Pro-Arg-AFC, TFA salt (Sigma #C0980) at a concentration of 100 μM.

Activity assays were performed by diluting a stock solution of substrate at least tenfold to a final concentration ≤0.1 $K_m$ into a solution containing enzyme or enzyme equilibrated with inhibitor. Times required to achieve equilibration between enzyme and inhibitor were determined in control experiments. Initial velocities of product formation in the absence ($V_O$) or presence of inhibitor ($V_i$) were measured. Assuming competitive inhibition, and that unity is negligible compared $K_m/[S]$, [I]/e, and [I]/e (where [S], [I], and e respectively represent the total concentrations, of substrate, inhibitor and enzyme), the equilibrium constant ($K_i$) for dissociation of the inhibitor from the enzyme can be obtained from the dependence of $V_O/V_i$ on [I] shown in the following equation.

$$V_O/V_i = 1 + [I]/K_i$$

The activities shown by this assay indicate that the compounds of the invention may be therapeutically useful for treating or preventing various cardiovascular and/or cerebrovascular thromboembolic conditions in patients suffering from unstable angina, acute coronary syndrome, refractory angina, myocardial infarction, transient ischemic attacks, atrial fibrillation, stroke such as thrombotic stroke or embolic stroke, venous thrombosis, coronary and cerebral arterial thrombosis, cerebral and pulmonary embolism, atherosclerosis, deep vein thrombosis, disseminated intravascular coagulation, and reocclusion or restenosis of recanalized vessels.

Kallikrein Assay

The effectiveness of a compound of the present invention as an inhibitor of Kallikrein can be determined using a relevant purified serine protease, and an appropriate synthetic substrate. The rate of hydrolysis of the chromogenic or fluorogenic substrate by the relevant serine protease was measured both in the absence and presence of compounds of the present invention. Assays were conducted at room temperature or at 37° C. Hydrolysis of the substrate resulted in release of amino trifluoromethylcoumarin (AFC), which was monitored spectrofluorometrically by measuring the increase in emission at 510 nm with excitation at 405 nm. A decrease in the rate of fluorescence change in the presence of inhibitor is indicative of enzyme inhibition. Such methods are known to one skilled in the art. The results of this assay are expressed as the inhibitory constant, $K_1$.

Kallikrein determinations were made in 50 mM HEPES buffer at pH 7.4 containing 150 mM NaCl, 5 mM CaCl$_2$, and 0.1% PEG 8000 (polyethylene glycol; Fisher Scientific). Determinations were made using purified Human plasma kallikrein at a final concentration of 0.5 nM (Enzyme Research Laboratories) and the synthetic substrate, Acetyl-K—P—R-AFC (Sigma # C6608) at a concentration of 100 mM.

Activity assays were performed by diluting a stock solution of substrate at least tenfold to a final concentration <0.2 $K_m$ into a solution containing enzyme or enzyme equilibrated with inhibitor. Times required to achieve equilibration between enzyme and inhibitor were determined in control experiments. The reactions were performed under linear progress curve conditions and fluorescence increase measured at 405 Ex/510 Em nm. Values were converted to percent inhibition of the control reaction (after subtracting 100% Inhibition value). IC$_{50}$ was determined by inflection point from a four parameter logistic curve fit. Ki was calculated using the Cheng Prusoff equation, Ki=IC$_{50}$/(1+([S]/Km)).

The activities shown by this assay indicate that the compounds of the invention may be therapeutically useful for treating or preventing various cardiovascular and/or cerebrovascular thromboembolic conditions in patients suffering from unstable angina, acute coronary syndrome, refractory angina, myocardial infarction, transient ischemic attacks, atrial fibrillation, stroke such as thrombotic stroke or embolic stroke, venous thrombosis, coronary and cerebral arterial thrombosis, cerebral and pulmonary embolism, atherosclerosis, deep vein thrombosis, disseminated intravascular coagulation, and reocclusion or restenosis of recanalized vessels.

The invention claimed is:
1. A compound of the formula:

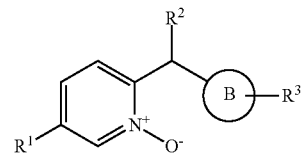

wherein

is a 5 or 6 membered heteroaryl ring, wherein said heteroaryl ring is optionally substituted with one to three substituents independently selected from the group consisting of nitro, cyano, oxo, R$^a$, (C=O)R$^4$, (C=O)OR$^4$, NR$^4$R$^5$, NH(C=O)R$^4$, NH(C=O)OR$^4$, SO$_2$R$^4$, SO$_2$NR$^4$R$^5$, NR$^4$SO$_2$R$^5$ and PO$_3$R$^4$;

R$^1$ is aryl, heteroaryl, C$_{3-6}$ cycloalkyl or heterocyclyl, wherein said aryl, heteroaryl, cycloalkyl and heterocyclyl groups are optionally substituted with one to three substituents independently selected from the group consisting of halo, nitro, cyano, oxo, R$^4$, OR$^4$, (C=O)R$^4$, (C=O)OR$^4$, NR$^4$R$^5$, NH(C=O)R$^4$, NH(C=O)OR$^4$, C$_{3-6}$ cycloalkyl and heteroaryl which is optionally substituted with R$^4$;

R$^2$ is hydrogen or CH(R$^{2a}$)(R$^{2b}$);

R$^{2a}$ is hydrogen, C$_{1-6}$ alkyl, aryl, heteroaryl, C$_{3-6}$ cycloalkyl, heterocyclyl or (C=O)NR$^4$R$^5$, wherein said alkyl group is optionally substituted with one to three substituents independently selected from the group consisting of halo, hydroxy and cyano, and wherein said aryl, heteroaryl, cycloalkyl and heterocyclyl groups are optionally substituted with one to three substituents independently selected from the group consisting of halo, nitro, cyano, oxo, R$^4$ and OR$^4$;

R$^{2b}$ is hydrogen or C$_{1-6}$ alkyl, which is optionally substituted with one to three substituents independently selected from the group consisting of halo, hydroxy and cyano;

R³ is halo, cyano, (C=O)OR⁴ or R⁶;
R⁴ is hydrogen or C₁₋₆ alkyl, which is optionally substituted with one to three groups independently selected from the group consisting of halo and hydroxy;
R⁵ is hydrogen or C₁₋₆ alkyl, which is optionally substituted with one to three groups independently selected from the group consisting of halo and hydroxy;
R⁶ is aryl, heteroaryl, C₃₋₁₀ cycloalkyl or heterocyclyl, wherein said aryl, heteroaryl, cycloalkyl and heterocyclyl groups are optionally substituted with one to three substituents independently selected from the group consisting of halo, nitro, cyano, oxo, R⁴, OR⁴, (C=O)R⁴, (C=O)OR⁴, (C=O)NR⁴R⁵, NR⁴R⁵, NH(C=O)R⁴, NH(C=O)OR⁴, SO₂R⁴, SO₂NR⁴R⁵, NR⁴SO₂R⁵ and PO₃R⁴;
Rᵃ is hydrogen, halo, R⁴ or OR⁴;
or a pharmaceutically acceptable salt thereof.

2. The compound of claim 1 of the formula:

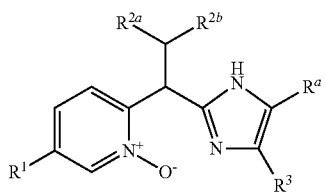

wherein R¹ is aryl, heteroaryl, C₃₋₆ cycloalkyl or heterocyclyl, wherein said aryl, heteroaryl, cycloalkyl and heterocyclyl groups are optionally substituted with one to three substituents independently selected from the group consisting of halo, nitro, cyano, oxo, R⁴, OR⁴, (C=O)R⁴, (C=O)OR⁴, NR⁴R⁵, NH(C=O)R⁴, NH(C=O)OR⁴, C₃₋₆ cycloalkyl and heteroaryl which is optionally substituted with R⁴;
R²ᵃ is hydrogen, C₁₋₆ alkyl, aryl, heteroaryl, C₃₋₆ cycloalkyl, heterocyclyl or (C=O)NR⁴R⁵, wherein said alkyl group is optionally substituted with one to three substituents independently selected from the group consisting of halo, hydroxy and cyano, and wherein said aryl, heteroaryl, cycloalkyl and heterocyclyl groups are optionally substituted with one to three substituents independently selected from the group consisting of halo, nitro, cyano, oxo, R⁴ and OR⁴;
R²ᵇ is hydrogen or C₁₋₆ alkyl, which is optionally substituted with one to three substituents independently selected from the group consisting of halo, hydroxy and cyano;
R³ is halo, cyano, (C=O)OR⁴ or R⁶;
R⁴ is hydrogen or C₁₋₆ alkyl, which is optionally substituted with one to three groups independently selected from the group consisting of halo and hydroxy;
R⁵ is hydrogen or C₁₋₆ alkyl, which is optionally substituted with one to three groups independently selected from the group consisting of halo and hydroxy;
R⁶ is aryl, heteroaryl, C₃₋₁₀ cycloalkyl or heterocyclyl, wherein said aryl, heteroaryl, cycloalkyl and heterocyclyl groups are optionally substituted with one to three substituents independently selected from the group consisting of halo, nitro, cyano, oxo, R⁴, OR⁴, (C=O)R⁴, (C=O)OR⁴, (C=O)NR⁴R⁵, NR⁴R⁵, NH(C=O)R⁴, NH(C=O)OR⁴, SO₂R⁴, SO₂NR⁴R⁵, NR⁴SO₂R⁵ and PO₃R⁴;
Rᵃ is hydrogen, halo, C₁₋₃ alkyl or O(C₁₋₃ alkyl);
or a pharmaceutically acceptable salt thereof.

3. The compound of claim 1 wherein R¹ is aryl, which optionally is substituted with one to three substituents independently selected from the group consisting of halo, cyano, R⁴, OR⁴ and heteroaryl which is optionally substituted with R⁴; or a pharmaceutically acceptable salt thereof.

4. The compound of claim 1 wherein R¹ is phenyl, which optionally is substituted with one to two substituents independently selected from the group consisting of halo and tetrazolyl; or a pharmaceutically acceptable salt thereof.

5. The compound of claim 1 wherein R²ᵃ is aryl, which optionally is substituted with one to three halo groups; or a pharmaceutically acceptable salt thereof.

6. The compound of claim 1 wherein R²ᵃ is phenyl, which optionally is substituted with halo; or a pharmaceutically acceptable salt thereof.

7. The compound of claim 1 wherein R²ᵇ is hydrogen; or a pharmaceutically acceptable salt thereof.

8. The compound of claim 1 wherein R²ᵃ is cyclopropyl; or a pharmaceutically acceptable salt thereof.

9. The compound of claim 1 wherein R³ is R⁶, which optionally is substituted with halo, (C=O)OR⁴ or NH(C=O)OR⁴, or a pharmaceutically acceptable salt thereof.

10. The compound of claim 1 selected from:

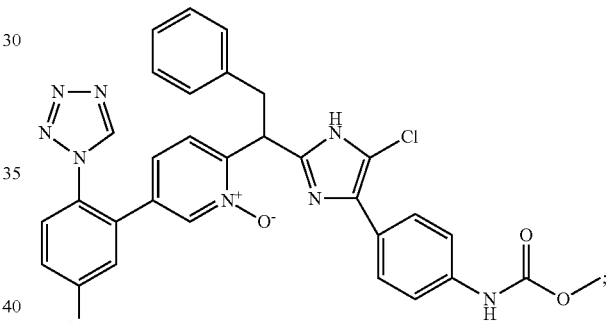

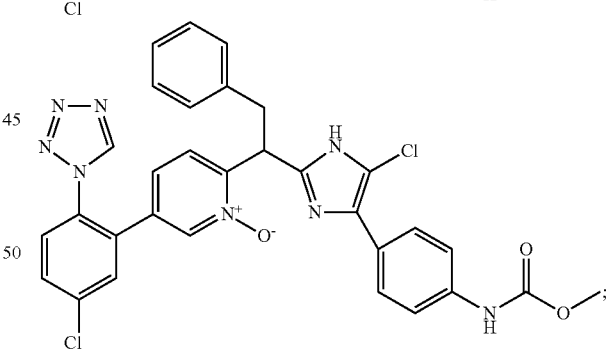

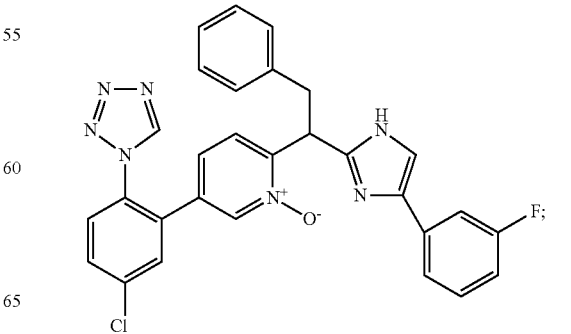

117
-continued
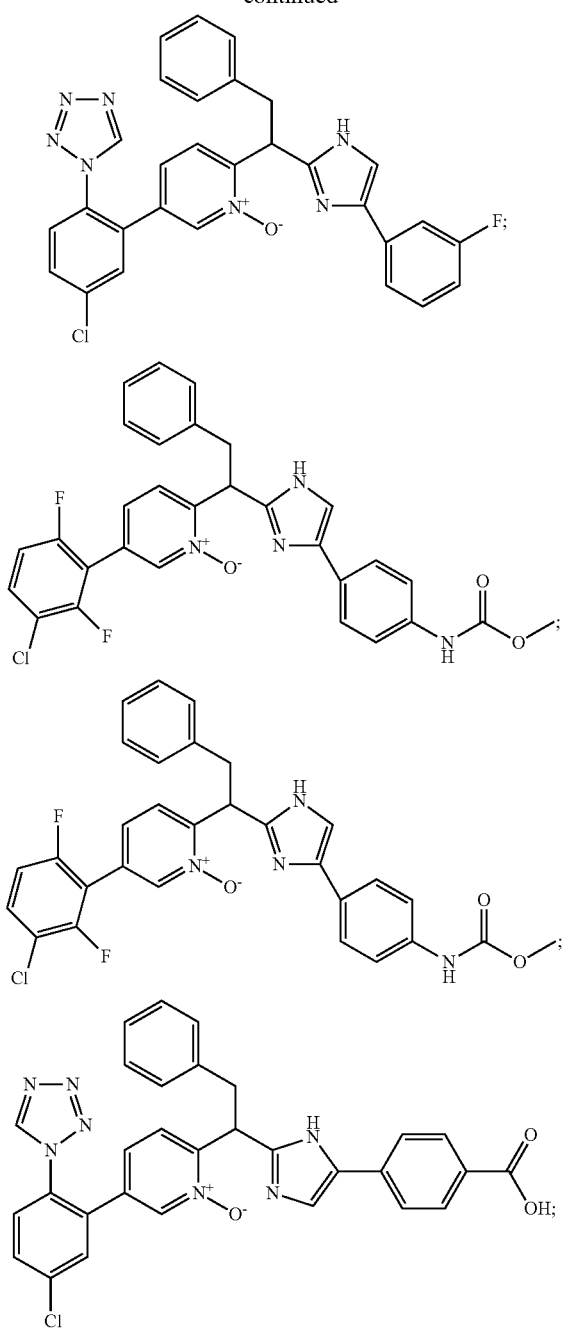
118
-continued
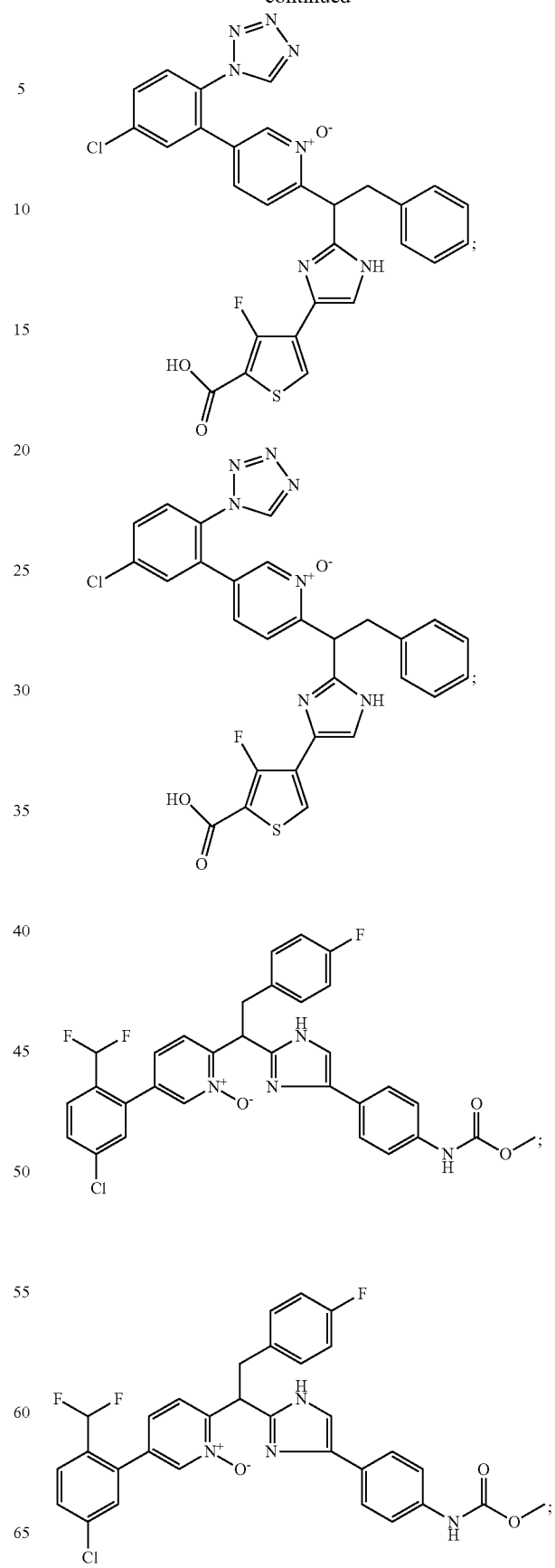

119
-continued
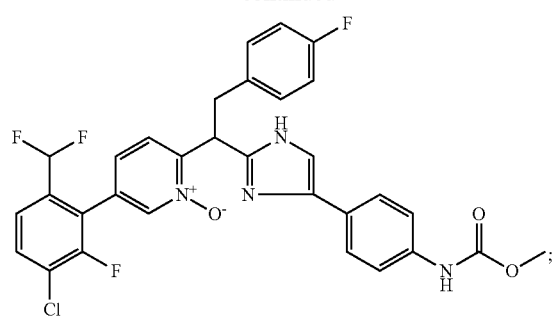
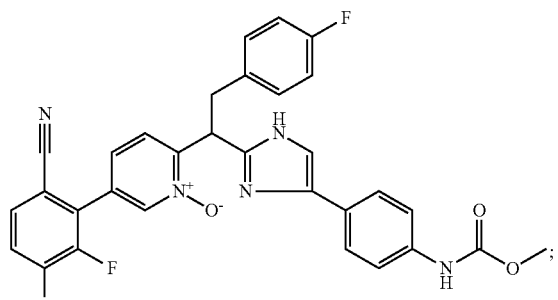
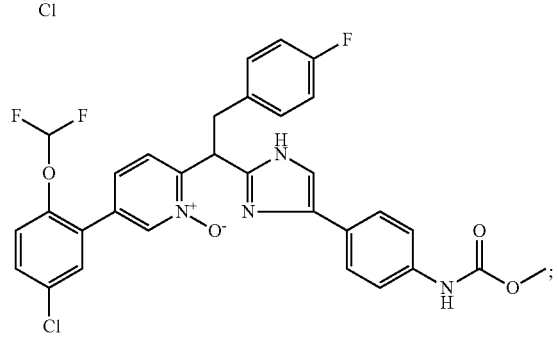
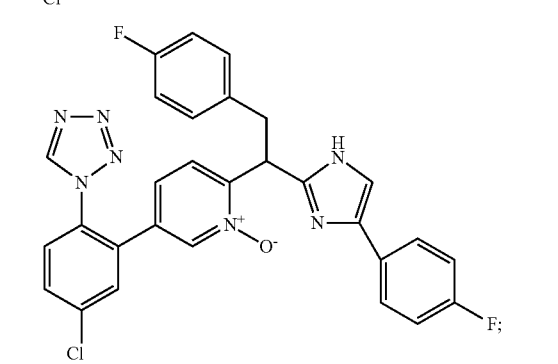
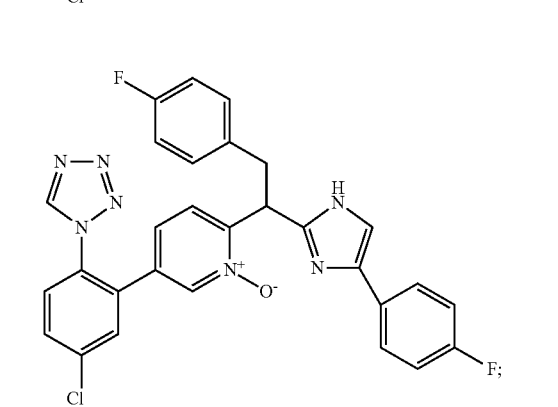
120
-continued
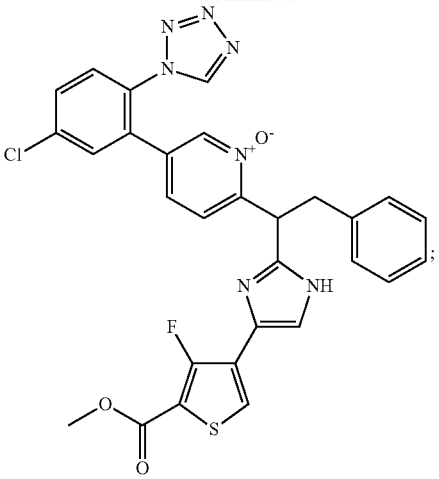
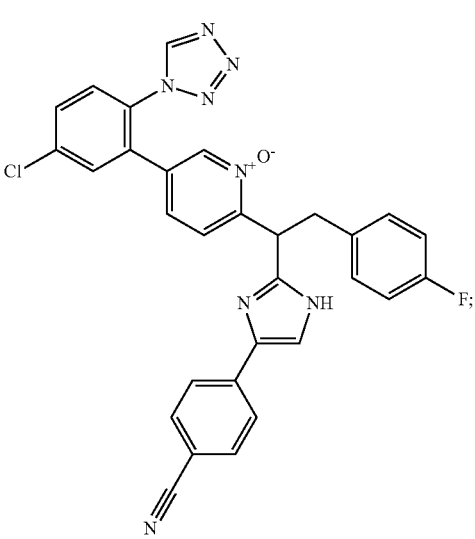
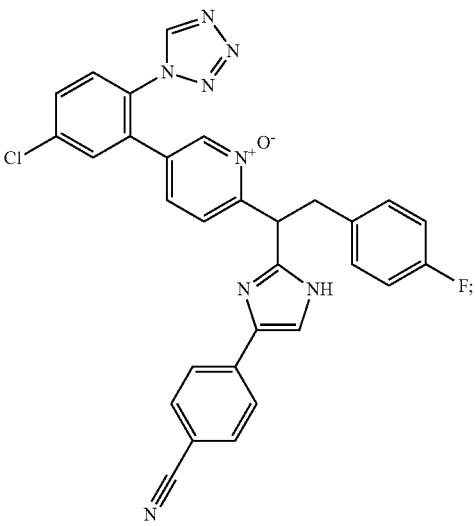

121
-continued
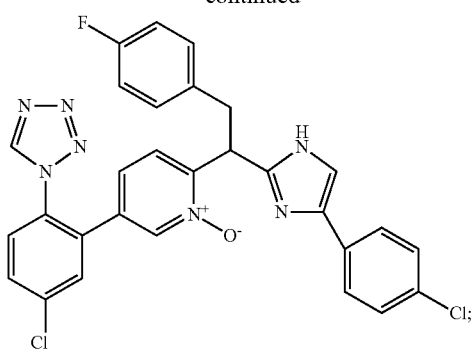
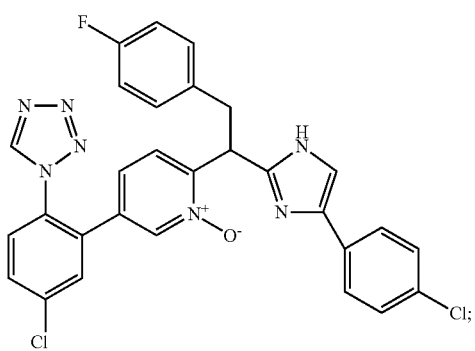
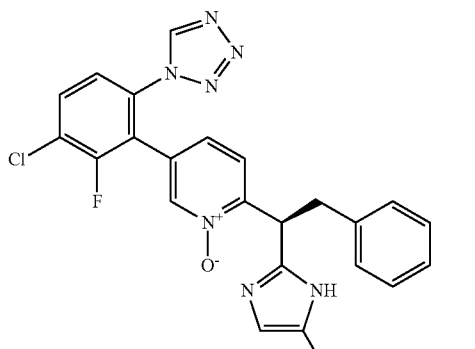
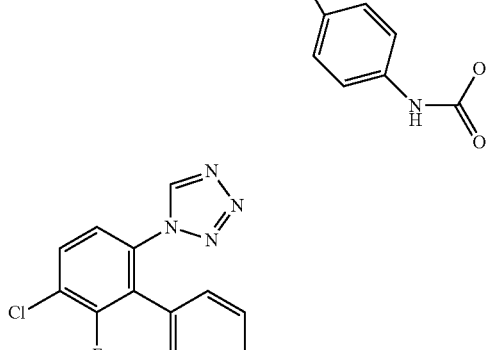
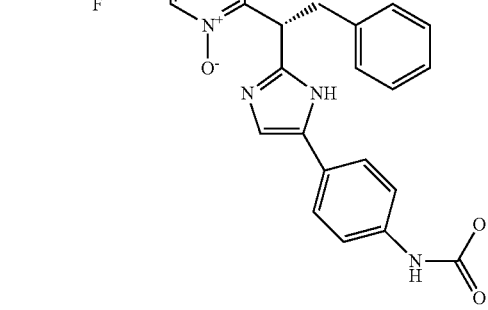
122
-continued
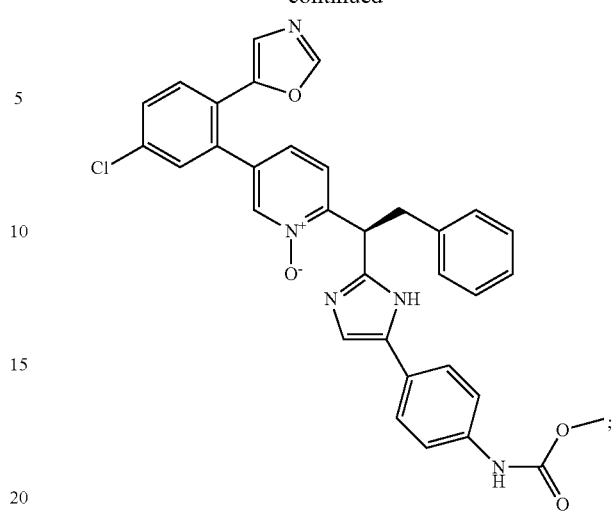
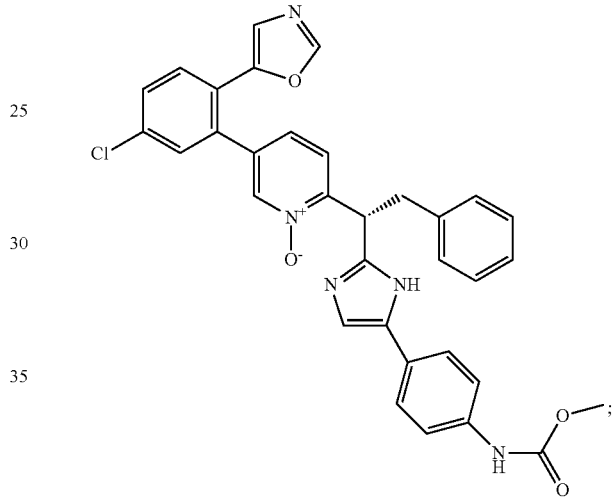
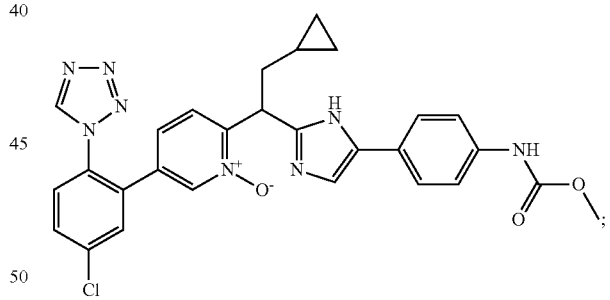
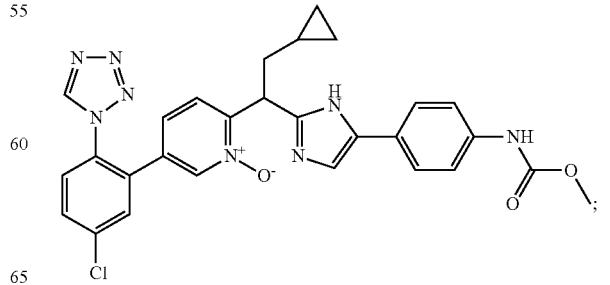

123
-continued
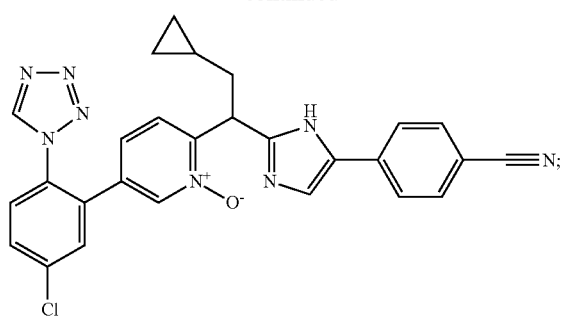
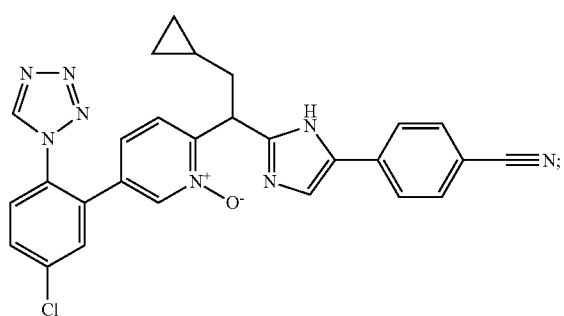
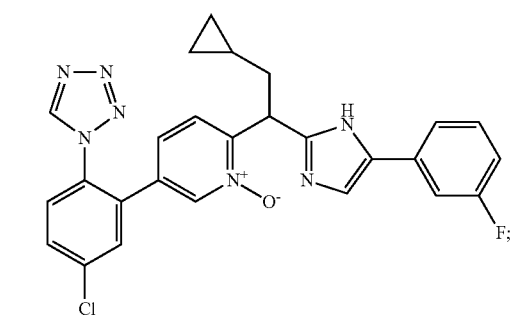
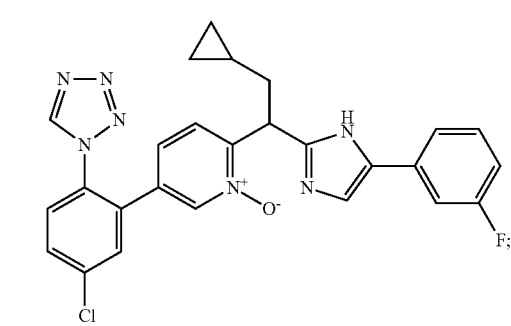
124
-continued
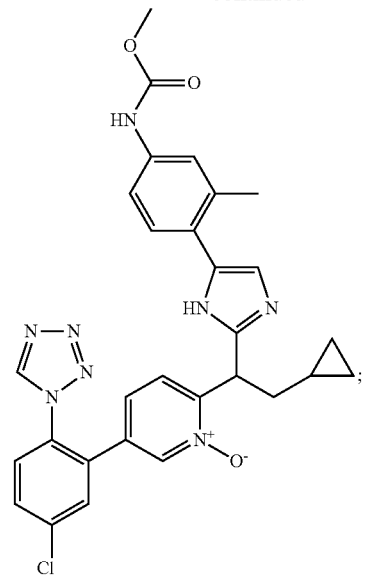
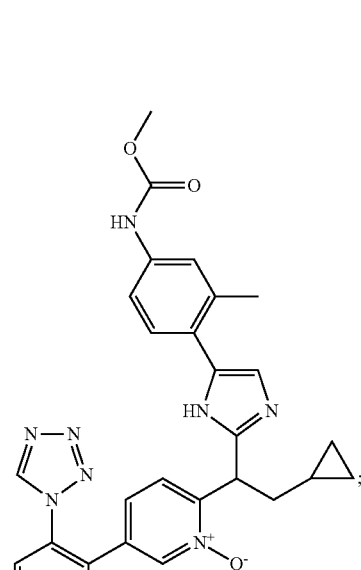
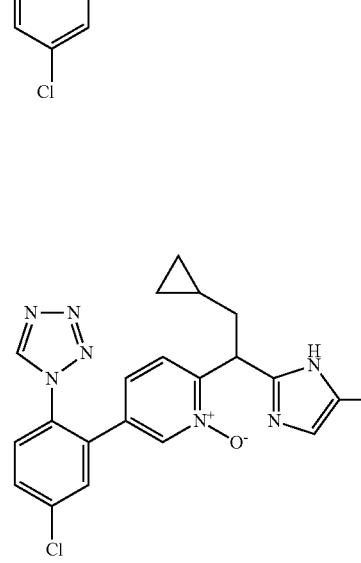

125
-continued
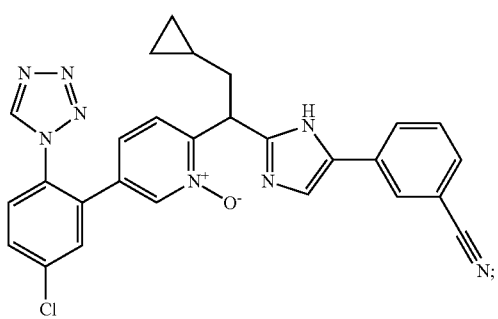
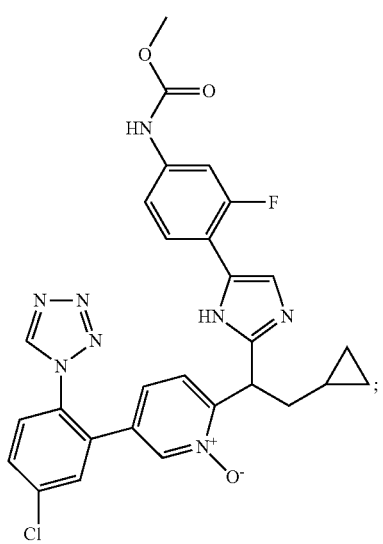
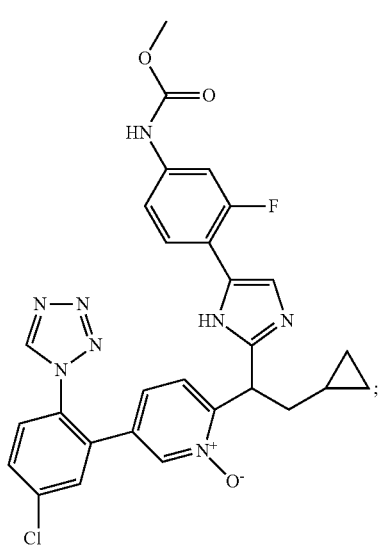
126
-continued
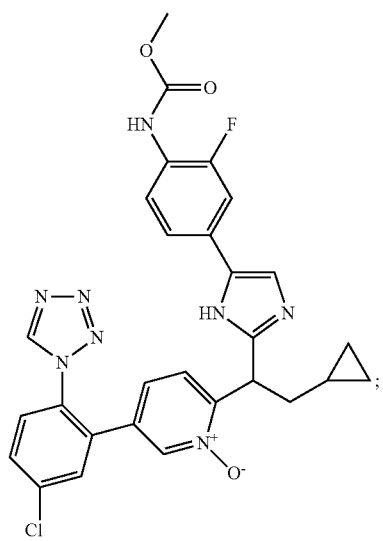
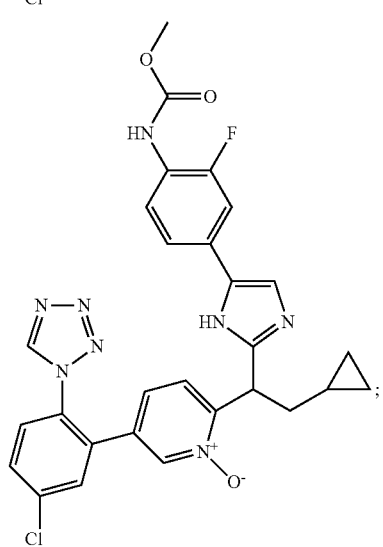
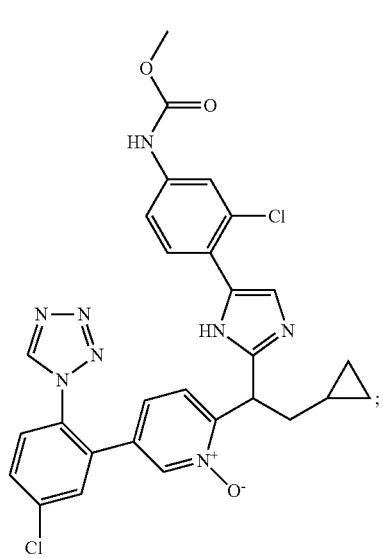

127
-continued
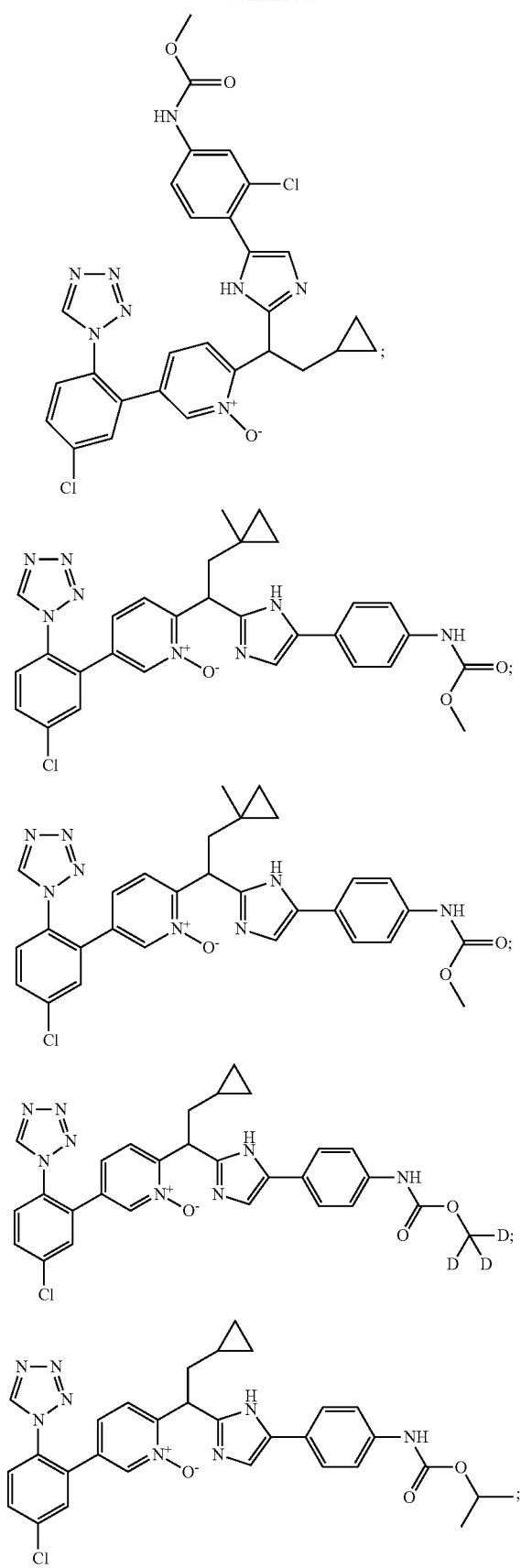
128
-continued
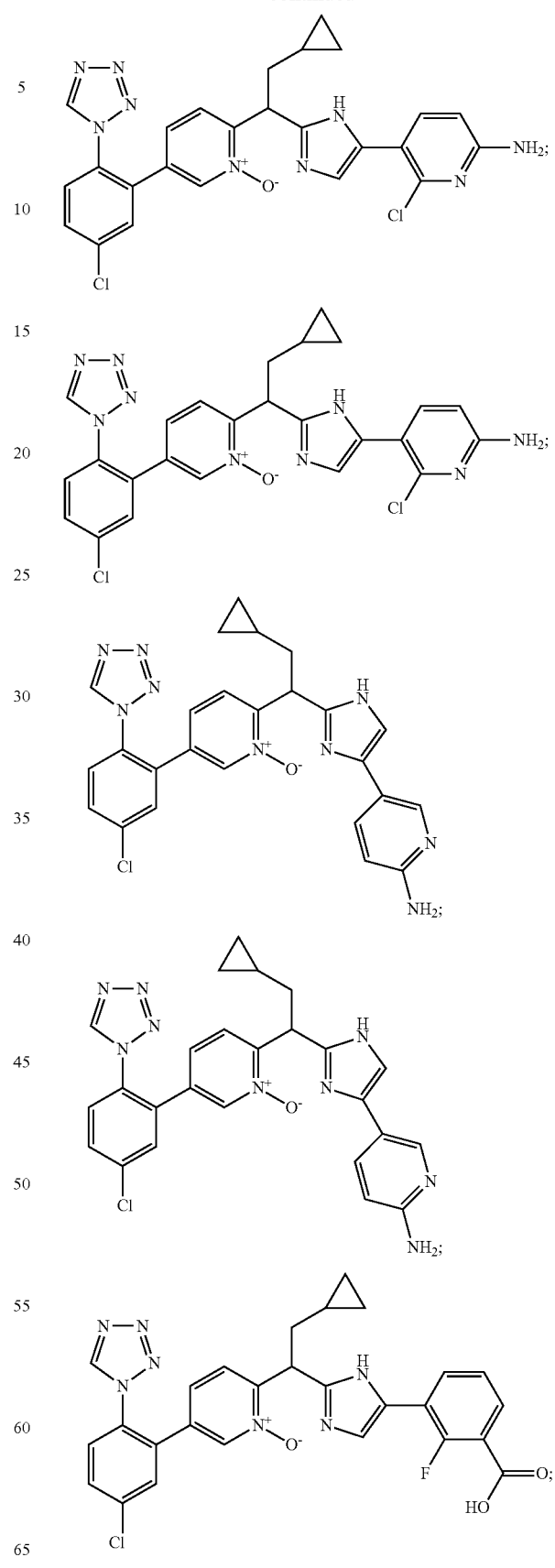

129
-continued
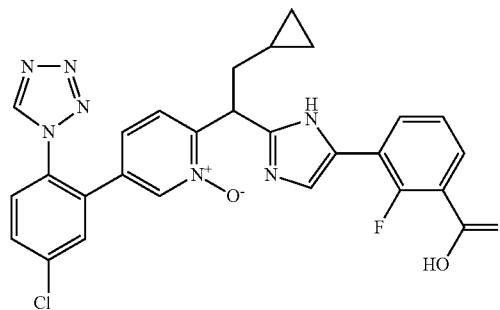
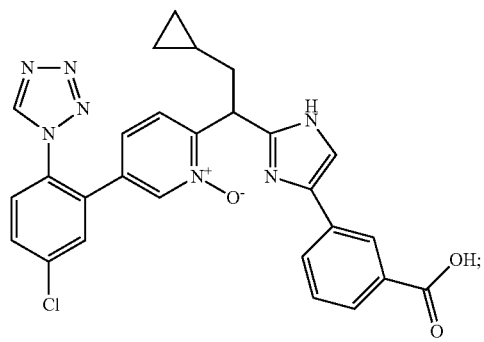
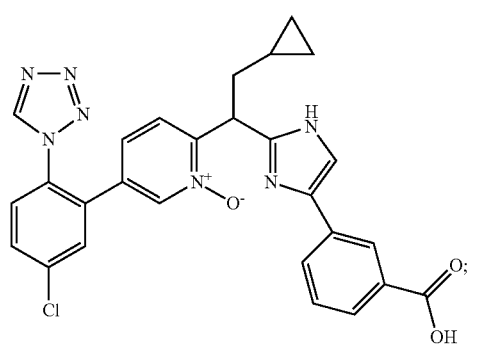
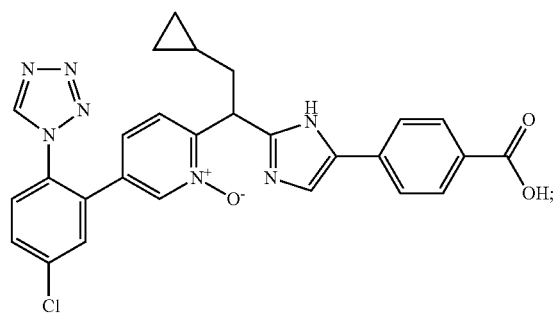
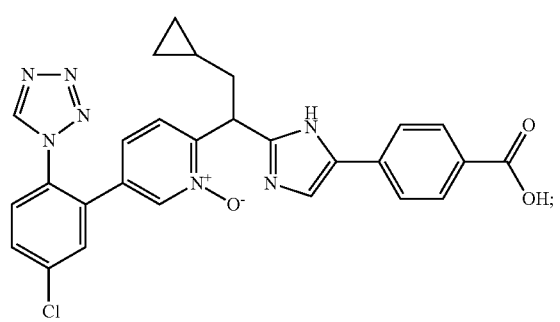
130
-continued
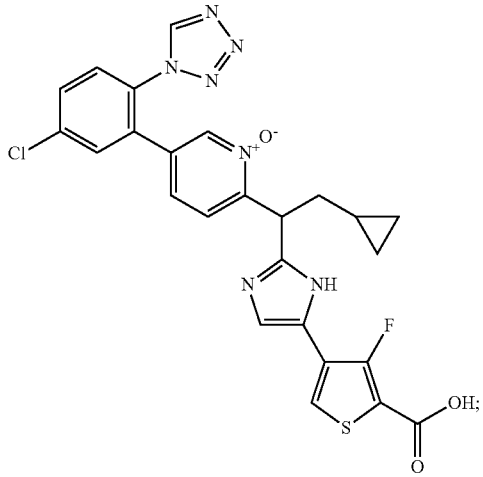
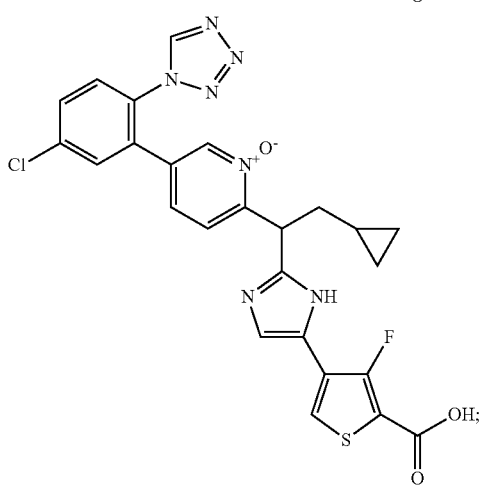
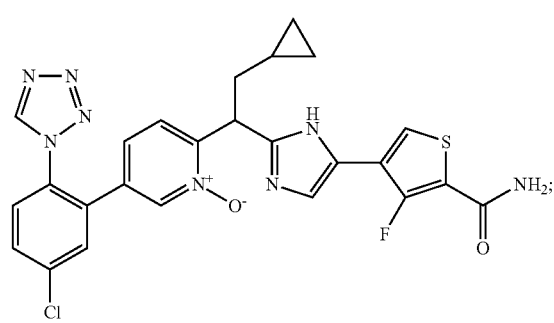

131
-continued
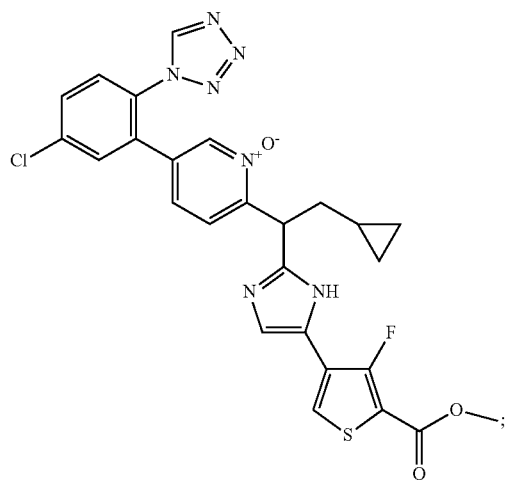
132
-continued
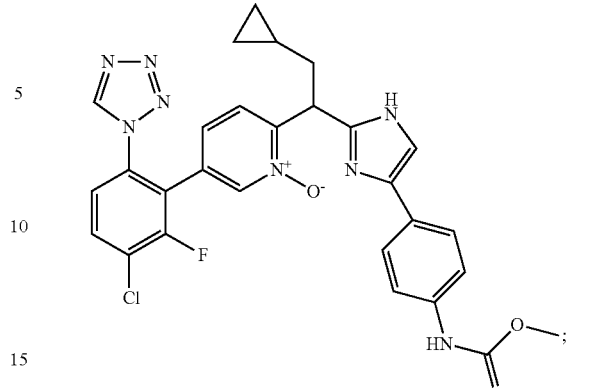
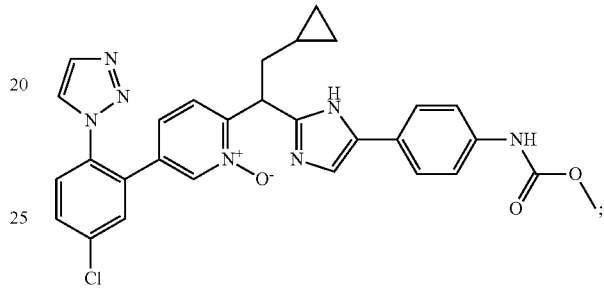
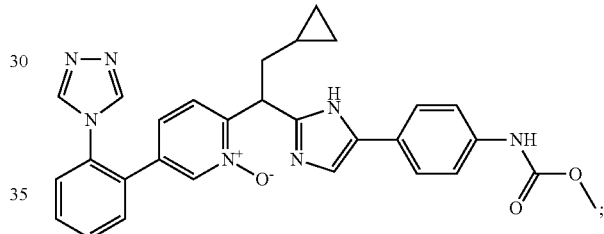
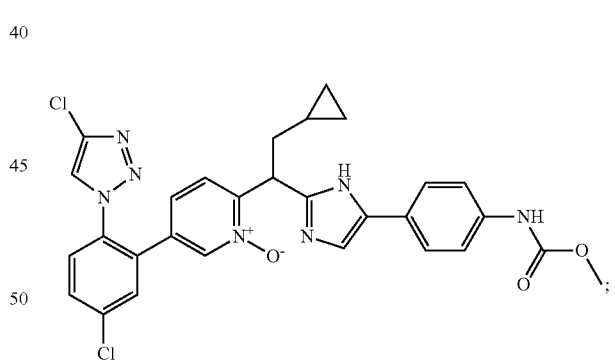
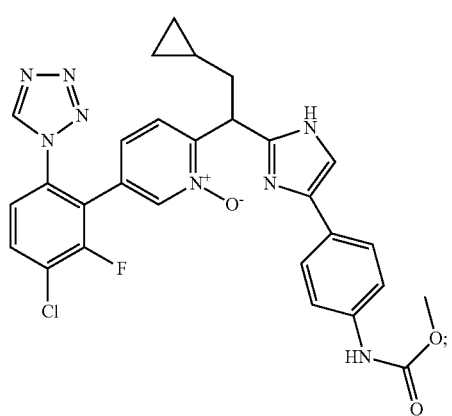

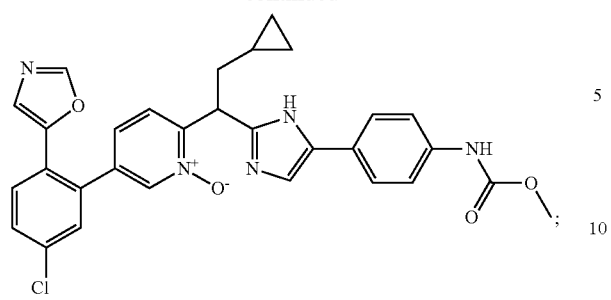
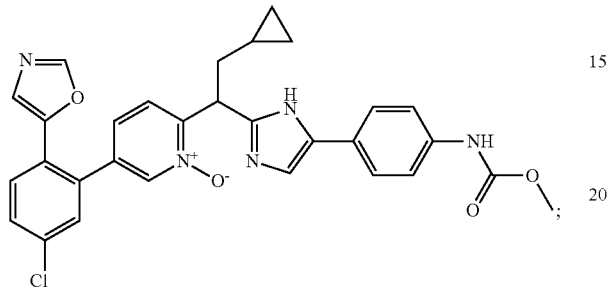
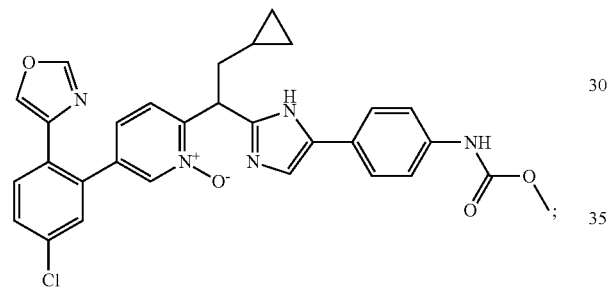
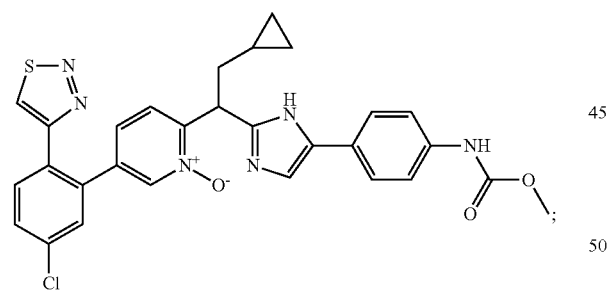
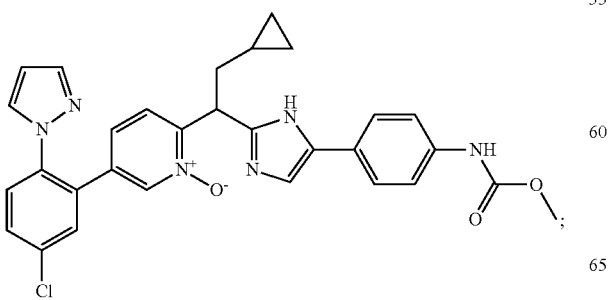
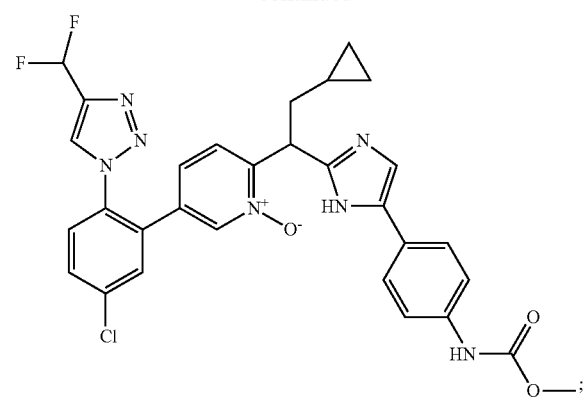
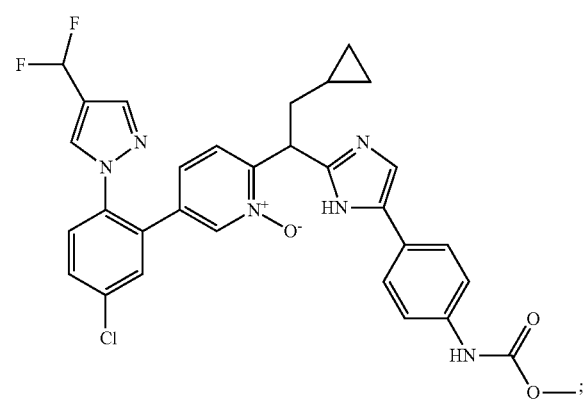
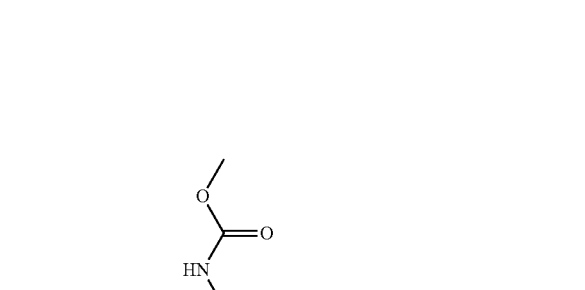
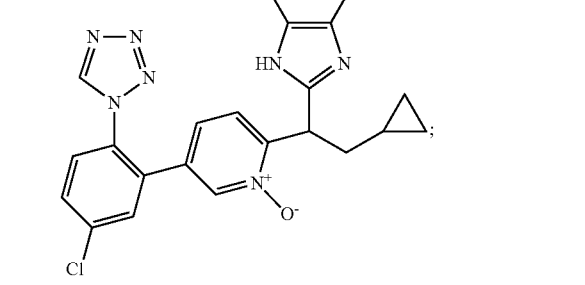

-continued

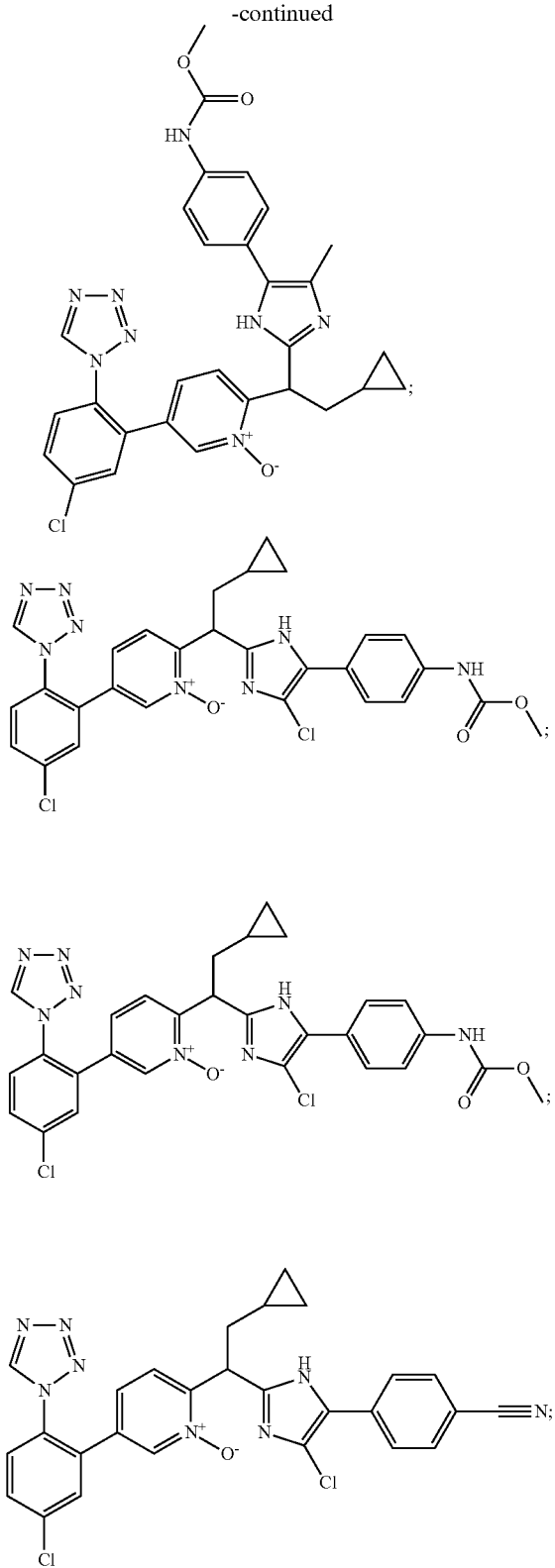

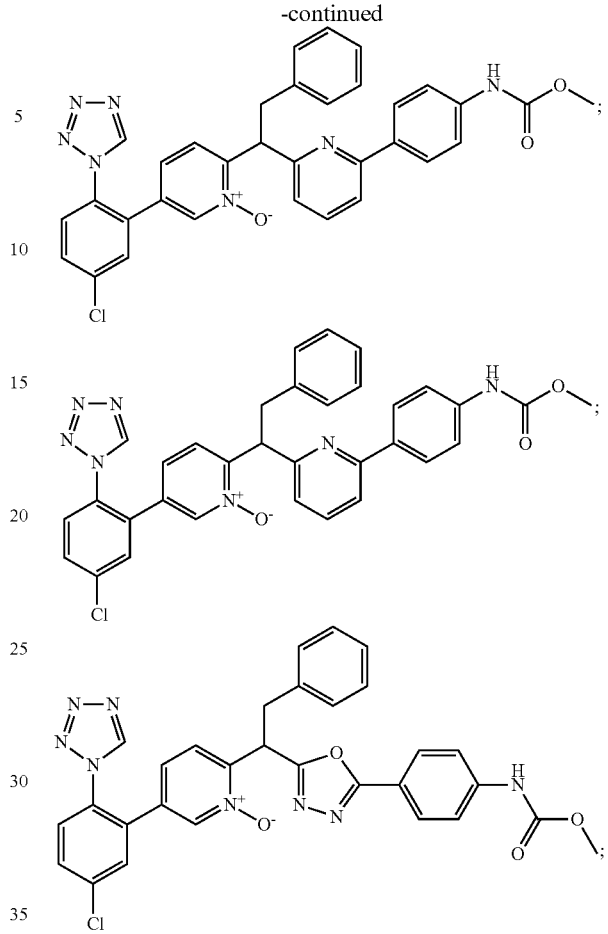

or a pharmaceutically acceptable salt thereof.

11. A pharmaceutical composition comprising a compound of claim 1 or a pharmaceutically acceptable salt thereof and a pharmaceutically acceptable carrier.

12. A method for inhibiting thrombus formation in blood or treating thrombus formation in blood comprising administering a composition of claim 11 to a mammal in need of thereof.

13. A method for preventing thrombus formation in blood comprising administering a composition of claim 11 to a mammal in need thereof.

14. A method of treating venous thromboembolism and pulmonary embolism in a mammal comprising administering a composition of claim 11 to a mammal in need thereof.

15. A method of treating deep vein thrombosis in a mammal comprising administering a composition of claim 11 to a mammal in need thereof.

16. A method of treating thromboembolic stroke in a human comprising administering a composition of claim 11 to a mammal in need thereof.

* * * * *